United States Patent
Sheng et al.

(10) Patent No.: US 11,806,374 B2
(45) Date of Patent: Nov. 7, 2023

(54) ISOLATED RECOMBINANT ONCOLYTIC ADENOVIRUSES, PHARMACEUTICAL COMPOSITIONS, AND USES THEREOF FOR DRUGS FOR TREATMENT OF TUMORS AND/OR CANCERS

(71) Applicant: HANGZHOU CONVERD CO., LTD., Hangzhou (CN)

(72) Inventors: Jipo Sheng, Hangzhou (CN); Jin Fu, Hangzhou (CN); Ronghua Zhao, Hangzhou (CN); Yun Qin, Hangzhou (CN); Lin Chen, Hangzhou (CN); Sanmao Kang, Hangzhou (CN); Fang Hu, Hangzhou (CN)

(73) Assignee: HANGZHOU CONVERD CO., LTD., Hangzhou (CN)

( * ) Notice: Subject to any disclaimer, the term of this patent is extended or adjusted under 35 U.S.C. 154(b) by 609 days.

(21) Appl. No.: 16/650,863

(22) PCT Filed: Jul. 3, 2018

(86) PCT No.: PCT/CN2018/094264
§ 371 (c)(1),
(2) Date: Mar. 26, 2020

(87) PCT Pub. No.: WO2019/062251
PCT Pub. Date: Apr. 4, 2019

(65) Prior Publication Data
US 2020/0276252 A1 Sep. 3, 2020

(30) Foreign Application Priority Data
Sep. 28, 2017 (CN) .......................... 201710899291.6

(51) Int. Cl.
| | | |
|---|---|---|
| A61K 39/23 | (2006.01) | |
| C12N 15/79 | (2006.01) | |
| C07H 21/04 | (2006.01) | |
| A61K 35/761 | (2015.01) | |
| A61P 35/00 | (2006.01) | |
| C12N 7/00 | (2006.01) | |
| C12N 15/113 | (2010.01) | |
| C12N 15/63 | (2006.01) | |
| A61K 48/00 | (2006.01) | |
| C12N 15/64 | (2006.01) | |

(52) U.S. Cl.
CPC .......... *A61K 35/761* (2013.01); *A61K 48/005* (2013.01); *A61P 35/00* (2018.01); *C12N 7/00* (2013.01); *C12N 15/113* (2013.01); *C12N 15/1135* (2013.01); *C12N 15/63* (2013.01); *C12N 15/64* (2013.01); *C12N 2310/531* (2013.01); *C12N 2710/10332* (2013.01); *C12N 2710/10343* (2013.01)

(58) Field of Classification Search
CPC ...... A61K 35/761; C12N 15/85; C12N 15/86; C12N 15/113; C12N 2710/10332; C12N 2710/10343; C12N 2310/14; C07H 21/02; C07H 21/04
See application file for complete search history.

(56) References Cited

U.S. PATENT DOCUMENTS

| | | | |
|---|---|---|---|
| 9,850,500 B2 | 12/2017 | Yun et al. | |
| 10,533,173 B2 | 1/2020 | Zhang et al. | |
| 10,555,981 B2 | 2/2020 | Silvestre et al. | |
| 2006/0270016 A1* | 11/2006 | Holm ................... | A61P 35/00 435/235.1 |
| 2007/0202080 A1 | 8/2007 | Yun et al. | |
| 2013/0101557 A1 | 4/2013 | Yun | |
| 2019/0134119 A1 | 5/2019 | Shafren et al. | |
| 2019/0323035 A1 | 10/2019 | Yun et al. | |

FOREIGN PATENT DOCUMENTS

| | | |
|---|---|---|
| CN | 1384885 A | 12/2002 |
| CN | 1968717 | 5/2007 |
| CN | 101128593 A | 2/2008 |
| CN | 102712934 | 10/2012 |
| CN | 103221423 A | 7/2013 |
| CN | 105307671 A | 2/2016 |
| CN | 106535940 A | 3/2017 |

(Continued)

OTHER PUBLICATIONS

Silvestre CN107208069 2017, pp. 1-57 (Year: 2017).*

(Continued)

*Primary Examiner* — Shin Lin Chen

(74) *Attorney, Agent, or Firm* — Renner, Otto, Boisselle & Sklar, LLP

(57) ABSTRACT

The present disclosure provides an isolated recombinant oncolytic adenovirus, a pharmaceutical composition, and uses thereof for drugs for treatment of tumors and/or cancers. The recombinant oncolytic adenovirus is a selectively replicating oncolytic adenovirus, and the genome of the recombinant oncolytic adenovirus is integrated with a coding sequence of exogenous shRNA capable of inhibiting PDL1 expression in tumor cells. The replication capability of the virus in normal primary cells is much lower than the replication capability of the virus in tumor cells. Moreover, the expressed shPDL1 can significantly reduce the level of PDL1 protein highly expressed in tumor cells. Thus, the oncolytic killing effect of the oncolytic virus and the antitumor immunostimulatory effect of immune cells produce a synergistic effect.

26 Claims, 51 Drawing Sheets
Specification includes a Sequence Listing.

(56) References Cited

FOREIGN PATENT DOCUMENTS

| | | |
|---|---|---|
| CN | 106999577 A | 8/2017 |
| CN | 107208069 | 9/2017 |
| CN | 107073099 A | 8/2018 |
| CN | 109576231 A | 4/2019 |
| JP | 2007531519 A | 11/2007 |
| JP | 2017522025 A | 8/2017 |
| WO | 2005/007855 | 1/2005 |
| WO | 2007/086631 | 8/2007 |
| WO | 2016008976 A1 | 1/2016 |
| WO | 2016/146894 A1 | 9/2016 |
| WO | 2016/177343 | 11/2016 |
| WO | 2016/178167 A1 | 11/2016 |
| WO | 2017/100127 | 6/2017 |
| WO | WO 2017/136748 A1 * | 8/2017 |

OTHER PUBLICATIONS

Casey (Science, p. 1-9, 2016). (Year: 2016).*
Hortobagyi (Human Gene Therapy, 9: 1775-1798, 1998). (Year: 1998).*
Notice of Reasons for Refusal dated Mar. 2, 2022, for corresponding Japanese Patent Application No. 2020-518660.
Xinyu Zheng et al.; Adenoviral E1a Expression Levels Affect Virus-Selective Replication in Human Cancer Cells; Cancer Biology & Therapy; 2005; pp. 1255-1262; vol. 4, Issue 11.
Second Chinese Office Action dated Dec. 13, 2021, for corresponding Chinese Patent Application No. 201710899291.6.
He Wanwan et al.; Oncolytic Adenovirus as a Vector of Gene Therapy for Cancer Progression and Safety Evaluation; Chinese Journal of Cell Biology; published 2013; pp. 1386-1391.
Zhezhu Han et al.; Survivin silencing and TRAIL expression using oncolytic adenovirus increase anti-tumorigenic activity in gemcitabine-resistant pancreatic cancer cells; published Dec. 16, 2015; vol. 21, pp. 351-364.
Yiali Yuan et al.; Basic Immunology and Pathogenic Biology; Traditional Chinese Medicine Publishing House; published Aug. 31, 2016; pp. 1-308.
Extended European Search Report dated Jun. 2, 2021, for related European Patent Application No. 18862842.4.
JD Dias et al., "Targeted cancer immunotherapy with oncolytic adenovirus coding for a fully human monoclonal antibody specific for CTLA-4"; Gene Therapy; Jan. 1, 2011.
Christine E Engeland et al.; "CTLA-4 and PD-L1 Checkpoint Blockade Enhances Oncolytic Measles Virus Therapy"; Molecular Therapy; Aug. 26, 2014; vol. 22, No. 11, pp. 1949-1959.
Maxine Bauzon et al.; "Armed therapeutic viruses—a disruptive therapy on the horizon of cancer immunotherapy" Frontiers in Immunology; Jan. 1, 2014; vol. 4.
International Search Report and Written Opinion dated Sep. 14, 2018, for International Patent Application No. PCT/CN2018/094263.
Ke Xu; Combination of CIK Cells and Oncolytic Adenovirus Expressing hIL12-p40-L/\p35 Gene in Cancer Treatment; Medicine & Public Health, China Master Theses Full-Text-Database; No. 5; Jun. 15, 2012, pp. 1-40.
Huiping Wang et al.; Combination of oncolytic adenovirus and endostatin inhibits human retinoblastoma in an in vivo mouse model; International Journal of Molecular Medicine 31; 2013; pp. 377-385.
Su Fei et al.; Construction of a New Kind of Recombinant Adenovirus and Its effect on Tumor Cells; Virologica Sinica; Dec. 31, 1999; pp. 304-309; vol. 14, No. 4.
Li-Jun Mao et al.; Construction of conditionally replicative adenovirus expressing shRNA targeting hTERT gene and its anti tumor effect in vitro; Journal of Practical Oncology; 2007; pp. 12-17; vol. 22, No. 1.
Yunglong Qi et al.; Current Status and Prospects of Autologous NK Cell Therapy in Biotherapy of Lung Cancer; Journal of Practical Oncology; Dec. 31, 2012; vol. 27, No. 6; pp. 570-572.
Joshua C. Doloff et al.; Human Telomerase Reverse Transcriptase Promoter-Driven Oncolytic Adenovirus with E1B-19 kDa and E1B-55 kDa Gene Deletions; Human Gene Therapy; Dec. 5, 2008; pp. 1383-1399.
Henry Ogbomo et al.; Immunotherapy in gliomas: limitations and potential of natural killer (NK) cell therapy; Trends in Molecular Medicine, Aug. 31, 2011; vol. 17, No. 8; pp. 433-441.
First Office Action for corresponding Chinese Patent Application No. CN201710899291.6 dated Apr. 23, 2021.

* cited by examiner

ISOLATED RECOMBINANT ONCOLYTIC ADENOVIRUSES, PHARMACEUTICAL COMPOSITIONS, AND USES THEREOF FOR DRUGS FOR TREATMENT OF TUMORS AND/OR CANCERS

This application is a national phase of International Application No, PCT/CN2018/094264 filed Jul. 3, 2018, which claims priority to Chinese Patent Application No. 201710899291.6, filed Sep. 28, 2017.

FIELD OF THE PRESENT DISCLOSURE

The present disclosure relates to the field of biotechnology, and particularly to isolated recombinant oncolytic adenoviruses, pharmaceutical compositions, and use thereof for drugs for treatment of tumors and/or cancers.

BACKGROUND OF THE PRESENT DISCLOSURE

According to the latest report on the cause of death of the population published on the World Health Organization website in January 2013, about 7.6 million people died of cancer in 2008, which are accounting for 13% of the world's total deaths, and this number is growing rapidly every year. It is estimated that this number will exceed 13.1 million by 2030. In China, the incidence of malignant tumors is increasing at a rate of 3% to 5% per year. In 2002, the number of new cases of malignant tumors in China reached 2.19 million. By 2020, the number of new patients will exceed 3 million each year. Cancer has become one of the leading causes of death in the world. Moreover, the treatment of tumors has become the focus and difficulty in the medical field nowadays, and is receiving more and more attention.

Tumorigenesis is a multi-factor and multi-step process. The main reason is that cells are stimulated by external carcinogens (including physical radiation, chemicals and viruses, etc). When cells are damaged, genetic materials such as DNA (deoxyribonucleic acid) in the cells are changed, and further, the signal transduction pathways in the cells are abnormal and disordered, the cells are subjected to crazy proliferation, apoptosis resistance, differentiation stopping, and possess the capacity of invading tissues and migration, and the functions of important organs in a human body are influenced to endanger life. At present, the main methods for treatment tumors include surgery therapy, radiation therapy, chemotherapy, biological therapy and immunotherapy. Although these methods can help control tumor to some extent, they still cannot solve the problem fundamentally.

Oncolytic virus therapy also belongs to the field of biological therapy. The research of oncolytic virus can be traced back to the 1950s. At that time, a cervical cancer patient was found to have tumor regression after being infected with rabies virus. Inspired by the phenomenon that for some cancer patients, tumor was spontaneously relieved after they were infected with virus, researches on oncolytic virus have begun from then. Oncolytic viruses refer to a class of viruses that can selectively replicate in target cells after infecting tumor cells and eventually cause tumor cells to lyse and die. This type of virus relies on their specificity to replicate in tumor cells, so as to lyse tumor cells, and the viruses released after cell lysis can further infect the peripheral tumor cells, while they have no damaging effect on normal cells and tissues, or has less impact. Oncolytic viruses can be generally divided into two classes: one class is a wild-type virus and a naturally mutated attenuated virus strain. Such viruses naturally have affinity for certain tumor cells, such as reovirus, Newcastle disease virus, and autonomously replicating parvovirus, etc. These viruses can amplify in certain tumor cells and lyse the cells, and have natural specific oncolytic activity. The other class is virus that can only replicate in tumor cells after the virus genome is genetically engineered. At present, adenovirus, herpes simplex virus, influenza virus and human vaccinia virus have been genetically engineered. The research on adenovirus in oncolytic virus is relatively early, and the oncolytic mechanism is relatively clear. Furthermore, the research on adenovirus type 5 is more clear among adenoviruses. Shortly after adenovirus was discovered, it was used to treat head and neck malignancies. After injection of adenovirus, the tumors became smaller in different degrees, but the tumors tended to recur after treatment and the effect was difficult to maintain. Until 1996, Bischoff et al., first reported that the recombinant adenovirus Onyx-015 which is deleted in a part of E1B can selectively replicate in p53 abnormal tumor cells and cause tumor killing. Oncolytic adenovirus research has once again received widespread attention and has developed rapidly. Therefore, many new types of oncolytic adenoviruses have emerged. In 2006, China approved a human recombinant adenovirus type 5 H101 (an oncolytic adenovirus deleted in the E1B55K and E3 genes) developed by Shanghai Sunway Biotech Co., Ltd. (NDA: Sinopharm Zhunzi S20060027). This human recombinant adenovirus can specifically replicate in and lyse tumor cells of p53 mutant tumor cells. Oncolytic adenovirus has increasingly become a new method for treatment of malignant tumors.

In addition, tumor immunotherapy is also a very important means in the fight against tumors. It mainly includes antibody therapy, T cell therapy and tumor vaccine. Antibodies are called new target drugs for cancer. They can help to activate effector cells by targeting immune cells around the tumor, and promote more effective anti-tumor immunity. They can also kill tumor cells through complement-dependent cytotoxicity, or by inducing Tumor cell apoptosis. T-cell therapy is a method of intravenously administering tumor-specific autologous T cells (eg, CAR-T) expanded in vitro into the body. Tumor vaccine therapy is a method of generating specific antibodies and effector T cells by regulating the immune system of the body, which is also called active specific immunotherapy. A large number of clinical experiments have proved that tumor immunotherapy has a very positive effect in the treatment of tumors, but the most difficult problem in tumor immunotherapy is tumor escape. There is a very complicated relationship between the immune escape mechanism of tumors and the immune response of the body to tumors. In the process of tumor immunotherapy, tumor-specific $CD8^+$ T cells are activated in the early stage and lose their killing function as the tumor develops to the later stage. Generally, in addition to a first signal, T cell activation requires a series of co-stimulatory molecules to provide a second signal in order to make the T cell to reach the physiological activation threshold, thereby produce a normal immune response, wherein the first signal is provided to antigen-specific T cells via MHC-antigen peptide presented by APC. If the second signal provided by the co-stimulatory molecule is absent, it will lead to non-reactivity or specific immune tolerance of T cells and even to apoptosis. Therefore, the regulation of the positive and negative co-stimulatory signals and the balance between them play an important regulatory role in the entire process of the body's immune response.

There is still a need for more effective treatment regimens and drugs developed for that in the immunotherapy of tumors and/or cancers.

SUMMARY OF THE PRESENT DISCLOSURE

In order to solve the above-mentioned problems in the art, the present disclosure provides isolated recombinant oncolytic adenoviruses, pharmaceutical compositions, and uses thereof for drugs for treatment of tumors and/or cancers.

Specifically, the present disclosure provides:

(1) An isolated recombinant oncolytic adenovirus, wherein the recombinant oncolytic adenovirus is a selectively replicating oncolytic adenovirus and the genome of the recombinant oncolytic adenovirus is integrated with a coding sequence of an exogenous shRNA capable of inhibiting the expression of PDL1 in tumor cells.

(2) The recombinant oncolytic adenovirus according to (1), wherein the coding sequence of the exogenous shRNA is as shown in any one of SEQ ID NOs. 16, 19, and 22.

(3) The recombinant oncolytic adenovirus according to (1), wherein the genome of the recombinant oncolytic adenovirus is lack of the E1B19K gene, the E1B55K gene, and all the genes in E3 region.

(4) The recombinant oncolytic adenovirus according to (1) or (3), wherein the genome of the recombinant oncolytic adenovirus comprises a coding sequence of the E1A gene; preferably, the coding sequence of the E1A gene is under the control of a CMV promoter.

(5) The recombinant oncolytic adenovirus according to (1), wherein the recombinant oncolytic adenovirus is obtained by genetically modifying an adenovirus type 5.

(6) A pharmaceutical composition, wherein the pharmaceutical composition comprises the recombinant oncolytic adenovirus according to any one of (1) to (5) as an active ingredient, and a pharmaceutically acceptable excipient.

(7) The pharmaceutical composition according to (6), wherein the pharmaceutical composition comprises the recombinant oncolytic adenovirus in a dose ranging from $5\times10^7$ to $5\times10^{12}$ vp/day.

(8) The pharmaceutical composition according to (6), wherein the recombinant oncolytic adenovirus is formulated to be administered via intratumoral injection or administered intravenously.

(9) A vector for preparing the recombinant oncolytic adenovirus according to any one of (1) to (5), wherein the vector contains a coding sequence of exogenous shRNA under the control of a promoter, and the coding sequence of the shRNA is as shown in any one of SEQ ID NOs. 16, 19 and 22.

(10) The vector according to (9), wherein the vector uses pShuttle as a basic backbone, and the basic backbone orderly comprises an operatively linked promoter controlling the expression of the coding sequence of the exogenous shRNA, the coding sequence of the exogenous shRNA, a promoter controlling the expression of the coding sequence of the E1A gene, and the coding sequence of the E1A gene.

(11) A host cell comprising the vector according to (9) or (10).

(12) The host cell according to (11), wherein the host cell stably expresses the vector.

(13) An isolated shRNA, wherein the coding sequence of the shRNA is as shown in any one of SEQ ID NOs. 16, 19 and 22, and the shRNA is capable of inhibiting the expression of PDL1 in tumor cells.

(14) Use of the recombinant oncolytic adenovirus according to any one of (1) to (5) for preparation of drugs for treatment of tumors and/or cancers.

(15) The use according to (14), wherein the tumors and/or cancers include lung cancer, melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, leukemia, bone cancer, and testicular cancer.

(16) A method for treating tumors and/or cancers, comprising administering the recombinant oncolytic adenovirus according to any one of (1) to (5) to a tumor and/or cancer patient.

(17) The method according to (16), wherein the recombinant oncolytic adenovirus is given at a dose ranging from $5\times10^7$ to $5\times10^{12}$ vp/day, once or twice per day, consecutively for 1 to 7 days.

(18) The method according to (16), wherein the recombinant oncolytic adenovirus is administered via intratumoral injection or administered intravenously.

(19) The method according to (16), wherein the tumors and/or cancers include lung cancer, melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, leukemia, bone cancer, and testicular cancer.

(20) An isolated recombinant oncolytic adenovirus, wherein the recombinant oncolytic adenovirus is a selectively replicating oncolytic adenovirus and the genome of the recombinant oncolytic adenovirus is lack of the E1B19K gene, the E1B55K gene, and all the genes in E3 gene region; preferably, the genome of the recombinant oncolytic adenovirus comprises coding sequence of the E1A gene; more preferably, the coding sequence of the E1A gene is under the control of a CMV promoter.

The present invention has the following advantages and positive effects compared to the prior art The present invention firstly proposes a conception of deleting coding regions of the E1B19K gene, the E1B55K gene and all the E3 genes from oncolytic adenovirus and simultaneously making the oncolytic adenovirus carry coding sequence of exogenous shRNA so as to make the resulted recombinant oncolytic adenovirus selectively replicates in tumor cells and expresses a shRNA capable of inhibiting PDL1 expression in tumor cells. The oncolytic adenovirus provided thereby had superior tumor killing effect, and its replication capacity in normal cells was much lower than that in tumor cells, so that its toxicity to normal cells was low and its safety was improved. In addition, the expression level of PDL1 protein in tumor cells can be obviously reduced by the expressed shRNA of the virus and therefore, the immunosuppression of tumor cells on T lymphocytes was reduced. As a result, the anti-tumor immune killing effect of T and NK lymphocytes was enhanced. The present invention also found that a synergistic effect of the oncolytic killing effect of the oncolytic virus and the anti-tumor immunostimulation effect of T or NK lymphocytes can be achieved by integrating the oncolytic adenoviruses with the shRNA coding sequence.

In addition, since the recombinant oncolytic adenovirus of the present invention selectively replicates in tumor cells and simultaneously expresses shRNA capable of inhibiting expression of PDL1 in tumor cells, the anti-tumor immune effect of immune cells (including T lymphocytes and NK cells) got enhanced. Therefore, the anti-tumor immune response of the body can be synergistically stimulated, thus the recombinant oncolytic adenovirus of the present invention can be used with NK cells. The pharmacological composition and the method provided based on the conception of the present invention fully exert the roles of selectively replicating in and killing tumor cells and further causing subsequent immune response of the body of the recombinant oncolytic adenovirus, and, at the same time, also fully exert the function of NK cell in killing tumor cells. Also, the advantage that the recombinant oncolytic adenovirus can selectively replicate in the tumor cells was artfully utilized, so that the recombinant oncolytic adenovirus-contained tumor cells become specific targets for NK cells, which further resulting in improved synergistic effect of tumor killing functions.

Furthermore, researches were carried out according to the present disclosure, and the dose levels for each of the recombinant oncolytic adenovirus and NK cells, administration sequence thereof and intervals between the administrations were provided to achieve the best synergistic effect for the combined therapy, while avoiding antagonistic effects, so as to provide an effective treatment for tumors and/or cancers.

Definitions

As used herein, the terms "tumor", "cancer", "tumor cell" and "cancer cell" cover the meanings generally recognized in the art.

As used herein, the term "oncolytic virus" refers to a virus that can replicate selectively in and lyse tumor cells.

As used herein, the term "therapeutically effective dose" refers to an amount of a functional agent or of a pharmaceutical composition useful for exhibiting a detectable therapeutic or inhibitory effect or invoking an antitumor response. The effect can be detected by any assay method known in the art.

As used herein, the term "administer" or "administration" refers to providing a compound, a composite or a composition (including viruses and cells) to a subject.

As used herein, the term "patient" refers to a human or non-human organism. Thus, the methods and compositions described herein are applicable to both human and veterinary diseases. In certain embodiments, the patient has a tumor. In some cases, the patient may suffer from one or more types of cancer simultaneously.

As used herein, the term "synergistic effect" refers to an effect arising between two or more agents that produce an effect greater than the sum of their individual effects.

As used herein, the term "pfu", or "plaque forming unit" refers to the number of viruses forming a plaque.

As used herein, the term "VP" refers to number of viral particles.

As used herein, the term "VP/kg" refers to number of viral particles per kilogram of patient's body weight.

As used herein, the term "TCID50" stands for median tissue culture infective dose and refers to the viral dose that leads to infection and causes a cytopathic effect in 50% of the tissue culture.

As used herein, the term "MOI", or "multiplicity of infection" refers to the ratio between the number of viruses and the number of cells, i.e., the number of virus particles used to initiate viral infection per cell. MOI=pfu/cell, that is, the number of cells×MOI=Total PFU.

DETAILED DESCRIPTION

The present disclosure is further explained with the following detailed description of preferred embodiments with references to the accompanying drawings, which is not to be taken in a limiting sense, and it will be apparent to those skilled in the art that various modifications or improvements can be made accordingly without departing from the spirit of the present disclosure and these are therefore within the scope of the present disclosure.

In the present disclosure, the words "tumor", "cancer", "tumor cell", and "cancer cell" encompass the meaning commonly recognized in the art.

Human body is a complex organism comprising ten systems which include respiratory system, circulatory system, digestive system, and etc. These systems coordinate with each other, which allow for normal function of all kinds of complicated life activities. When a tumor occurs, human body develops anti-tumor responses via multiple, closely correlated immune effects or mechanisms, including cell-mediated immunity and humoral immunity and involving various immune effector molecules and effector cells. It has been generally believed that cell-mediated immunity plays a major role in an anti-tumor process, and that humoral immunity plays more secondary role under some conditions. The present disclosure propose to utilize the characteristic of oncolytic adenovirus selectively replicating in the tumor cells and killing tumor cells, and simultaneously to make the oncolytic adenovirus carry the coding sequence of exogenous shRNA capable of inhibiting PDL1 expression in tumor cells, so as to enable the recombinant oncolytic adenovirus synergistically play the roles of selectively lysing tumor and enhancing the anti-tumor immune effect of the body. Based on the conception, the inventor of the present disclosure found, through experimental research and theoretical exploration, that the above synergistic effect can be achieved by deleting the coding regions of the E1B19K gene, the E1B55K gene and all the E3 genes of an oncolytic adenovirus and integrating its genome with exogenous shRNA coding sequence.

Figure 24:
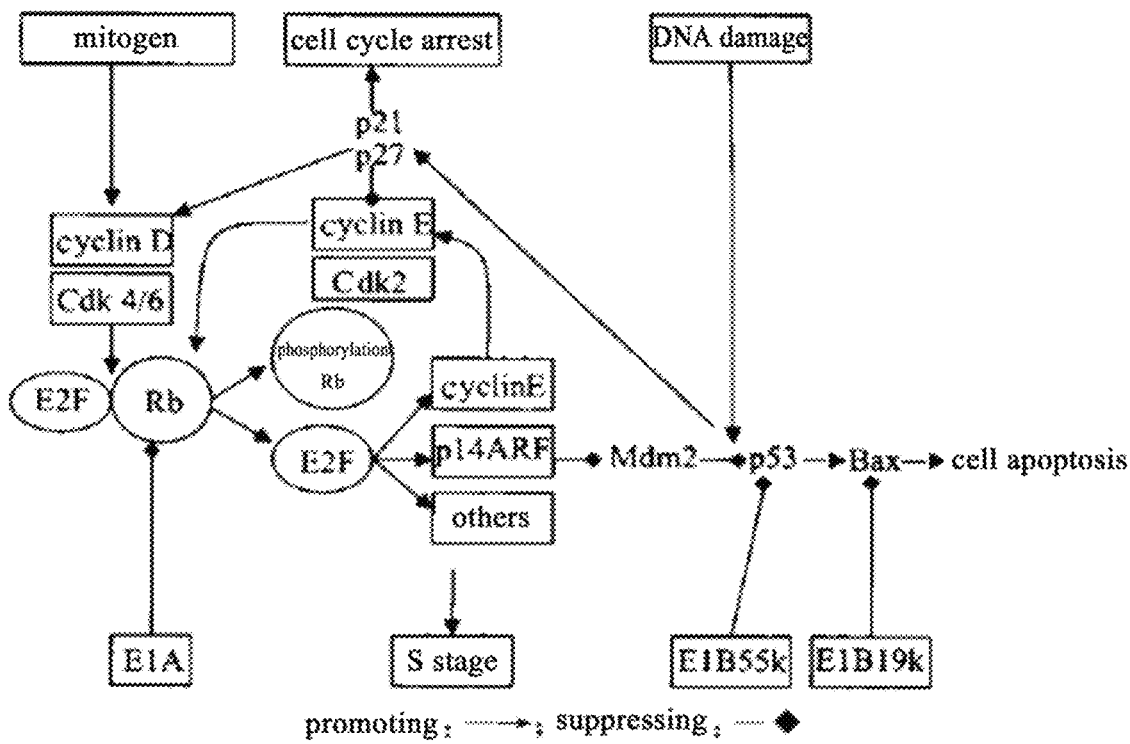
FIG. 24 shows a schematic diagram indicating p53 and Rb signaling pathways in cells.
Figure 25:
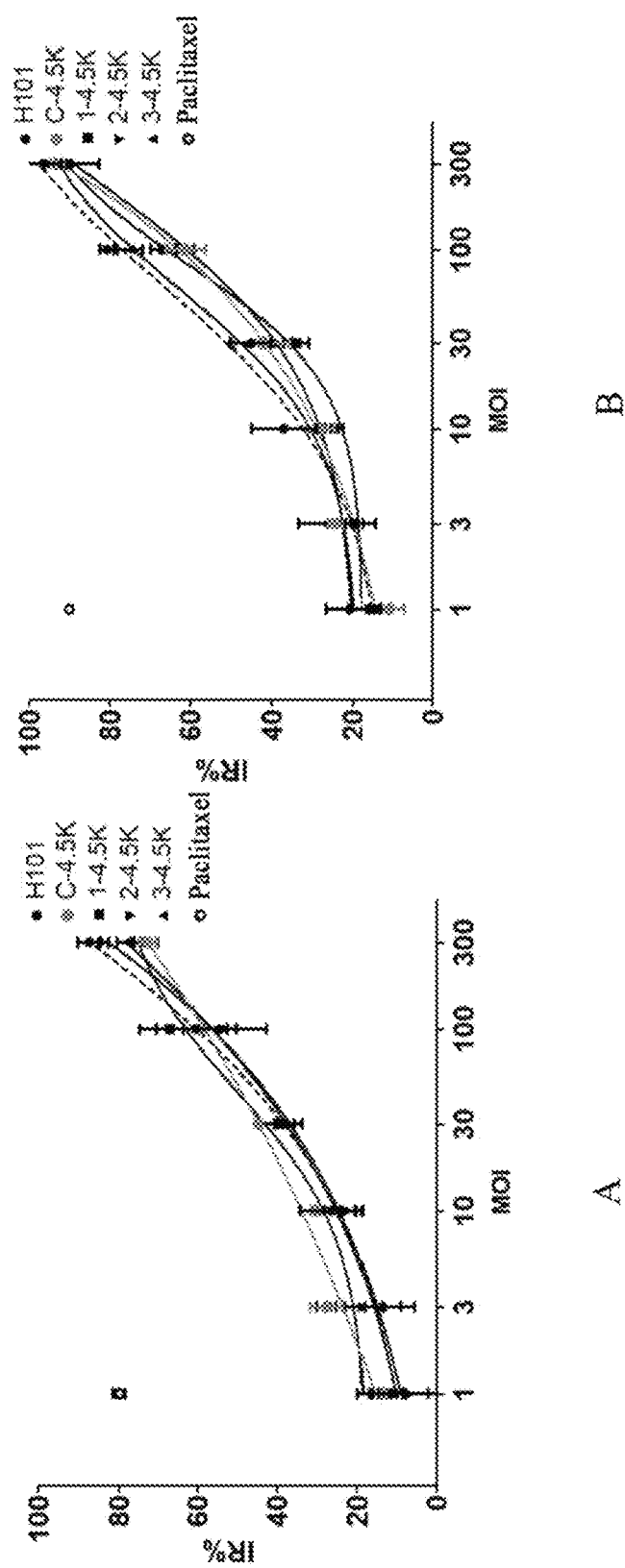
FIG. 25 shows the killing effect on HCT116 cells of oncolytic viruses OAd-shPDL1 (OAd-shPDL1 #1-4.5K (1-4.5K), OAd-shPDL1 #2-4.5K (2-4.5K) and OAd-shPDL1 #3-4.5K (3-4.5K)), and system control virus OAd-C-4.5K (C-4.5K) constructed according to the present disclosure, as well as control group H101 and control group paclitaxel in Example 4. The abscissa represents different virus infection dose (unit: MOI) used to treat the cells, and the ordinate represents the inhibition rate (%) on the cell growth after the treatment with viruses. FIG. A shows the results of the 48-hour experiment, and FIG. B shows the results of the 72-hour experiment.
Figure 26:
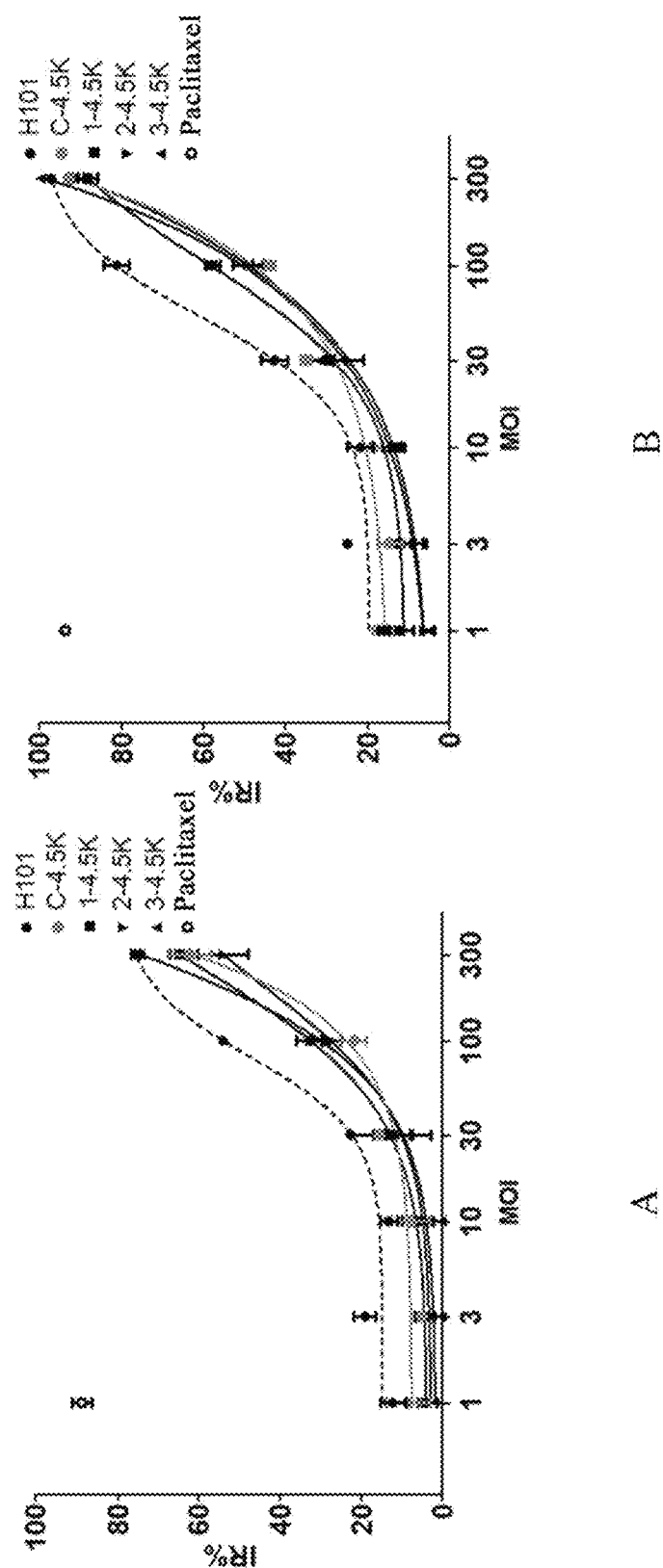
FIG. 26 shows the killing effect on PANC1 cells of oncolytic viruses OAd-shPDL1 (OAd-shPDL1 #1-4.5K (1-4.5K), OAd-shPDL1 #2-4.5K (2-4.5K) and OAdshPDL1 #3-4.5K (3-4.5K)), and system control virus OAd-C-4.5K (C-4.5K) constructed according to the present disclosure, as well as control group H101 and control group paclitaxel in Example 4. The abscissa represents different virus infection dose (unit: MOI) used to treat the cells, and the ordinate represents the inhibition rate (%) on the cell growth after treatment with viruses. FIG. A shows the results of the 48-hour experiment, and FIG. B shows the results of the 72-hour experiment.
Figure 27:
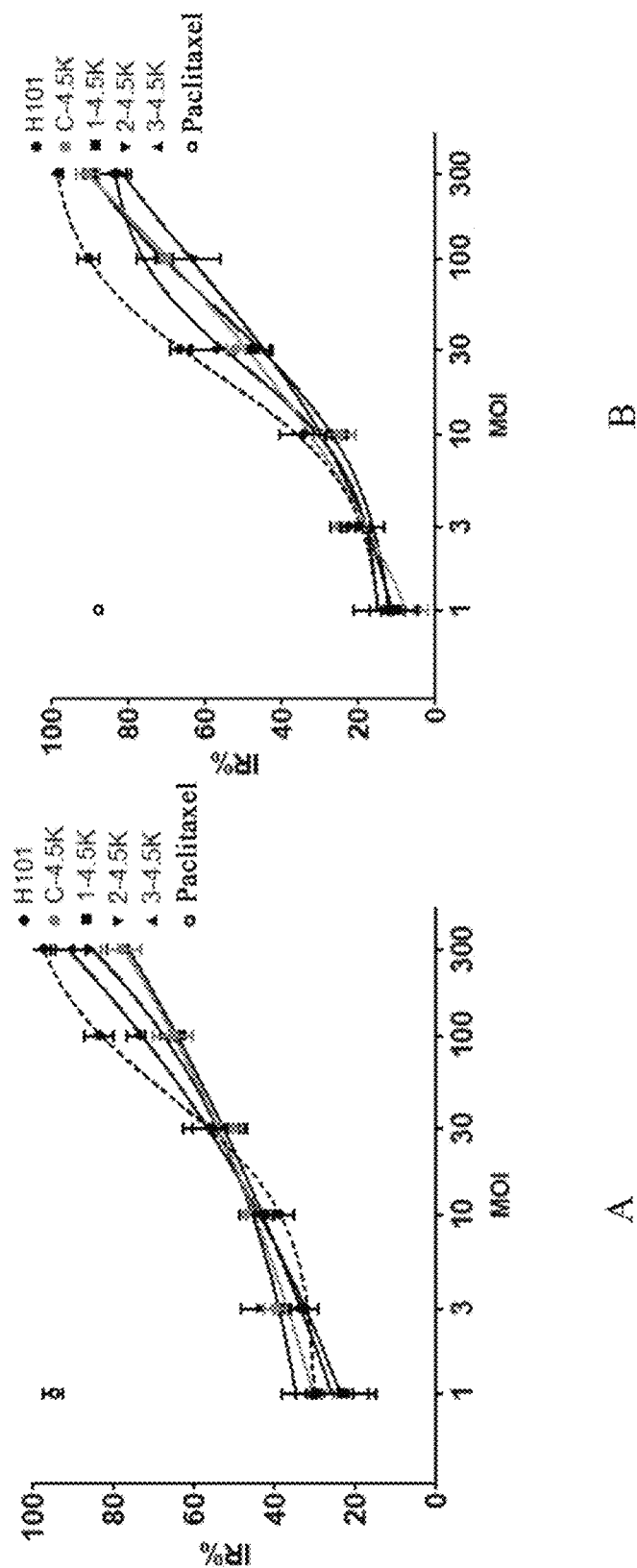
FIG. 27 shows the killing effect on HT29 cells of oncolytic viruses OAd-shPDL1 (OAd-shPDL1 #1-4.5K (1-4.5K), OAd-shPDL1 #2-4.5K (2-4.5K) and OAd-shPDL1 #3-4.5K (3-4.5K)), and system control virus OAd-C-4.5K (C-4.5K) constructed according to the present disclosure, as well as control group H101 and control group paclitaxel in Example 4. The abscissa represents different virus infection dose (unit: MOI) used to treat the cells, and the ordinate represents the inhibition rate (%) on the cell growth after treatment with viruses. FIG. A shows the results of the 48-hour experiment, and FIG. B shows the results of the 72-hour experiment.
Figure 28:
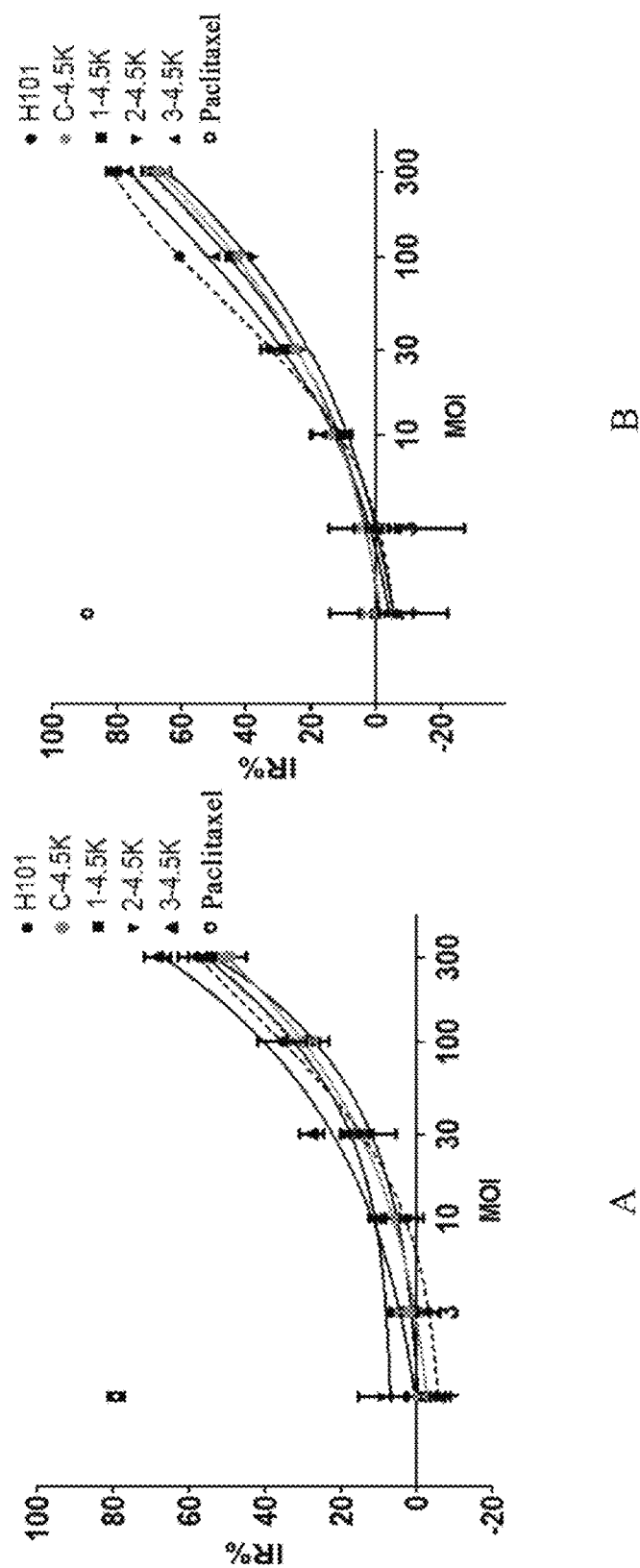
FIG. 28 shows the killing effect on H460 cells of oncolytic viruses OAd-shPDL1 (OAd-shPDL1 #1-4.5K (1-4.5K), OAd-shPDL1 #2-4.5K (2-4.5K) and OAd-shPDL1 #3-4.5K (3-4.5K)), and system control virus OAd-C-4.5K (C-4.5K) constructed according to the present disclosure, as well as control group H101 and control group paclitaxel in Example 4. The abscissa represents different virus infection dose (unit: MOI) used to treat the cells, and the ordinate represents the inhibition rate (%) on the cell growth after treatment with viruses. FIG. A shows the results of the 48-hour experiment, and FIG. B shows the results of the 72-hour experiment.
Figure 29:
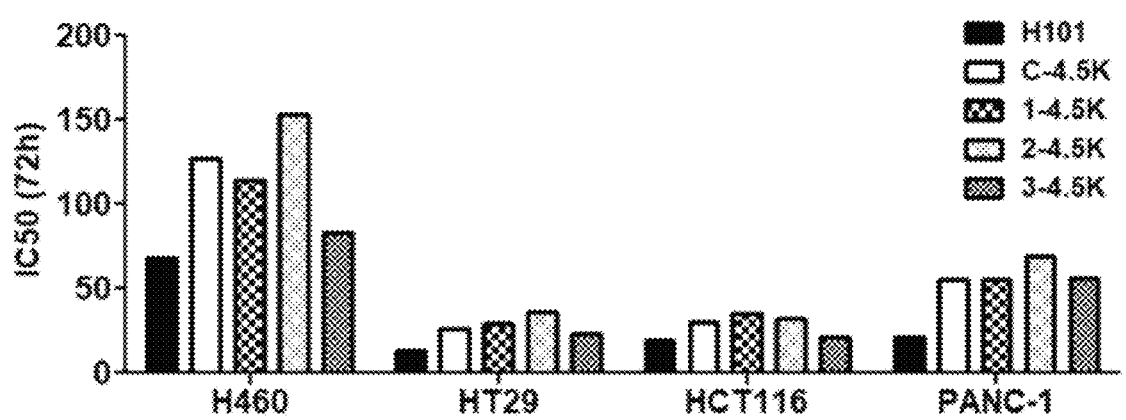
FIG. 29 shows the comparison results of the $IC_{50}$ (72 h) doses against different cells of oncolytic viruses OAd-shPDL1 (OAd-shPDL1 #1-4.5K (1-4.5K), OAd-shPDL1 #2-4.5K (2-4.5K) and OAd-shPDL1 #3-4.5K (3-4.5K)) and the system control virus OAd-C-4.5K (C-4.5K) constructed according to the present disclosure, and the control group H101 in Example 4. The abscissa represents different types of tumor cell groups, and the ordinate represents the number of viruses (unit: MOI) that can kill 50% of the corresponding tumor cells when the cells were incubated with the viruses for 72 hours.

In addition, many DNA viruses, such as adenovirus, can alter the cell cycle of the host. That mainly because the viruses produce proteins that acted on cell cycle regulatory proteins of the host cell to allow the resting phase cells to enter the cell cycle so as to facilitate the replication of viral DNA. Different viruses affect the cell cycle in different mechanisms, and adenoviruses interfere the host cell cycle mainly through Rb and p53 cell signaling pathways (FIG. 24) (see: Chenjianfa et al, the research progress of oncolytic adenovirus, Tumor prevention and cure research, 2004, 31 (4): 243-245). The oncolytic function of oncolytic adenovirus is achieved by altering the expression of cyclins of host cell based on this principle. The genome of an adenovirus comprises four early transcription units (i.e., E1, E2, E3 and E4) with regulatory function and one late transcription unit. E1 is divided into two parts, DA and E1B, as shown in FIG. 24. E1A combines to Rb and releases free E2F, and cells enter into the S phase from the G1 phase; two proteins E1B55k and E1B19k are coded and generated by adenovirus to respectively inhibit p53 and Bax, so that the division and proliferation of host cells are not inhibited by p53 cell signaling pathway and a large number of host cells enter into the division phase from the resting phase. As a result, the adenovirus is replicated and propagated in large scale. However, the adenovirus whose E1A gene is deleted cannot code E1A protein to release free E2F when infecting host cells, and G1 phase cells cannot enter into S phase. Similarly, even though the adenovirus whose E1B gene is deleted can produce E1A protein to allow the host cell to enter S phase from G1 phase, the cell entering into the division cycle will undergo apoptosis or blocked division through the p53 signaling pathway. Therefore, the adenovirus lack of the E1A or E1B gene cannot replicate and proliferate in host cells with normal Rb and p53 cell signaling pathways, but can only proliferate in tumor cells with abnormal Rb or p53 signaling pathways. The early oncolytic adenoviruses Onyx-015 and H101 achieve their selective replication in p53 mutant tumor cells both through the deletion of the E1B55K gene of the adenovirus (partial or complete deletion of the sequence in E3 region). When such viruses infect normal host cells, the adenoviruses in the cells cannot be effectively replicated due to the fact that the p53 arrestin E1B55K cannot be coded and produced and the infected cells entering the division phase are subjected to division inhibition or apoptosis through p53 signalling pathway, even if the viruses can code and produce E1A protein to make Rb-E2F conjugate separate to release free E2F and the infected cells enter the S phase from G1 phase. In cells with abnormal p53 signalling pathway, the infected cells entering the division stage will not undergo division inhibition or apoptosis through the p53 signalling pathway, so that the cells proliferate greatly and adenoviruses in the cells replicate in large scale to cause cell lysis. However, the experiments later demonstrated that the selective replication of said two kinds of viruses in normal cells was not as ideal as expected. The reason may be that they were only deleted with E1B55K, but still retained the normal expression of E1B19K, while according to FIG. 24, E1B55K and E1B19K exert similar effect in the p53 signaling pathway. Therefore, although deletion of the E1B55K cannot inhibit the function of wild-type p53, the normal expression of E1B19K protein could still inhibit the function of Bax in the downstream of p53, so that oncolytic adenovirus could also replicate in normal cells. In the oncolytic adenovirus described in the present disclosure, E1B55K and E1B19K genes were both deleted at the same time in addition to the deletion of the E3 region, so that the viruses had better selective replication in tumor cells, lower replication capacity in normal cells and better safety to normal cells compared to the oncolytic adenovirus in the prior art.

On the other hand, PD-L1 (also called PDL1 or B7-H1) belongs to B7 family and has IgV and IgC-like regions, a transmembrane region and a cytoplasmic region. The molecule has wide tissue expression spectrum and high expression in some tumor cell lines. Many researches showed that the molecule was related to the immune escape mechanism of tumors. The microenvironment around the tumor can induce wide expression of PD-L1 on the tumor cells, and the expressed PD-L1 is beneficial to the generation and the growth of the tumor. The PD-L1 expressed by tumor cells and APCs in tumor microenvironment interacts with receptor PD1 on T cells to inhibit the activation of tumor antigen specific T cells through PD-1/PD-L1 signalling pathway and down-regulate the tumor immune response mediated by T cells. In addition, there was research showing that the blocking of the PD-L1/PD-1 signalling pathway can promote the proliferation of tumor antigen specific T cells, up-regulate the secretion of IFN-gamma in infiltrating $CD8^+$ T cells and effectively inhibit tumor growth, which indicates that the blocking of the PD-1/PD-L1 signalling pathway plays an important role in tumor immune response aiming at inducing immune response. Moreover, experiments proved that the immune activation effect of a tumor vaccine can be effectively strengthened by tumor immunotherapy using anti-PD-L1 monoclonal antibody combined with the tumor vaccine, and the influence of tumor microenvironment on the treatment effect can be reduced thereby.

Based on the above theoretical research and exploration, the oncolytic adenovirus of the present disclosure was not only reconstructed on the genome thereof to enable it to have stronger oncolytic killing capability, but also was added with a coding frame capable of expressing shPDL1 (shRNA for inhibiting PDL1 expression). It is expected that the mRNA of intracellular PDL1 can be efficiently degraded by shPDL1 so as to realize gene silencing of PDL1, reduction of the expression of PDL1 in tumor cells, weakeness of the transmission of PD1/PDL1 signalling pathway to the T cell inhibition signal and enhancement of the killing effect of the T cells on tumors. Therefore, the oncolytic virus of the present disclosure can not only be used alone as an oncolytic agent, but also be used as an effective vector for the shPDL1 coding frame to allow the shPDL1 to be expressed in a large amount along with the virus replication, and thereby playing double functions of virus therapy and gene therapy simultaneously.

Accordingly, the present disclosure provides an isolated recombinant oncolytic adenovirus, wherein the recombinant oncolytic adenovirus is a selectively replicating oncolytic adenovirus and the genome of the recombinant oncolytic adenovirus is integrated with a coding sequence of an exogenous shRNA capable of inhibiting PDL1 expression in tumor cells.

Preferably, the coding sequence of the exogenous shRNA is as shown in any one of SEQ ID NOs. 16, 19 and 22.

Preferably, the recombinant oncolytic adenovirus is lack of the E1B19K gene, the E1B55K gene, and all genes in E3 region.

The possible mechanisms of tumor cell lysis caused by oncolytic virus after it enters tumor cells are as follows: (1) Direct cytotoxicity of viral proteins: Both death proteins and advanced proteins produced by, for example, adenovirus could effectively mediate the lysis of tumor cell. (2) Generate anti-tumor immune response: On the one hand, the virus can kill tumors by increasing the sensitivity of tumor cells to a variety of cytokines. For example, adenovirus enhances tumor necrosis factor-mediated tumor killing by replicating and expressing E1A protein in infected tumor cells. On the other hand, when tumor cells are infected by a virus, the virus antigen on the surface of tumor cells forms a complex with the major histocompatibility complex class I antigen, which can be easily recognized by cytotoxic T lymphocytes, thereby mediating specific attacks on virus-infected tumor cells. (3) Enhance the sensitivity of tumor cells to radiotherapy and chemotherapy: The expression product of adenovirus E1A gene is a powerful chemical sensitizer. The expression product of E1A gene in tumor cells can induce high-level expression of p53 protein, thereby enhancing the damage to DNA caused by chemotherapy and radiotherapy.

Therefore, preferably, the genome of the recombinant oncolytic adenovirus includes the E1A gene coding sequence. More preferably, the E1A gene coding sequence is under the control of a CMV promoter, thereby enhancing the oncolytic killing effect on tumor cells by increasing the expression of E1A.

Preferably, the recombinant oncolytic adenovirus is obtained by genetically modifying adenovirus type 5. One example of adenovirus type 5 is H101.

In a preferred embodiment, the oncolytic adenovirus genome integrates with a coding frame including a U6 promoter and human PDL1 shRNA (shPDL1) after the ES sequence, and an E1A expression cassette including a CMV promoter, an E1A coding region and its 3' UTR region and SV40polyA.

The recombinant oncolytic adenovirus of the present disclosure has strong killing effect on various human tumor cells (such as human neurogliocytoma cell U251, human lung cancer cell A549, human cervical cancer cell Hela, human large cell lung cancer H460, human colorectal cancer cell HCT116, human pancreatic cancer cell PANC1, human colon cancer cell HT29, etc.). The replication capacity of the virus in normal human primary cells is much lower than that in human tumor cells (a difference of about two orders of magnitude). The human shPDL1 expressed by the virus can significantly reduce the level of highly expressed PDL1 protein in human tumor cells.

Based on the recombinant oncolytic adenovirus developed by the present disclosure, the present disclosure also provides a pharmaceutical composition, wherein the pharmaceutical composition comprises the recombinant oncolytic adenovirus according to the present disclosure as an active ingredient, and pharmaceutically acceptable excipients.

Preferably, the pharmaceutical compositions comprise a therapeutically effective amount of the recombinant oncolytic adenovirus. More preferably, the therapeutically effective amount of the recombinant oncolytic adenovirus is a dose ranging from $5 \times 10^7$ to $5 \times 10^{12}$ vp/day.

The oncolytic viruses can be administered through the common administration routes in the art; for example, being administered via intratumoral injection or intravenously administration.

The pharmaceutical compositions of the present disclosure may also contain other active ingredients known in the art, such as interleukin-2 (IL-2), IL-15, IL-18, granulocyte-macrophage colony-stimulating factor (GM-CSF), Interferon-$\gamma$ (IFN-$\gamma$), tumor necrosis factor-$\alpha$ (TNF-$\alpha$), and etc., and the dosage and administration route thereof can be performed in their respective conventional manners. If other active ingredients are comprised, the recombinant oncolytic adenovirus should be present in the pharmaceutical compositions independently without being mixed with other active ingredients. For example, the recombinant oncolytic adenovirus is contained separately in a separate container.

Those skilled in the art will understand that the pharmaceutical compositions of the present disclosure may further include suitable pharmaceutically acceptable excipients.

In another aspect, provided is a vector for preparing the recombinant oncolytic adenovirus according to the present disclosure, wherein the vector comprises an exogenous shRNA coding sequence under the control of a promoter, and the shRNA coding sequence is as shown in any one of SEQ ID NOs. 16, 19, and 22.

In a specific embodiment, the vector uses the pShuttle as basic backbone, and the basic backbone comprises orderly an operatively linked promoter controlling the expression of the exogenous shRNA coding sequence, the exogenous shRNA coding sequence, a promoter controlling the expression of the E1A gene coding sequence, and the E1A gene coding sequence.

In another aspect, provided is a host cell containing the vector according to the present disclosure. Preferably, the host cell stably expresses the vector.

In another aspect, provided is an isolated shRNA, wherein the coding sequence of the shRNA is as shown in any one of SEQ ID NOs. 16, 19, and 22, and the shRNA is capable of inhibiting the expression of PDL1 in tumor cells.

In another aspect, provided is the use of the recombinant oncolytic adenovirus according to the present disclosure for the preparation of drugs for treatment of tumors and/or cancers.

The tumors and/or cancers include, but are not limited to, lung cancer (e.g., non-small cell lung cancer), melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, leukemia, bone cancer, and testicular cancer, etc.

Another aspect of the present disclosure also provides a method for treating tumors and/or cancers, comprising administering a recombinant oncolytic adenovirus according to the present disclosure to a patient suffering from tumor and/or cancer.

The tumors and/or cancers include, but are not limited to, lung cancer (e.g., non-small cell lung cancer), melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, leukemia, bone cancer, and testicular cancer, etc.

In a preferred embodiment of the present disclosure, the recombinant oncolytic adenovirus is administrated at a therapeutically effective dose, once or twice per day, consecutively for 1 to 7 days (including consecutively for 1 day, 2 days, 3 days, 4 days, 5 days, 6 days or 7 days). The therapeutically effective amount is a dose preferably ranging from $5\times10^7$-$5\times10^{12}$ vp/day (e.g., $5\times10^7$ to $5\times10^{12}$ vp/day, $5\times10^7$ to $1.5\times10^{12}$ VP/day, $5\times10^8$ to $1\times10^{12}$ VP/day, $1\times10^8$ to $5\times10^{11}$ VP/day, $3\times10^{10}$ to $3\times10^{11}$ VP/day).

If necessary, the recombinant oncolytic adenovirus of the present disclosure can also be used in combination with other drugs, such as interleukin-2 (IL-2), IL-15, IL-18, granulocyte-macrophage colony-stimulating factor (GM-CSF), interferon-γ (IFN-γ), tumor necrosis factor-α (TNF-α), etc., and the dosage and administration route thereof can be performed in their respective conventional manners.

Based on specific situations and needs, the method for the treatment of tumors and/or cancers according to the present disclosure can be applied to a patient for one time or multiple times.

The oncolytic viruses can be administered through the common administration routes in the art; for example, they can be administered via intratumoral injection or administered intravenously.

According to another aspect of the present disclosure, provided is an isolated recombinant oncolytic adenovirus, wherein the recombinant oncolytic adenovirus is a selectively replicating oncolytic adenovirus, and the genome of the recombinant oncolytic adenovirus is lack of the E1B19K gene, the E1B55K gene, and all genes in the E3 region. Preferably, the genome of the recombinant oncolytic adenovirus comprises E1A gene coding sequence; more preferably, the E1A gene coding sequence is under the control of a CMV promoter.

The oncolytic adenovirus has strong tumor killing effect, and its replication ability in normal cells is far lower than its replication ability in tumor cells. Therefore, it has low toxicity to normal cells with improved safety.

In another aspect of the present disclosure, the inventors of the present disclosure also propose a new combination therapy based on the above-mentioned oncolytic adenovirus in combination with systemic thinking. Currently, many non-cytotoxic anti-tumor drugs do not improve long-term survivals in tumor patients when combined with chemotherapy. This may be due to the lack of systemic thinking in these combination therapies. For example, traditional chemotherapies primarily interfere with certain stages of cell life cycle such as synthesis of RNA or DNA, and mitosis, and so, mainly target fast-growing cells. Consequently, while these chemotherapies can kill tumor cells, they also can cause damage to the immune system; when the immune system is weakened, the growth of tumor cells can become unstoppable. A systemic thinking is such an approach that it is based on an integrated concept and takes into account comprehensively the correlations and interactions between drug actions, diseases, systems and human body. On the basis of the above-mentioned systemic thinking, it is possible to maximize efficacy while minimizing damaging to the immune system by employing other approaches for improving the immune function and systematically combining various therapies according to the present disclosure. Accordingly, the disclosure provides a novel combination therapy involving the recombinant oncolytic adenovirus and NK cells for the treatment of tumors and/or cancers. Particularly, a synergistic effect can be achieved by only combining the recombinant oncolytic adenovirus and NK cells according to the present disclosure.

Therefore, the present disclosure further provides a therapeutic agent comprising
(a) a first pharmaceutical composition comprising the recombinant oncolytic adenovirus of the present disclosure in a first pharmaceutically acceptable carrier; and
(b) a second pharmaceutical composition comprising NK cells in a second pharmaceutically acceptable carrier.

Preferably, the first pharmaceutical composition and the second pharmaceutical composition are provided separately in the pharmaceutical composition without being mixed together.

In some embodiments, the first pharmaceutically acceptable carrier and the second pharmaceutically acceptable carrier are the same. In other embodiments, the first pharmaceutically acceptable carrier and the second pharmaceutically acceptable carrier are different.

In some cases, the therapeutic agent can also be interpreted as a combination of drugs.

In some embodiments, the active ingredient of the first pharmaceutical composition is the recombinant oncolytic adenovirus, and the active ingredient of the second pharmaceutical composition is NK cells. In some embodiments, the first pharmaceutical composition comprises the recombinant oncolytic adenovirus at a therapeutically effective dose (preferably, the first pharmaceutical composition comprises the recombinant oncolytic adenovirus at a dose ranging from $5\times10^7$-$5\times10^{12}$ vp/day, more preferably from $5\times10^7$ to $1.5\times10^{12}$ VP/day, more preferably from $5\times10^9$ to $1\times10^{12}$ VP/day, more preferably from $1\times10^9$ to $5\times10^{11}$ VP/day, and still more preferably from $3\times10^{10}$ to $3\times10^{11}$ VP/day), and the second pharmaceutical composition comprises the NK cells at a dose ranging from $1\times10^7$ to $1\times10^{10}$ cells/day (preferably from $1\times10^9$ to $5\times10^9$ cells/day, more preferably from $1\times10^9$ to $4\times10^9$ cells/day, and still more preferably from $1\times10^9$ to $3\times10^9$ cells/day).

The present disclosure also provides a pharmaceutical composition, wherein the active ingredients of the pharmaceutical composition include the recombinant oncolytic adenovirus of the present disclosure and NK cells. Preferably, the active ingredients of the pharmaceutical composition consist of the recombinant oncolytic adenovirus and NK cells.

Preferably, the recombinant oncolytic adenovirus and NK cells are provided separately in the pharmaceutical composition without being mixed together.

The mechanisms through which oncolytic viruses kill tumor cells are generally similar. In various embodiments, the oncolytic viruses are administered via intratumoral injection or administered intravenously, and when the oncolytic viruses come into contact with tumor cells, they will infect and enter the tumor cells. Since the oncolytic virus mainly replicates and reproduces in tumor cells with little to no replication in normal cells, large amounts of progeny oncolytic viruses can be produced in the infected tumor cells, leading to lysis and death of the tumor cells. When the tumor cells lyse, large numbers of tumor-associated antigens and the progeny oncolytic viruses may be released, and the antigens can then further activate the immune system in vivo, stimulating NK cells and T cells in vivo to continue to attack the remaining tumor cells. Meanwhile, the progeny oncolytic viruses can infect the tumor cells which have not been infected yet.

NK cells are immune cells which can kill a broad spectrum of tumor cells, and NK cells can distinguish tumor cells from normal cells. When NK cells come into contact with tumor cells, they can recognize tumor cells as abnormal cells, and will kill the tumor cells through multiple assisting processes such as receptor recognition, target recognition by antibodies (ADCC), as well as releases of granzymes, perforins and interferons capable of killing the tumor cells indirectly. An in vitro study has indicated that a healthy NK cell is able to kill up to 27 tumor cells during its life cycle.

NK cells also have anti-virus functions. If normal cells are infected by viruses, the viruses will replicate massively and the infected cells will become aged, showing changes in the composition of protein clusters on the cellular membrane thereof. During this process, NK cells are able to recognize the infected cells sensitively and effectively, and kill these cells with similar approaches they use to kill tumor cells as described above, so as to inhibit replication and proliferation of viruses in the normal cells. Afterwards, with activation of antigens and participation of immune factors like interferons, other types of immune cells will continue to fight against viruses.

In the present disclosure, individual features of the oncolytic virus and NK cells have been taken into account, so they can be combined skillfully. When combined together, the anti-virus mechanism of NK cells is also applicable to tumor cells infected by the oncolytic virus, and this is complementary to the anti-tumor mechanism of NK cells. In addition, the combination therapy allows the tumor cells infected by the oncolytic viruses to become specific targets for NK cells, which can improve their tumor killing effect. The oncolytic viruses not only replicate selectively in cancer cells and kill them from inside, but may also cause the protein receptor clusters on the cellular membrane to change and thus facilitate the recognition of cancer cells by NK cells, so that NK cells can attack the cancer cells from outside. Therefore, the oncolytic virus and NK cells synergistically kill cancer cells, achieving improved efficacy.

The NK cells in the present disclosure include autologous NK cells and allogeneic NK cells. The NK cells may be in vitro expanded NK cells. The technology for massive in vitro expansion of NK cells is known in the art and highly developed (see, for example, "Somanchi S S, Lee D A. Ex Vivo Expansion of Human NK Cells Using K562 Engineered to Express Membrane Bound IL21. Methods Mol Biol. 2016; 1441:175-93" or "Phan M T, Lee S H, Kim S K, Cho D. Expansion of NK Cells Using Genetically Engineered K562 Feeder Cells. Methods Mol Biol. 2016; 1441: 167-74"). It has been demonstrated from clinical data that when autologous NK cells, semi-allogeneic NK cells (belonging to allogeneic NK cells) or umbilical cord blood-derived NK cells were infused into human body, no toxicities or long-term dependency had been observed, and the treatment was safe and effective.

The purity of the NK cells useful for the treatment may be 85% or more for the autologous NK cells and 90% or more for the allogeneic NK cells, and the impurity cells therein may be NK-T and/or γδ T cells. Preferably, the NK cell activity (survival rate) is 90% or more, and the NK cell killing activity is 80% or more.

Based on the combination strategies in the present disclosure, further explorations and improvements are made regarding respective dose levels of the recombinant oncolytic adenovirus and NK cells, administration sequence thereof and intervals between the administrations, which are essential for determining the anti-tumor efficacy of the recombinant oncolytic adenovirus, the anti-tumor efficacy of NK cells and the best synergistic killing effect of the combination of the two against tumor cells.

Therefore, preferably, the pharmaceutical composition or therapeutic agent comprises the recombinant oncolytic adenovirus at a therapeutically effective dose (preferably, the pharmaceutical composition or therapeutic agent comprises the recombinant oncolytic adenovirus at a dose ranging from $5\times10^7$-$5\times10^{12}$ vp/day, more preferably from $5\times10^7$ to $1.5\times10^{12}$ VP/day, more preferably from $5\times10^8$ to $1\times10^{12}$ VP/day, more preferably from $1\times10^9$ to $5\times10^{11}$ VP/day, and still more preferably from $3\times10^{10}$ to $3\times10^{11}$ VP/day), and the pharmaceutical composition or therapeutic agent includes NK cells at a dose ranging from $1\times10^7$ to $1\times10^{10}$ cells/day (preferably from $1\times10^8$ to $5\times10^9$ cells/day, more preferably from $1\times10^9$ to $4\times10^9$ cells/day, and still more preferably from $1\times10^9$ to $3\times10^9$ cells/day).

The recombinant oncolytic adenoviruses can be administered through the routes commonly used in the art; for example, they can be administered via intratumoral injection or administered intravenously.

NK cells can be administered through the routes commonly used in the art; for example, they can be administered intravenously.

In specific embodiments, the active ingredients of the pharmaceutical composition or therapeutic agent according to the present disclosure include the recombinant oncolytic adenovirus at a dose ranging from $5\times10^7$ to $5\times10^{12}$ VP/day (e.g., $5\times10^7$ to $1.5\times10^{12}$ VP/day, $5\times10^8$ to $1\times10^{12}$ VP/day, $1\times10^9$ to $5\times10^{11}$ VP/day, $3\times10^{10}$ to $3\times10^{11}$ VP/day, etc.) and NK cells at a dose ranging from $1\times10^7$ to $1\times10^{10}$ cells/day (e.g., $1\times10^8$ to $5\times10^9$ cells/day, $1\times10^9$ to $4\times10^9$ cells/day, $1\times10^9$ to $3\times10^9$ cells/day, etc.). Preferably, the active ingredients of the pharmaceutical composition or therapeutic agent consist of the recombinant oncolytic adenovirus at a dose ranging from $5\times10^7$ to $5\times10^{12}$ VP/day (e.g., $5\times10^7$ to $1.5\times10^{12}$ VP/day, $5\times10^8$ to $1\times10^{12}$ VP/day, $1\times10^9$ to $5\times10^{11}$ VP/day, $3\times10^{10}$ to $3\times10^{11}$ VP/day, etc.) and NK cells at a dose ranging from $1\times10^7$ to $1\times10^{10}$ cells/day (e.g., $1\times10^8$ to $5\times10^9$ cells/day, $1\times10^9$ to $4\times10^9$ cells/day, $1\times10^9$ to $3\times10^9$ cells/day, etc.).

A person skilled in the art can understand that the pharmaceutical composition or therapeutic agent according to the present disclosure can also include suitable pharmaceutical excipients.

The pharmaceutical composition or therapeutic agent according to the present disclosure may also include other active ingredients known in the field, such as interleukin-2 (IL-2), granulocyte-macrophage colony stimulating factor (GM-CSF), interferon-γ (IFN-γ), tumor necrosis factor-α (TNF-α), etc.

In some embodiments, the pharmaceutical composition or therapeutic agent of the present disclosure comprises one or more pharmaceutically acceptable carriers. Pharmaceutical formulations can be prepared by procedures known in the art. For example, the active ingredients including compounds and the like can be formulated with common excipients, diluents (such as phosphate buffer or saline), tissue-culture medium, and carriers (such as autologous plasma or human serum albumin) and administered as a suspension. Other carriers can include liposomes, micelles, nanocapsules, polymeric nanoparticles, solid lipid particles (see, e.g., E. Koren and V. Torchilin, Life, 63:586-595, 2011). Details on techniques for formulation of the pharmaceutical composition or therapeutic agent disclosed herein are well described in the scientific and patent literature, see, e.g., the latest edition of Remington's Pharmaceutical Sciences, Maack Publishing Co., Easton Pa. ("Remington's").

The pharmaceutical composition or therapeutic agent according to the present disclosure can be used to treat various tumors and/or cancers, including, but not limited to, lung cancer (e.g., non-small cell lung cancer), melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, leukemia, bone cancer, and testicular cancer.

The application method of the pharmaceutical composition or therapeutic agent of the present disclosure is as follows: first, administering the recombinant oncolytic adenovirus to a patient having tumor and/or cancer; then, 18-72 hours (e.g., 20-70 hours, 22-48 hours, 24-48 hours, 30-48 hours, etc.) after the administration of the recombinant oncolytic adenovirus, administering the NK cells to the tumor and/or cancer patient. The phrase "18-72 hours (e.g., 20-70 hours, 22-48 hours, 24-48 hours, 30-48 hours, etc.) after the administration of the recombinant oncolytic adenovirus, administering the NK cells to the tumor and/or cancer patient" means that the time interval between the first administration of the NK cells and the first administration of the recombinant oncolytic adenovirus is in the range of 18-72 hours (e.g., 20-70 hours, 22-48 hours, 24-48 hours, 30-48 hours, etc.), or the time interval between the first administration of the NK cells and the most recent administration of the recombinant oncolytic adenovirus is in the range of 18-72 hours (e.g., 20-70 hours, 22-48 hours, 24-48 hours, 30-48 hours, etc.). Preferably, the time interval between the first administration of the NK cells and the most recent administration of the recombinant oncolytic adenovirus is in the range of 18-72 hours (e.g., 20-70 hours, 22-48 hours, 24-48 hours, 30-48 hours, etc.). More preferably, the time interval between the first administration of the NK cells and the most recent administration of the recombinant oncolytic adenovirus is in the range of 24-48 hours.

In a preferred embodiment of the present disclosure, the recombinant oncolytic adenovirus is given at a therapeutically effective dose (e.g., $5 \times 10^7$ to $5 \times 10^{12}$ vp/day, $5 \times 10^7$ to $1.5 \times 10^{12}$ VP/day, $5 \times 10^8$ to $1 \times 10^{12}$ VP/day, $1 \times 10^9$ to $5 \times 10^{11}$ VP/day, $3 \times 10^{10}$ to $3 \times 10^{11}$ VP/day), once or twice per day, consecutively for 1 to 7 days (e.g., once per day, consecutively for 1 to 6 days); and NK cells are given at a dose level ranging from $1 \times 10^7$ to $1 \times 10^{10}$ cells/day (e.g., $1 \times 10^8$ to $5 \times 10^9$ cells/day, $1 \times 10^9$ to $4 \times 10^9$ cells/day, or $1 \times 10^9$ to $3 \times 10^9$ cells/day) once per day, consecutively for 1 to 6 days. In another preferred embodiment of the present disclosure, the recombinant oncolytic adenovirus is given at a therapeutically effective dose (e.g., $5 \times 10^7$ to $5 \times 10^{12}$ vp/day, $5 \times 10^7$ to $1.5 \times 10^{12}$ VP/day, $5 \times 10^8$ to $1 \times 10^{12}$ VP/day, $1 \times 10^9$ to $5 \times 10^{11}$ VP/day, $3 \times 10^{10}$ to $3 \times 10^{11}$ VP/day) every other day, consecutively for 2 to 6 days; and NK cells are given at a dose level ranging from $1 \times 10^7$ to $1 \times 10^{10}$ cells/day (e.g., $1 \times 10^8$ to $5 \times 10^9$ cells/day, $1 \times 10^9$ to $4 \times 10^9$ cells/day, or $1 \times 10^9$ to $3 \times 10^9$ cells/day) every other day, consecutively for 2 to 6 days. Any one of the above mentioned embodiments or any other alternative embodiment can be adopted according to the present disclosure, as long as the NK cells are to be given to the tumor and/or cancer patient 18 to 72 hours after administration of the recombinant oncolytic adenovirus. The recombinant oncolytic adenovirus and NK cells may be administered alternatively (for example, administering the recombinant oncolytic adenovirus on day 1, administering the NK cells on day 2, administering the recombinant oncolytic adenovirus on day 3, and administering the NK cells on day 4, and so on); or may be administered sequentially (for example, administering the recombinant oncolytic adenovirus on day 1, administering the recombinant oncolytic adenovirus and NK cells in a sequential order on day 2, administering the recombinant oncolytic adenovirus and NK cells in a sequential order on day 3, and administering the recombinant oncolytic adenovirus and NK cells in a sequential order on day 4, and so on); or may be administered using other dosage regimens (for example, first, administering the recombinant oncolytic adenovirus, once or twice per day, for consecutive 1 to 7 days (for example, once per day consecutively for 1 to 6 days), and after an interval of 18 to 72 hours, administering NK cells once per day for consecutive 1 to 6 days). Preferably, the recombinant oncolytic adenovirus is administered first, and the NK cells are administered 18 to 72 hours after completion of administrating all the doses of recombinant oncolytic adenovirus. In a preferred embodiment of the present disclosure, first, the tumor and/or cancer patient is given the recombinant oncolytic adenovirus, and the recombinant oncolytic adenovirus is given once only at a therapeutically effective dose (for example, $5 \times 10^7$ to $5 \times 10^{12}$ vp, $5 \times 10^7$ to $1.5 \times 10^{12}$ VP, $5 \times 10^8$ to $1 \times 10^{12}$ VP, $1 \times 10^9$ to $5 \times 10^{11}$ vp, $3 \times 10^{10}$ to $3 \times 10^{11}$ VP); 18 to 72 hours after administration of the recombinant oncolytic adenovirus, the tumor and/or cancer patient is administered the NK cells, and the NK cells are administered once only at a dose level ranging from $1 \times 10^7$ to $1 \times 10^{10}$ cells (e.g., $1 \times 10^8$ to $5 \times 10^9$ cells, $1 \times 10^9$ to $4 \times 10^9$ cells, or $1 \times 10^9$ to $3 \times 10^9$ cells).

The recombinant oncolytic adenoviruses can selectively replicate in tumor or cancer cells and the amount thereof will reach a peak after a certain period of time. The inventors of the present disclosure have discovered that after a period of viral replication, the recombinant oncolytic adenoviruses in tumor cells can promote the killing effect of NK cells against tumor cells. Therefore, the intervals between the administrations of the recombinant oncolytic adenovirus and NK cells proposed in the present disclosure can enable that the peak values of their functions overlap.

The present disclosure also provides use of therapeutic agents of the disclosure for the preparation of drugs for treatment of tumors and/or cancers.

The tumors and/or cancers include, but are not limited to, lung cancer (e.g., non-small cell lung cancer), melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, leukemia, bone cancer, and testicular cancer.

The present disclosure also provides a kit of combinational drugs with synergistic effect for treatment of tumors and/or cancers, including a first container containing the recombinant oncolytic adenovirus and a second container containing the NK cells according to the present disclosure, wherein the first container is separate from the second container. The kit further comprises instructions specifying timing and routes of administration. Preferably, the kit consists of independent containers respectively containing the recombinant oncolytic adenovirus and the NK cells according to the present disclosure, and an instruction sheet specifying timing and routes of administration.

The tumors and/or cancers include, but are not limited to, lung cancer (e.g., non-small cell lung cancer), melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, leukemia, bone cancer, and testicular cancer.

Preferably, the first container in the kit containing the recombinant oncolytic adenovirus includes the recombinant oncolytic adenovirus at a therapeutically effective dose (e.g., $5 \times 10^7$ to $5 \times 10^{12}$ VP/day, $5 \times 10^7$ to $1.5 \times 10^{12}$ VP/day, $5 \times 10^8$ to $1 \times 10^{12}$ VP/day, $1 \times 10^9$ to $5 \times 10^{11}$ VP/day, $3 \times 10^{10}$ to $3 \times 10^{11}$ VP/day), and the second container containing NK cells includes NK cells at an amount that is sufficient for providing a dose ranging from $1\times10^7$ to $1\times10^{10}$ cells/day (e.g., $1\times10^8$ to $5\times10^9$ cells/day, $1\times10^9$ to $4\times10^9$ cells/day, $1\times10^9$ to $3\times10^9$ cells/day, etc.).

NK cells may be selected from autologous NK cells and allogeneic NK cells. NK cells may be autologous NK cells obtained from in vitro expansion or allogeneic NK cells obtained from in vitro expansion.

The recombinant oncolytic adenoviruses can be administered through the routes commonly used in the art; for example, they can be administered via intratumor injection or administered intravenously.

NK cells can be administered through the routes commonly used in the art; for example, they can be administered intravenously.

In another aspect, the present disclosure also provides a method for treatment of tumors and/or cancers, comprising, in a sequential manner, the following steps:

1) administering the recombinant oncolytic adenoviruses according to the present disclosure to a tumor and/or cancer patient;
2) 18-72 hours (e.g., 20-70 hours, 22-48 hours, 24-48 hours, 30-48 hours, etc.) after the administration of the recombinant oncolytic adenovirus, administering NK cells according to the present disclosure to the tumor and/or cancer patient.

The phrase "18-72 hours (e.g., 20-70 hours, 22-48 hours, 24-48 hours, 30-48 hours, etc.) after the administration of the recombinant oncolytic adenovirus, administering the NK cells according to the present disclosure to the tumor and/or cancer patient" means that the time interval between the first administration of the NK cells and the first administration of the recombinant oncolytic adenovirus is in the range of 18-72 hours (e.g., 20-70 hours, 22-48 hours, 24-48 hours, 30-48 hours, etc.), or the time interval between the first administration of the NK cells and the most recent administration of the recombinant oncolytic adenovirus is in the range of 18-72 hours (e.g., 20-70 hours, 22-48 hours, 24-48 hours, 30-48 hours, etc.). Preferably, the time interval between the first administration of the NK cells and the most recent administration of the recombinant oncolytic adenovirus is in the range of 18-72 hours (e.g., 20-70 hours, 22-48 hours, 24-48 hours, 30-48 hours, etc.). More preferably, the time interval between the first administration of the NK cells and the most recent administration of the recombinant oncolytic adenovirus is in the range of 24-48 hours.

The tumors and/or cancers include, but are not limited to, lung cancer (e.g., non-small cell lung cancer), melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, leukemia, bone cancer, and testicular cancer, etc.

In a preferred embodiment of the present disclosure, the recombinant oncolytic adenovirus is given at a therapeutically effective dose (e.g., $5\times10^7$ to $5\times10^{12}$ vp/day, $5\times10^7$ to $1.5\times10^{12}$ VP/day, $5\times10^8$ to $1\times10^{12}$ VP/day, $1\times10^9$ to $5\times10^{11}$ VP/day, $3\times10^{10}$ to $3\times10^{11}$ VP/day), once or twice per day, consecutively for 1 to 7 days (e.g., once per day, consecutively for 1 to 6 days); and NK cells are given at a dose level ranging from $1\times10^7$ to $1\times10^{10}$ cells/day (e.g., $1\times10^8$ to $5\times10^9$ cells/day, $1\times10^9$ to $4\times10^9$ cells/day, or $1\times10^9$ to $3\times10^9$ cells/day) once per day, consecutively for 1 to 6 days. In another preferred embodiment of the present disclosure, the recombinant oncolytic adenovirus is given at a therapeutically effective dose (e.g., $5\times10^7$ to $5\times10^{12}$ vp/day, $5\times10^7$ to $1.5\times10^{12}$ VP/day, $5\times10^8$ to $1\times10^{12}$ VP/day, $1\times10^9$ to $5\times10^{11}$ VP/day, $3\times10^{10}$ to $3\times10^{11}$ VP/day) every other day, consecutively for 2 to 6 days; and NK cells are given at a dose level ranging from $1\times10^7$ to $1\times10^{10}$ cells/day (e.g., $1\times10^8$ to $5\times10^9$ cells/day, $1\times10^9$ to $4\times10^9$ cells/day, or $1\times10^9$ to $3\times10^9$ cells/day) every other day, consecutively for 2 to 6 days. Any one of the above mentioned embodiments or any other alternative embodiment can be adopted according to the present disclosure, as long as the NK cells are to be given to the tumor and/or cancer patient 18 to 72 hours after administration of the recombinant oncolytic adenovirus. The recombinant oncolytic adenovirus and NK cells may be administered alternatively (for example, administering the recombinant oncolytic adenovirus on day 1, administering the NK cells on day 2, administering the recombinant oncolytic adenovirus on day 3, and administering the NK cells on day 4, and so on); or may be administered sequentially (for example, administering the recombinant oncolytic adenovirus on day 1, administering the recombinant oncolytic adenovirus and NK cells in a sequential order on day 2, administering the recombinant oncolytic adenovirus and NK cells in a sequential order on day 3, and administering the recombinant oncolytic adenovirus and NK cells in a sequential order on day 4, and so on); or may be administered using other dosage regimens (for example, first, administering the recombinant oncolytic adenovirus, once or twice per day, for consecutive 1 to 7 days (for example, once per day consecutively for 1 to 6 days), and after an interval of 18 to 72 hours, administering NK cells once per day for consecutive 1 to 6 days). Preferably, the recombinant oncolytic adenovirus is administered first, and NK cells are administered 18 to 72 hours after completion of administrating all the doses of recombinant oncolytic adenovirus. In a preferred embodiment of the present disclosure, first, the tumor and/or cancer patient is given the recombinant oncolytic adenovirus, and the recombinant oncolytic adenovirus is given once only at a therapeutically effective dose (for example, $5\times10^7$ to $5\times10^{12}$ vp, $5\times10^7$ to $1.5\times10^{12}$ VP, $5\times10^8$ to $1\times10^{12}$ VP, $1\times10^9$ to $5\times10^{11}$ VP, $3\times10^{10}$ to $3\times10^{11}$ VP); 18 to 72 hours after administration of the recombinant oncolytic adenovirus, the tumor and/or cancer patient is administered NK cells, and NK cells are administered once only at a dose level ranging from $1\times10^7$ to $1\times10^{10}$ cells (e.g., $1\times10^8$ to $5\times10^9$ cells, $1\times10^9$ to $4\times10^9$ cells, or $1\times10^9$ to $3\times10^9$ cells).

Based on specific situations and needs, the method for the treatment of tumors and/or cancers according to the present disclosure can be applied to a patient for one time or multiple times.

NK cells may be selected from autologous NK cells and allogeneic NK cells. NK cells may be autologous NK cells obtained from in vitro expansion or allogeneic NK cells obtained from in vitro expansion.

The recombinant oncolytic adenoviruses can be administered through the respective routes commonly used in the art; for example, they can be administered via intratumoral injection or administered intravenously.

NK cells can be administered through the routes commonly used in the art; for example, they can be administered intravenously.

Hereinafter, the present disclosure will be further explained or described by way of examples, but these examples are not intended to limit the scope of protection of the present disclosure.

EXAMPLES

Unless otherwise specified, the experimental methods used in the following examples are performed using routine experimental procedures, operations, materials, and conditions in the field of biological engineering.

Unless otherwise specified, all the percentage concentrations (%) of the respective agents indicate percentage by volume (%(v/v)).

The materials used in the following examples are as follows:
1. Cells AD293, MRC-5, Hela, A549, U251, HCT116, PANC1, HT29, H460, MDA-MB-231 were purchased from ATCC; HUVEC was purchased from Allcells Biotechnology (Shanghai) Co., Ltd.
2. Oncolytic adenovirus H101 was purchased from Shanghai Sunway Biotech Co., Ltd.
3. NK cells The sources of NK cells used in the experiments are as follows:

The NK cells used in each example were human NK cells cultured and cryopreserved by Hangzhou ConVerd Co., Ltd. The human NK cells were prepared by the following process. As commonly used techniques in the art, a blood collection needle was inserted into an ulnar vein to collect peripheral venous blood of a healthy person for extraction of immune cells PBMCs. Irradiated K562 feeder cells (purchased from Hangzhou Ding Yun Biotech Co., Ltd.) were used to expand NK cells by autologous plasma culture, and the NK cells had a final purity up to 90%, a viability up to 90%, and in vitro tumor cell killing rate up to 85%.
4. Mice were purchased from Beijing Vital River Experimental Animal Technology Co., Ltd.
5. PBS formula: 8 mM $Na_2HPO_4$, 136 mM NaCl, 2 mM $KH_2PO_4$, 2.6 mM KCl, pH 7.2-7.4.
6. The cell counting methods used in the following examples are described below:

CCK8 assay: 10 μl of CCK8 solution was added to cells in each well, then the cells were incubated in an incubator at 37° C. for 1~4 hours, and then shaken on a shaker at low speed for 5 minutes. The crystal substance were fully dissolved and mixed, and absorbance value at 450 nm ($OD_{450}$) was measured by using a microplate reader. Calculation formula of inhibition rate is as follows: Cell proliferation Inhibitory Rate (IR %)=1−($OD_{450}$ tested product-$OD_{450}$ blank)/($OD_{450}$ negative control-$OD_{450}$ blank)×100%.

MTT assay: 10 μl of MTT solution (5 mg/ml) was added to cells in each well, then the cells were incubated in an incubator at 37° C. for 4 hours, the culture medium was drawn and discarded, 150 μl of DMSO was added into each well, and then shaken at low speed on a shaker for 10 minutes. The crystal substance were fully dissolved and mixed, and the absorbance value ($OD_{490}$) at 490 nm was measured using a microplate reader. Calculation formula of inhibition rate: Cell proliferation Inhibitory Rate (IR %)=1−($OD_{490}$ tested product-$OD_{490}$ blank)/($OD_{490}$ negative control-$OD_{490}$ blank)×100%.

Cell counting using Trypan Blue Staining method: the cells were washed with PBS and digested using trypsin, and then the cells were suspended in PBS. To the suspension added Trypan Blue solution to a final concentration of 0.04% (w/v). Then, cell counting was performed under a microscope, during which dead cells were stained blue and living cells remained unstained. The living cell counts were used as final data.
7. Culture plate 6-well cell culture plate (2 ml per well), 12-well cell culture plate (1 ml per well), 24-well cell culture plate (500 μl per well), 96-well Cell culture plates (100 μl per well) used in each example were all obtained from Corning Co., Ltd.

Preparation Example 1: Construction of E1A Gene Expression Vector

Figure 1:
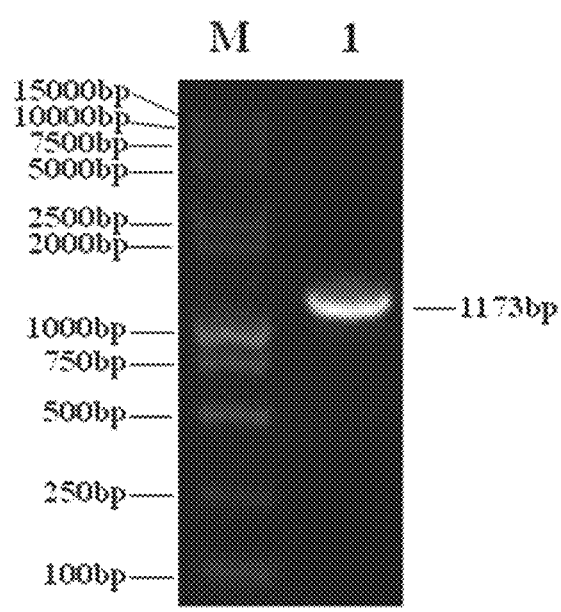
FIG. 1 shows a gel electrophoresis image of the E1A gene of adenovirus type 5 amplified by PCR; wherein lane M is a DNA molecular weight marker and lane 1 is a PCR product which is amplified from H101 genomic DNA template.
Figure 2:
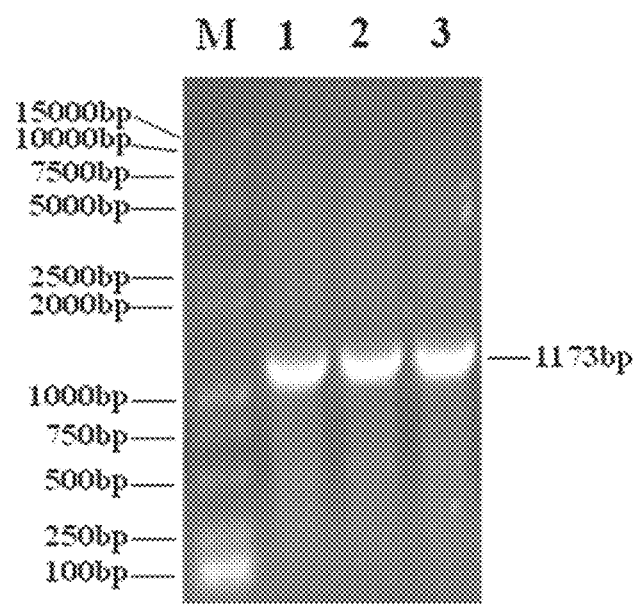
FIG. 2 shows the PCR screening results of the positive clones of pShuttle-E1A plasmid; wherein lane M is the DNA molecular weight marker and lanes 1-3 are candidate clones.
Figure 3:
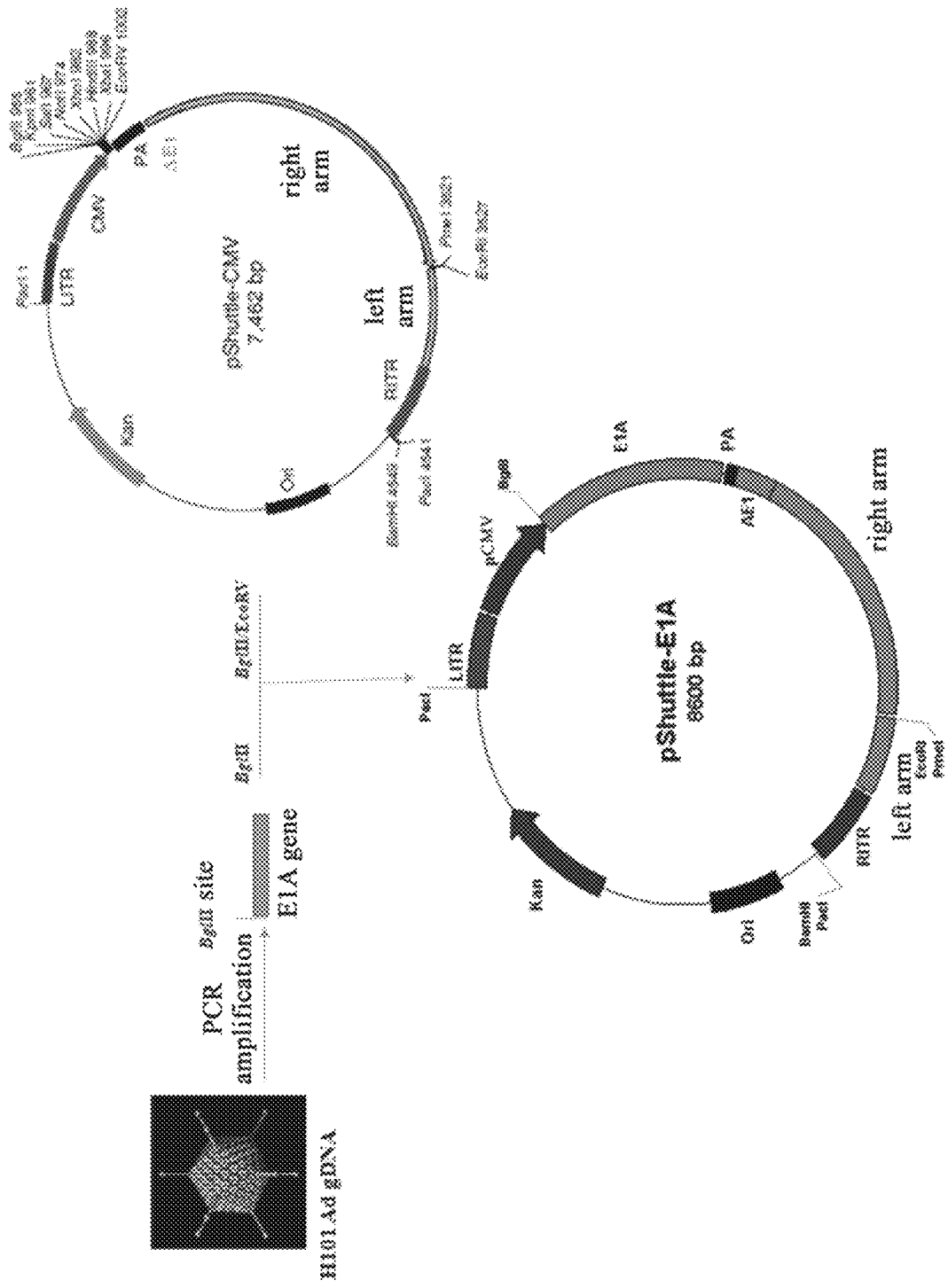
FIG. 3 shows the construction process of pShuttle-E1A plasmid and a map of the constructed plasmid.

Two PCR primers (P1:GGAAGATCTGGACTGAAAAT-GAG (SEQ ID No.1), and P2:TGAGGTCAGATGTAAC-CAAGATTA (SEQ ID No.2); Note: The 5' end of primer P1 is added with a BglII restriction site, which is underlined) were designed based on the human adenovirus type 5 (AD5) genomic DNA sequence (ACCESSION: AC_000008) in Genbank of NCBI (i.e, the National Center for Biotechnology Information; the genomic DNA of the oncolytic virus (H101) produced by Shanghai Sunway Biotech Co., Ltd. was extracted and used as a template, and a 1164 bp sequence between 551-1714 on AD5 genomic DNA was amplified by high-fidelity PCR from the template. The actual size is 1173 bp (see FIG. 1). This sequence includes the coding region of the E1A gene (excluding the E1A promoter sequence) and part of the 3'UTR region. The obtained PCR product was digested with BglII and was cloned into the multiple cloning site region (MCS) between BglII and the EcoRV site on the vector pShuttle-CMV (purchased from Agilent), so as to obtain an intermediate vector pShuttle-E1A. The obtained pShuttle-E1A positive clones were confirmed by PCR with P1 and P2. The results were shown in FIG. 2 and the construction process was shown in FIG. 3. The obtained positive clones were sequenced, and the sequencing results were completely consistent with the corresponding sequences on the AD5 genomic DNA.

Figure 4:
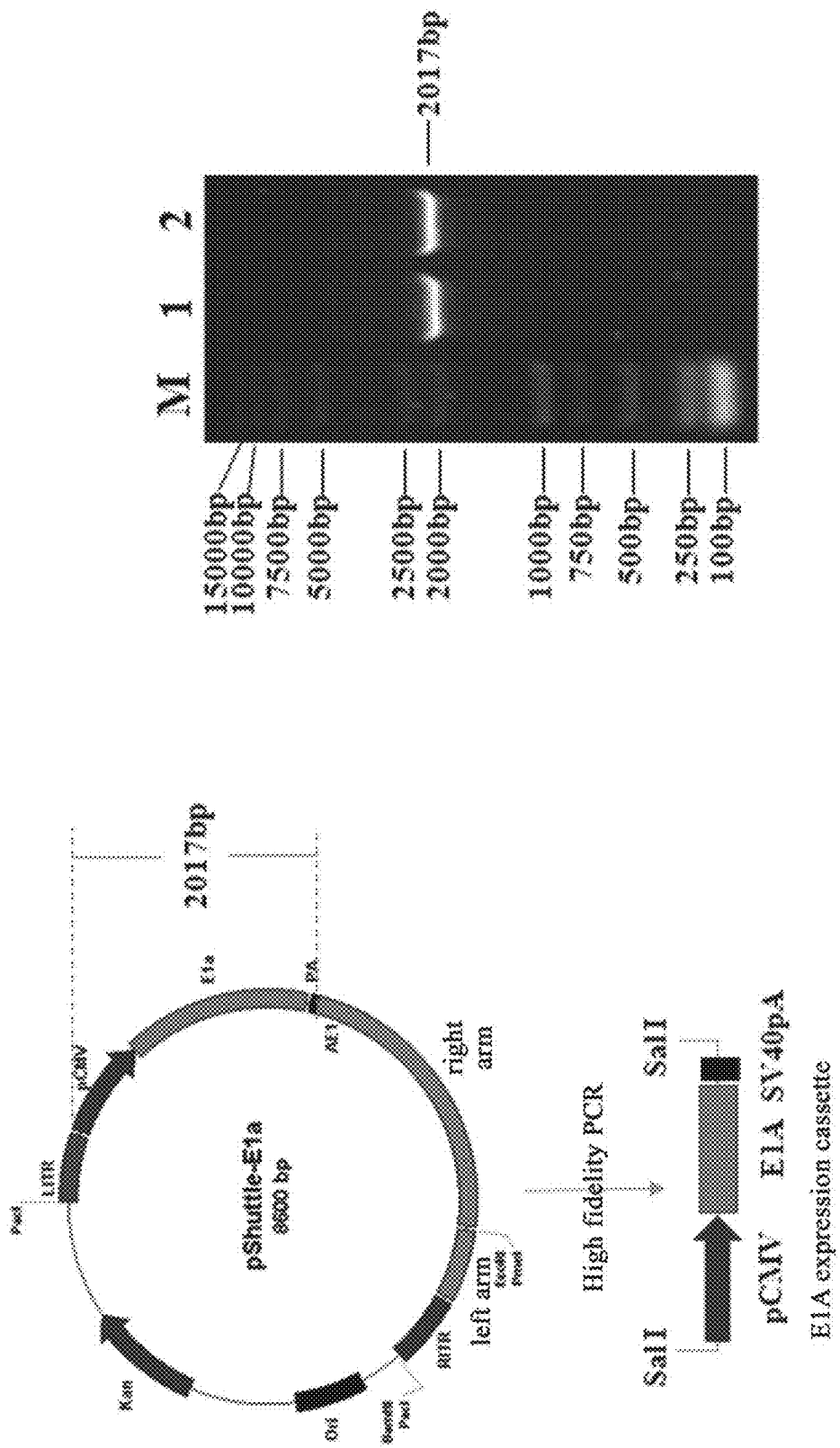
FIG. 4 shows the schematic diagram (left) and gel electrophoresis image (right) of the E1A expression cassette amplified by PCR from the pShuttle-E1A plasmid; wherein lane M is the DNA molecular weight marker and lanes 1-2 are PCR products.

PCR primers P3 and P4 (P3: CGC GTCGAC TACTGTAATAGTAATCAATTACGG (SEQ ID No. 3) and P4: GAC GTCGAC TAAGATACATTGAT-GAGTTTGGAC (SEQ ID No. 4); Note: The 5'end of each primer is added with a SalI restriction site, which is underlined) were further designed, and the obtained pShuttle-E1A positive clone was used as a template for high-fidelity PCR amplification. The PCR product contains the E1A expression cassette including the CMV promoter, E1A gene fragment, and SV40polyA. The size of the PCR product is 2017 bp (FIG. 4).

Figure 5:
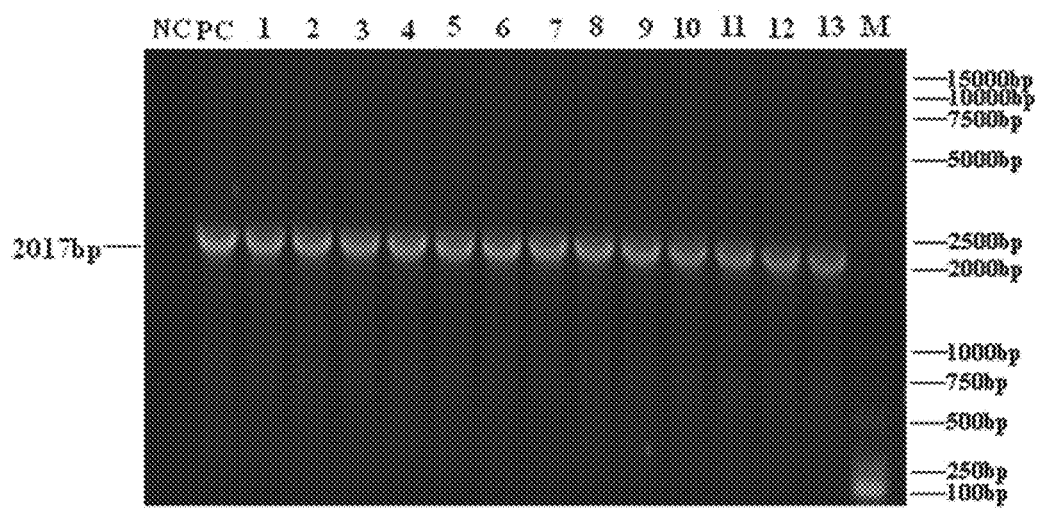
FIG. 5 shows the PCR screening results of the candidates of pShuttle-MCS-E1A plasmid; wherein lane M is molecular weight marker, lanes 1-13 are candidate plasmids, and lane NC is a negative control of the PCR system (i.e. PCR product amplified by using water as template), Lane PC is a positive control of the PCR system (i.e. the template is pShuttle-E1A plasmid DNA containing the fragment of interest).
Figure 6:
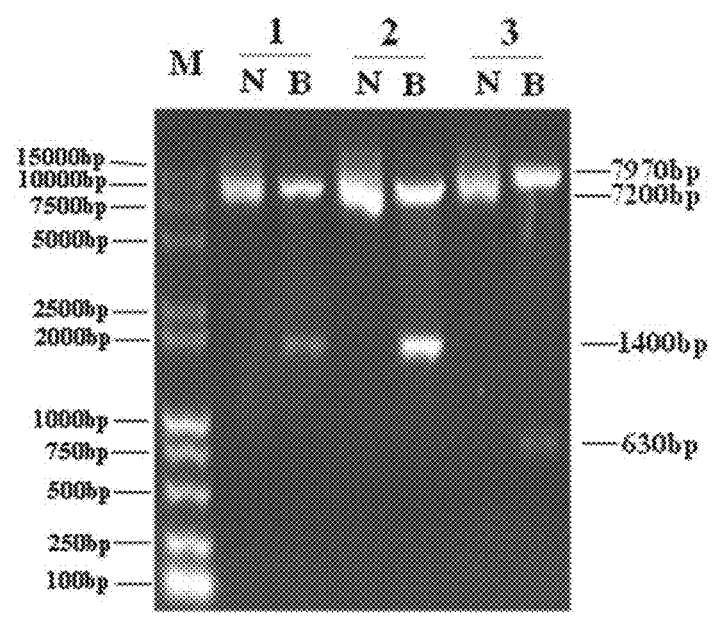
FIG. 6 shows the identification results of the candidates of pShuttle-MCS-E1A plasmid after digested with BglII; wherein lane M is molecular weight marker, samples 1-3 are candidate plasmids, and each sample has two lanes: lane N is an undigested candidate plasmid, and lane B is a candidate plasmid after digestion with BglII.
Figure 7:
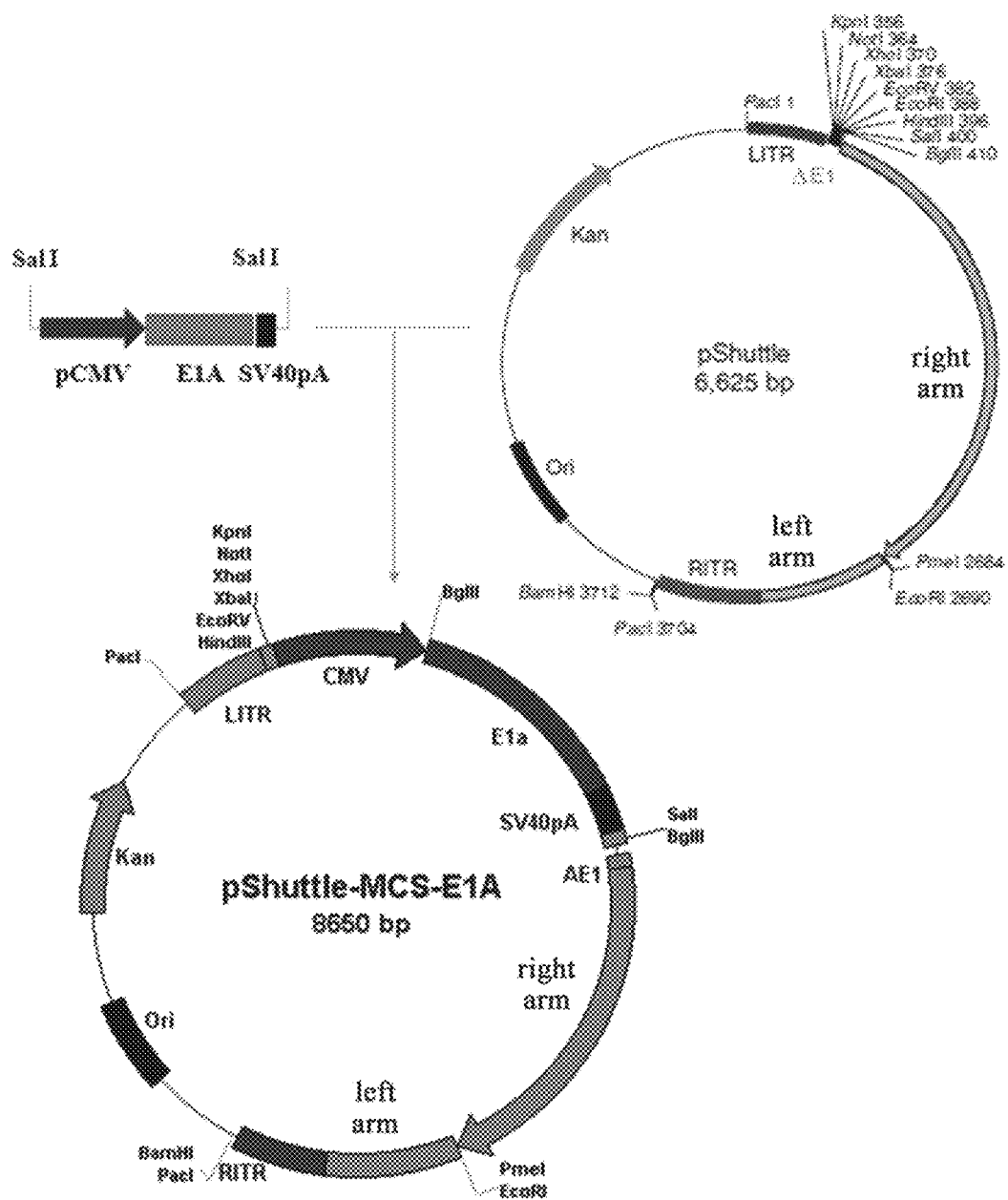
FIG. 7 shows the construction process of pShuttle-MCS-E1A plasmid and a map of the constructed plasmid.

The obtained PCR product of the E1A expression cassette was digested with SalI and cloned into the SalI site of the MCS region on the pShuttle vector (purchased from Agilent). The positive clones inserted with the E1A expression cassette were screened by PCR with primers P3 and P4 (FIG. 5), and confirmed by digestion with BglII. The clone with the forward inserted E1A expression cassette will generate 7200 bp and 1400 bp fragments after BglII enzyme digestion, and the clone with the reverse inserted E1A expression frame will generate 7970 bp and 630 bp fragments after BglII enzyme digestion (FIG. 6). Plasmid #2 in FIG. 6 was selected for subsequent experiments. The intermediate vector pShuttle-MCS-E1A was finally obtained, and the construction process is shown in FIG. 7. The obtained pShuttle-MCS-E1A positive clone was sequenced, and the result was completely consistent with the expected sequence.

Preparation Example 2: Construction of shRNA Expression Vector

Three shRNA sequences (shPDL1-1 (also referred to as shPDL1-#1), shPDL1-2 (also referred to as shPDL1-#2), and shPDL1-3 (also referred to as shPDL1-#3), which are SEQ ID NO. 16, SEQ ID NO. 19, and SEQ ID NO. 22, respectively) targeting, respectively, three regions of 168-190, 430-452 and 589-611 of the mRNA of the coding region of PDL1 were designed based on the human PDL1 variant1 sequence (ACCESSION: NM_014143) in the Genbank on the NCBI website. In addition, a negative control sequence shPDL1-NC which is unrelated to the human PDL1 mRNA was designed. The sequences are as follows:

(1) shPDL1-1
synthetic sense sequence
(SEQ ID NO. 14):
5'-CACCGGGAAATGGAGGATAAGAACATTCAAGAGATGTTCTTATCCTCCATTTCCCTTTT TTG-3' synthetic antisense sequence
(SEQ ID NO. 15):
5'-AGCTCAAAAAAGGGAAATGGAGGATAAGAACATCTCTTGAATGTTCTTATCCTCCATTT CCC-3' shRNA DNA
(SEQ ID NO. 16):
GGGAAATGGAGGATAAGAACATTCAAGAGATGTTCTTATCCTCCATTTCCCTT (2) shPDL1-2
synthetic sense sequence
(SEQ ID NO. 17):
5'-CACCGGATCCAGTCACCTCTGAACATTCAAGAGATGTTCAGAGGTGACTGGATCCTTT TTTG-3' synthetic antisense sequence
(SEQ ID NO. 18):
5'-AGCTCAAAAAAGGATCCAGTCACCTCTGAACATCTCTTGAATGTTCAGAGGTGACTG GATCC-3' shRNA DNA
(SEQ ID NO. 19):
GGATCCAGTCACCTCTGAACATTCAAGAGATGTTCAGAGGTGACTGGATCCTT (3) shPDL1-3
synthetic sense sequence
(SEQ ID NO. 20):
5'-CACCGAGAATCAACACAACAACTAATTCAAGAGATTAGTTGTTGTGTTGATTCTCTTTT TTG-3'

Synthetic antisense sequence
(SEQ ID NO. 21):
5'-AGCTCAAAAAAGAGAATCAACACAACAACTAATCTCTTGAATTAGTTGTTGTGTTGATT CTC-3' shRNA DNA
(SEQ ID NO. 22):
GAGAATCAACACAACAACTAATTCAAGAGATTAGTTGTTGTGTTGATTCTCTT (4) shPDL1-NC
Synthetic NC sense sequence
(SEQ ID NO. 23):
5'-CACCGTTCTCCGAACGTGTCACGTCAAGAGATTACGTGACACGTTCGGAGAATTTTTTT G-3'

Synthetic NC antisense sequence
(SEQ ID NO. 24):
5'-AGCTCAAAAAATTCTCCGAACGTGTCACGTAATCTCTTGACGTGACACGTTCGGAGAA C-3' shNC DNA
(SEQ ID NO. 25):
GTTCTCCGAACGTGTCACGTCAAGAGATTACGTGACACGTTCGGAGAATT

The four sequences were linked to pSGU6/GFP/Neo vector (available from Shanghai Sangon Biotech Co., Ltd.) between BbsI and HindIII sites using cohesive ends complementary to BbsI and HindIII respectively at both ends of the shRNA sequence. As a result, four vectors (pSGU6/GFP/Neo-shPDL1-NC, pSGU6/GFP/Neo-shPDL1-1, pSGU6/GFP/Neo-shPDL1-2 and pSGU6/GFP/Neo-shPDL1-3) capable of expressing shPDL1 were obtained.

Test Example 1: Detection of Inhibitory Effect of shPDL1

Figure 8:
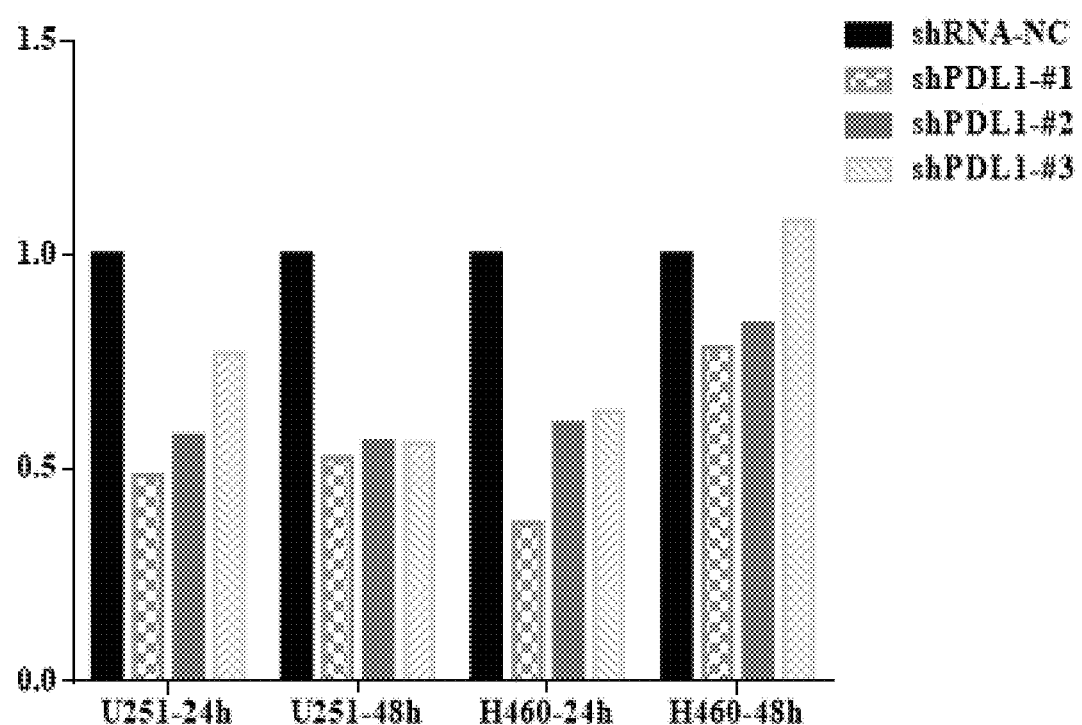
FIG. 8 shows the inhibitory effect of three types of shPDL1 on human PDL1 mRNA in U251 and H460 cells according to an embodiment of the present disclosure. The abscissa axis represents four groups of cell samples collected at 24h and 48h after U251 and H460 cells were treated with four kinds of shRNA, and the ordinate represents the ratio of the expression level of PDL1 mRNA in cells after the cells were treated by each shRNA to the expression level of PDL1 mRNA in cells after the cells is treated by control shRNA.

The inhibitory effect of shPDL1 on hPDL1 mRNA (human PDL1 mRNA) was detected in U251 and H460 cells. U251 and H460 cells were seeded in 12-well plates at $2 \times 10^5$ cells per well, respectively, 12 hours in advance. U251 and H460 cells in each well were transfected with 1.6 μg shRNA expression vector DNA in a ratio of 4 μl lipofectamin 2000. Two cell samples were taken over 24 hours and 48 hours, respectively. After the total RNA was extracted and reverse transcription was performed, the expression level of human PDL1 mRNA in cells was detected by Real-time PCR with the mRNA level of GAPDH gene as a control. The results showed that compared to the control, all of shPDL1-#1, 2, 3 exhibited inhibitory effect on hPDL1 mRNA within a period of time, and wherein shPDL1-#1 had the most significant inhibitory effect on hPDL1 mRNA (FIG. 8).

Figure 9:
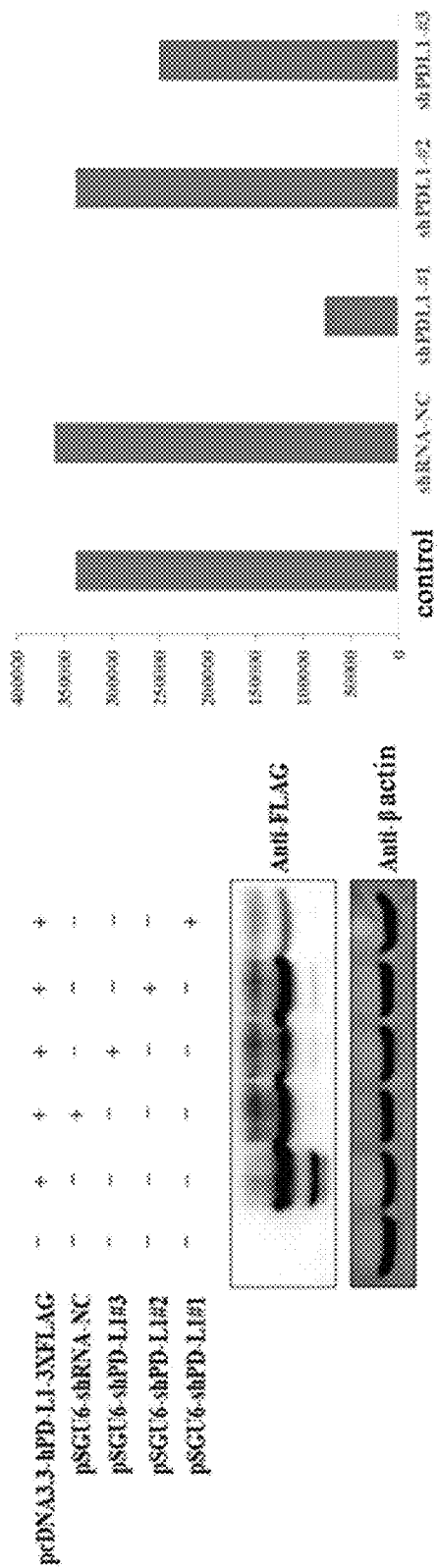
FIG. 9 shows the inhibitory effect of three types of shPDL1 on exogenous hPDL1 expression in 293T cells according to an embodiment of the present disclosure. The left picture is the result of Western Blot, which shows the change of hPDL1 (with FLAG tag) expression in the cell samples and the expression of intracellular protein reference β-actin in cells after treatment with different shPDL1; The right picture shows, based on the result of Western blot, the grayscale scan values of hPDL1 bands using the intracellular protein reference β-actin as a normalized reference. The abscissa represents the groups of 293 cell samples after the samples were treated by different shPDL1. "Control" refers to a control group only transfected with pcDNA3.3-hPDL1-FLAG expressing hPDL1 (containing the FLAG tag). The ordinate is the grayscale scan value of the target protein normalized by β-actin.

In addition, the inhibitory effects of three shPDL1s were also tested at the protein level. 293T cells were transiently transfected with plasmids pSGU6/GFP/Neo-shPDL1-NC, pSGU6/GFP/Neo-shPDL1-1, pSGU6/GFP/Neo-shPDL1-2 and pSGU6/GFP/Neo-shPDL1-3 with pcDNA3.3-hPDL1-3×FLAG at an equimolar ratio (1:1), respectively, wherein plasmid pcDNA3.3-hPDL1-3×FLAG expresses the human PDL1 protein fused with 3×FLAG tag. Cell samples were collected after 48 hours, and Western blot analysis was performed after cell lysis. The results demonstrated that shPDL1-#1 can significantly reduce the over-expressed hPDL1 (see FIG. 9).

The construction process of the pcDNA3.3-hPDL1-3×FLAG plasmid was as follows: First, two primers (P11: CGCGTCGACATGAGGATATTTGCTGTCTTTAT (SEQ ID No. 11), P12: CCGCTCGAGCGTCTCCTCCAAATGTGTATCAC (SEQ ID No. 12)) were designed based on the mRNA sequence of the human PDL1 gene in NCBI. The total RNA of U251 cells was extracted by Trizol and was used as a template to perform RT-PCR to obtain hPDL1 cDNA, which was then cloned into the pShuttle-IRES-hrGFP-1 vector (purchased from Agilent), so that the hPDL1 was expressed in fusion with FLAG tag downstream thereto to obtain an intermediate vector pShuttle-HPDL1-IRES-hrGFP-1. Another primer (P15: CGCCTATTACACCCACTCGTGCAG (SEQ ID No. 13)) was designed and was used together with primer P11 to amplify a sequence including hPDL1 cDNA-FLAG-IRES-hrGFP in the pShuttle-hPDL1-IRES-hrGFP-1. Then the fragment was cloned into pcDNA3.3-TOPO vector (purchased from Invitrogen) to obtain pcDNA3.3-hPDL1-FLAG vector. The inserted fragment was sequenced and being confirmed that the sequence was completely correct.

Preparation Example 3: Preparation of Genomic DNA of Oncolytic Adenovirus (OAd-shPDL1)

Figure 10:
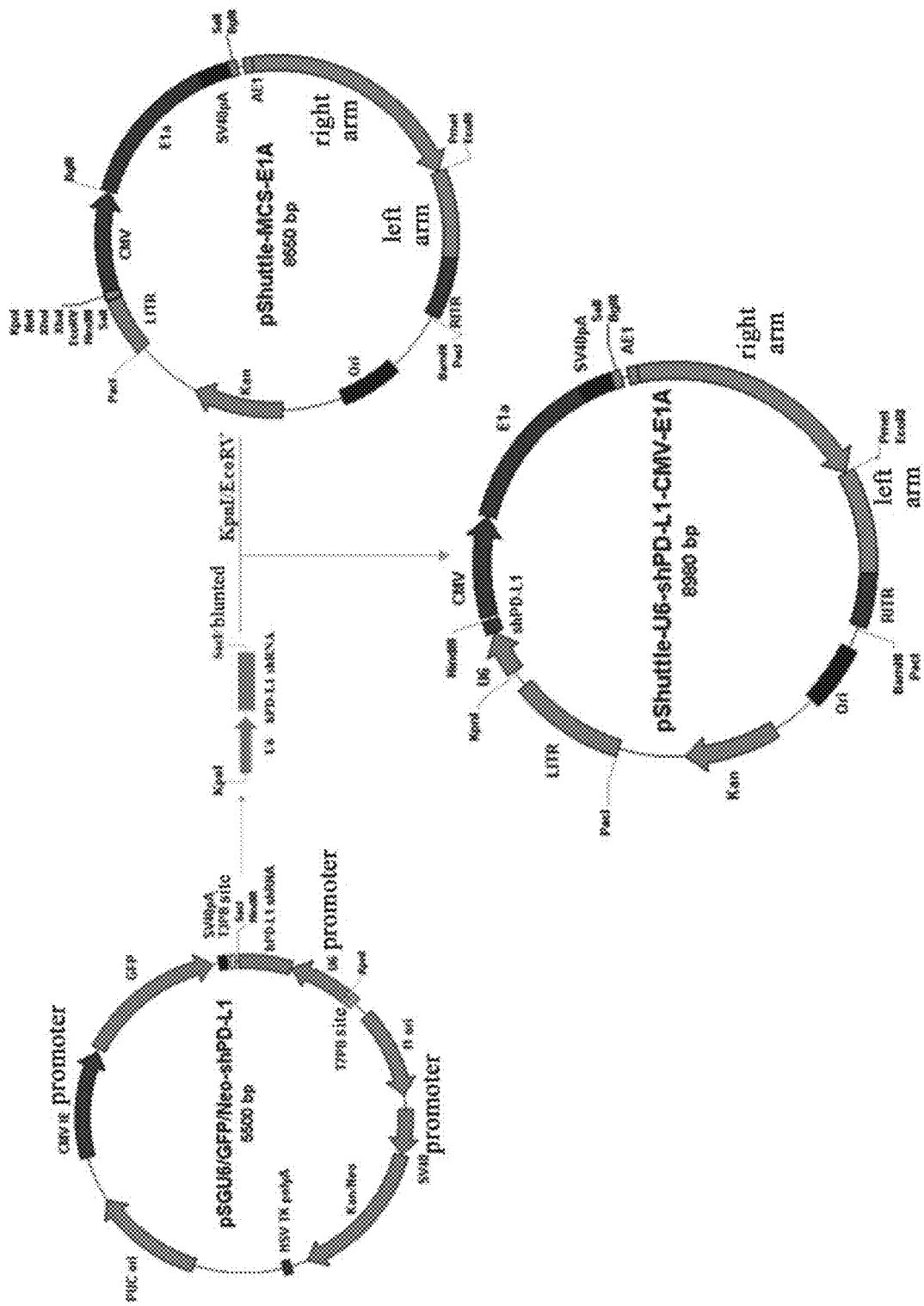
FIG. 10 shows the construction process of pShuttle-U6-shPDL1-CMV-E1A plasmid and a map of the constructed plasmid.
Figure 11:
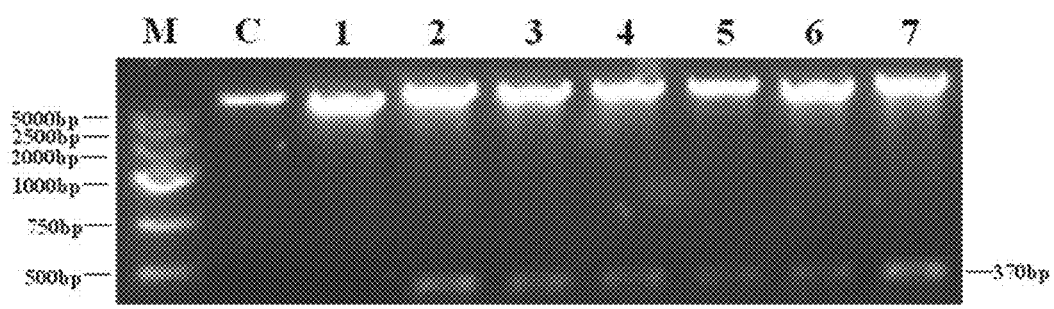
FIG. 11 shows the identification results of pShuttle-U6-shPDL1-CMV-E1A plasmid after digestion; wherein lane M is molecular weight marker, lane C is a control plasmid after digestion with KpnI/HindIII (pShuttle-MCS-E1A), and lanes 1-7 are candidate plasmids after digestion with KpnI/HindIII.

1. After the inhibitory effect of shPDL1 was confirmed, a coding frame including U6 promoter and the whole sequence of shPDL1 were cloned into pShuttle-MCS-E1A vector. The pSGU6/GFP/Neo-shPDL1 vector was digested with SacI and the cohesive end formed thereby was digested with T4 DNA polymerase to obtain blunt end. Then, precipitation and recovery were performed using ethanol/ammonium acetate. The coding frame sequence including U6 promoter and shPDL1 sequence was recovered after digestion with KpnI; simultaneously pShuttle-MCS-E1A vector was digested by KpnI and EcoRV and recovered. Finally, three shPDL1 coding frames were linked to the pShuttle-MCS-E1A vector, respectively, to obtain the final vector pShuttle-U6-shPDL1-CMV-E1A, as shown in FIG. 10. Several colonies were selected for plasmid extraction and identified by KpnI/HindIII digestion. Correct clone will produce a band of 370 bp (see FIG. 11). The correct pShuttle-U6-shPDL1-CMV-E1A plasmids were selected for sequencing. The results showed that the sequences were completely correct.

Figure 12:
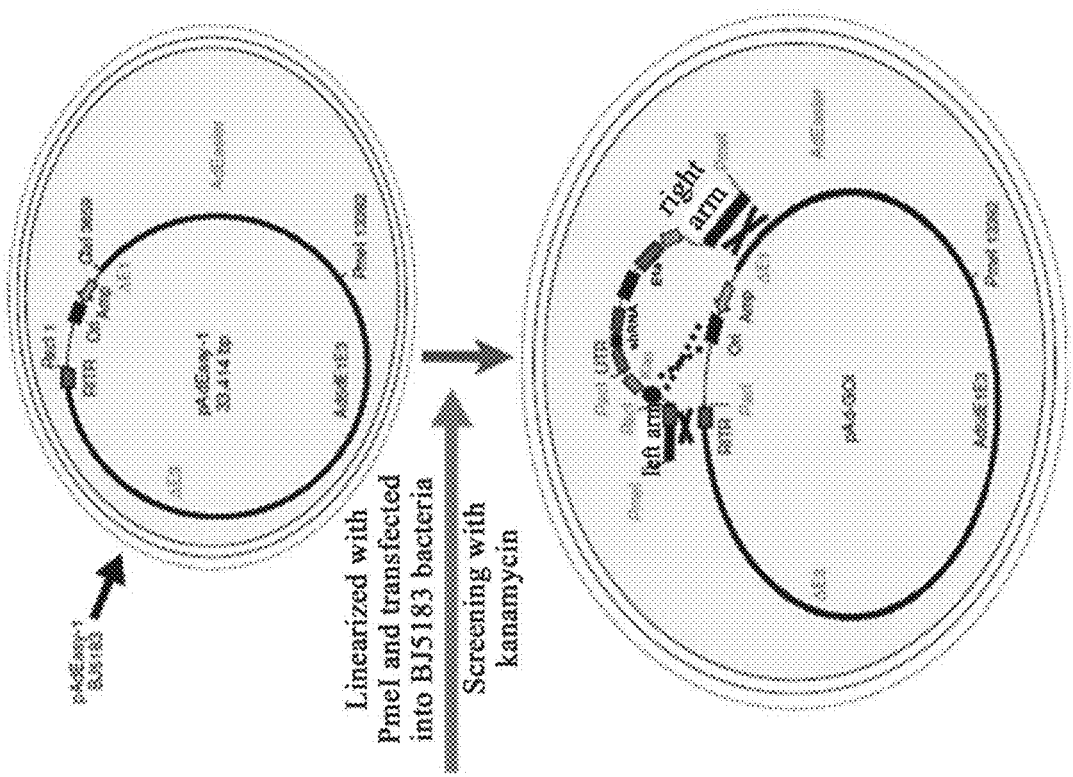
FIG. 12 shows a schematic diagram of the process of homologous recombination between pShuttle-U6-shPDL1-CMV-E1A plasmid and pAdEasy-1 in BJ5183 bacteria.
Figure 12:
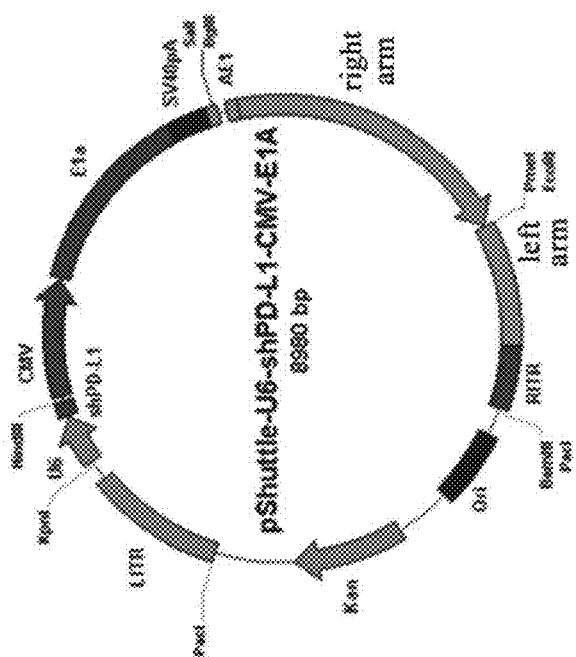

2. Four plasmids pShuttle-MCS-E1A (control plasmid), pShuttle-U6-shPDL1-1-CMV-E1A, pShuttle-U6-shPDL1-2-CMV-E1A and pShuttle-U6-shPDL1-3-CMV-E1A were digested with PmeI to get linearization and were transfected into BJ5183 strains, in which homologous recombination was performed between the transfected plasmid and pAdEasy-1 plasmid (purchased from Agilent) which contains AD5 adenovirus genomic DNA (lack of E1 and E3 regions). Therefore, CMV-E1A-SV40 pA expression cassette and/or U6-shPDL1 coding frame were integrated into the genomic DNA of the adenovirus AD5, so as to obtain the genomic DNA of oncolytic adenovirus (OAd-shPDL1) that can express the gene of interest and can replicate (FIG. 12).

The specific experimental process is as follows:

(1) Preparation of BJ5183 Competent Cells.

BJ5183 strains (which has been transferred into pAdEasy-1 plasmid) stored at −80° C. in our laboratory were inoculated in LB/Amp medium, and activated at 37° C. and 200 RPM overnight. BJ5183 competent bacteria were prepared using the Super Competent Cell Preparation Kit (B529303-0040) of Sangon Biotech Co., Ltd. and were subpackaged in 100 μl and stored at −80° C. until use.

(2) Homologous Recombination Between pShuttle-Related Plasmid and pAdEasy-1 Plasmid.

Figure 13:
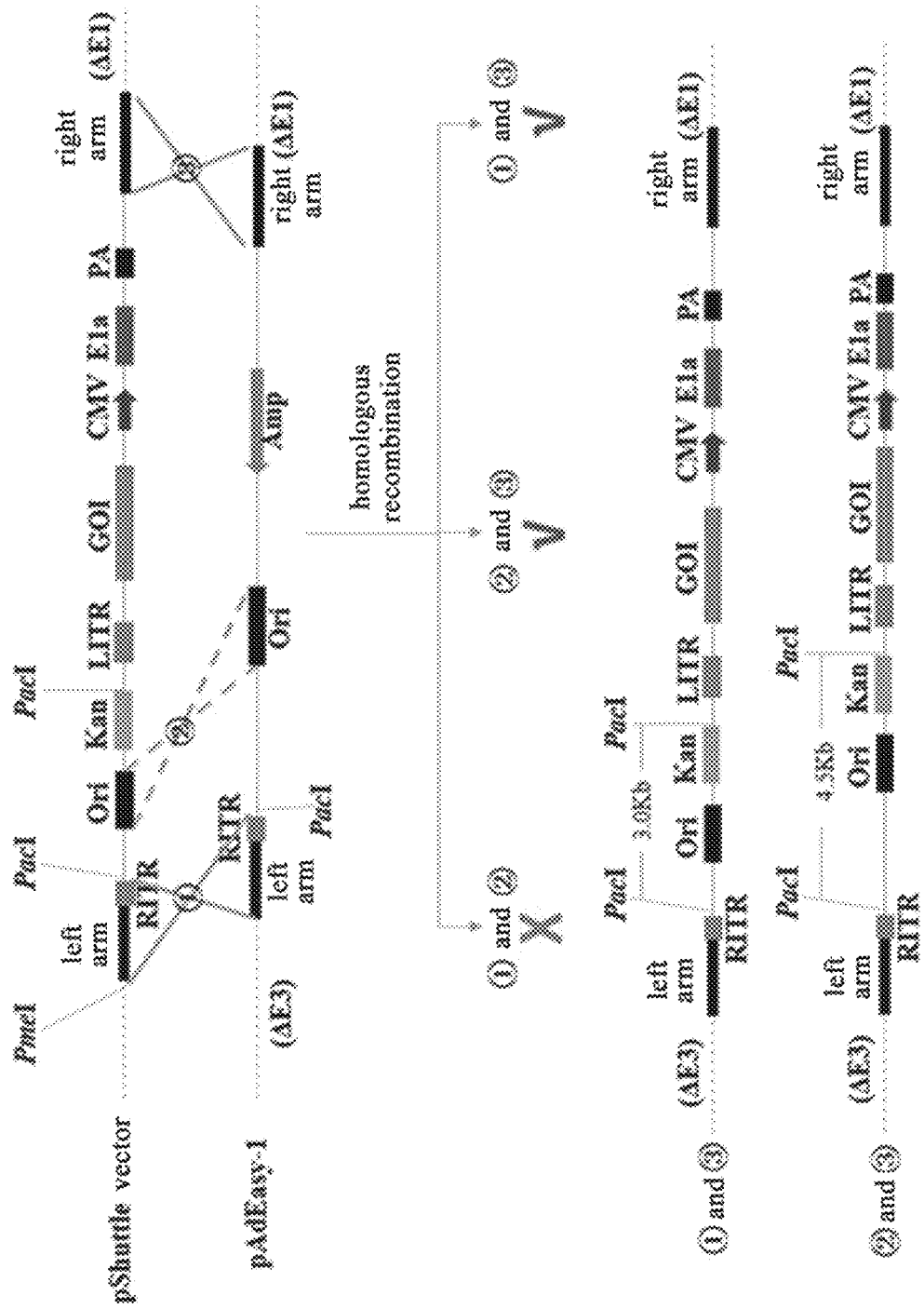
FIG. 13 shows a schematic diagram of the process of homologous recombination between pShuttle-related plasmid and pAdEasy-1 during the construction of pAdEasy-U6-shPDL1-CMV-E1A plasmid.
Figure 14:
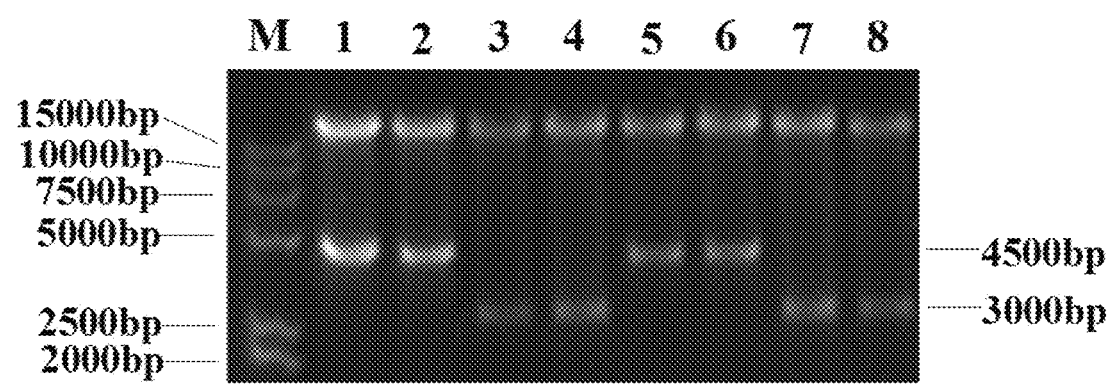
FIG. 14 shows the identification results of the constructed positive pAdEasy-U6-shPDL1-CMV-E1A plasmid after digestion with PacI; wherein lane M is molecular weight marker, and lanes 1-8 are PacI digested products of different plasmids, specifically, lane 1 is PacI digested product of C-4.5K, lane 2 is PacI digested product of 1-4.5K, lane 3 is Pad digested product of C-3K, lane 4 is Pad digested product of 1-3K, lane 5 is PacI digested product of 2-4.5K, lane 6 is PacI digested product of 3-4.5K, lane 7 is PacI digested product of 2-3K, and lane 8 is PacI digested product of 3-3K.

1 μg of plasmid DNA of each pShuttle-MCS-E1A, pShuttle-U6-shPDL1-1-CMV-E1A, pShuttle-U6-shPDL1-2-CMV-E1A and pShuttle-U6-shPDL1-3-CMV-E1A were taken and digested with 1 μl of PmeI, respectively, for 1.5 hours of reaction at 37° C. Then, 1 μl of alkaline phosphatase was added to dephosphorize the linearized DNA fragment. Then the digested product was directly added to 100 μl of BJ5183 competent bacteria for conventional transformation. Finally, the transformed bacterial solution was spread on a Kana-resistant LB plate and cultured at 37° C. overnight. The next day, the colonies appearing on the plate were picked and inoculated in LB/Kana and cultured overnight to extract plasmid DNA and perform conventional PacI digestion. The digested products were analyzed by electrophoresis. Three different modes of homologous recombination may occur depending on the location where homologous recombination occurs (FIG. 13). The plasmids that can produce 4.5 Kb or 3 Kb fragments after digestion with PacI are plasmids that undergo correct homologous recombination. The electrophoresis results of the digested products (FIG. 14) prove that: correct homologous recombination occurred between the pAdEasy-1 plasmid and pShuttle-MCS-E1A, pShuttle-U6-shPDL1-1-CMV-E1A, pShuttle-U6-shPDL1-2-CMV-E1A and pShuttle-U6-shPDL1-3-CMV-E1A, respectively, and genomic DNAs (pAdEasy-U6-shPDL1 #1-CMV-E1A, pAdEasy-U6-shPDL1 #2-CMV- E1A, pAdEasy-U6-shPDL1 #3-CMV-E1A and pAdEasy-CMV-E1A) for packaging oncolytic adenoviruses (all called OAd-shPDL1) and its control virus were successfully obtained. The shPDL1 coding frame and E1A expression cassette inserted in the resulted positive clones were sequenced and were confirmed being completely correct.

Preparation Example 4: Packaging and Amplification of Oncolytic Adenovirus (OAd-shPDL1)

(1) Preparation of Genomic DNA for Packaging Oncolytic Adenovirus (OAd-shPDL1)

2 μg plasmid DNA of each of pAdEasy-CMV-E1A, pAdEasy-U6-shPDL1 #1-CMV-E1A, pAdEasy-U6-shPDL1 #2-CMV-E1A and pAdEasy-U6-shPDL1 #3-CMV-E1A was added with 2 μl PacI enzyme, reacted at 37° C. for 2 hours, followed by precipitation of DNA with ethanol/ammonium acetate, rinsed with 70% ethanol. Then the DNA precipitate was dissolved in 10 μl clean ddH$_2$O, and transfected into AD293 for packaging of the virus.

(2) Packaging of Oncolytic Adenovirus (OAd-shPDL1)

Figure 15:
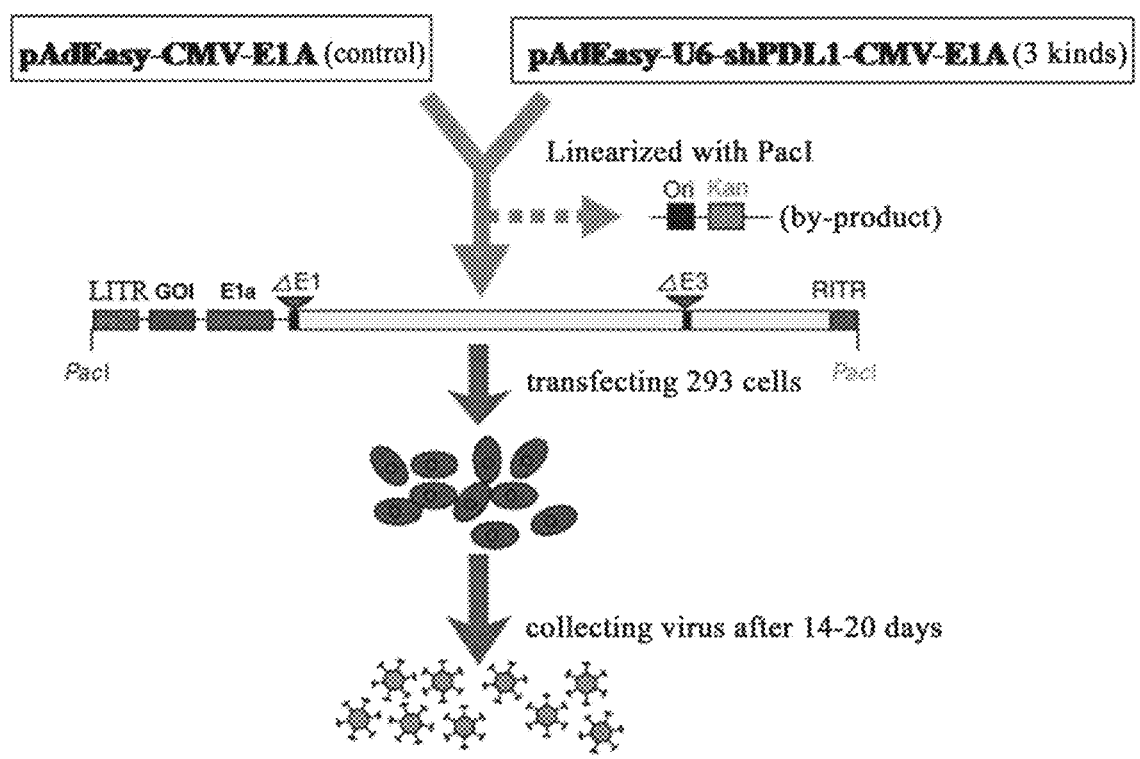
FIG. 15 is a schematic diagram showing the process of virus packaging from the pAdEasy-U6-shPDL1-CMV-E1A plasmids and the pAdEasy-CMV-E1A control plasmid in AD293 cells, respectively.

AD293 cells in well growth were inoculated in a 6-well plate one day in advance, and the number of inoculated cells is preferably for achieving 60-70% of the cell coverage rate when performing transfection on the next day. The prepared linearized DNA (about 2 μg) and Attractene transfection reagent (6 μl) purchased from QIAGEN were mixed uniformly and added into AD293 cells. The mixture was "cross-shaken" and placed into a cell incubator (37° C., 5% CO$_2$) for further culture for about 10-14 days, and the cytopathy is observed every 2-3 days. When a part of cells become "rosary" and gradually expand until a large number of cells fall off, the cells could be gently blown to harvest the cells and the culture supernatant which were stored at −80° C. or directly subjected to further amplification, the process is shown in FIG. 15.

(3) Amplification of Oncolytic Adenovirus (OAd-shPDL1)

Similarly, AD293 cells in well growth were inoculated in a 6 cm cell culture dish one day in advance, and the number of inoculated cells is preferably for achieving 70-80% of the cell coverage rate when carrying out the transfection on the next day. 800-1000 μl of the precedingly collected virus supernatant were added to each 6 cm cell culture dish, and the mixture was mixed in "cross-shaken" for further culture in cell culture medium. Usually, a large number of cells became round and detached after 48 hours, when the cells and culture supernatant could be collected. Subsequently, further amplification of the virus was carried out in 10 cm cell culture dishes and the cell density is preferably about 70% when the virus was inoculated. 1200-1500 ml of the precedingly collected virus supernatant were added to each 10 cm cell culture dish, and the cells and the supernatant were collected after 48 hours when a large number of the cells were found to detach off. Finally, the virus was further amplified in a 15 cm culture dish, and 2 ml of virus culture supernatant collected in the 10 cm culture dish were added when the cell density is about 70%. After mixing, the cells were further cultured for 48 hours to collect the cells and the culture supernatant. The virus can then be cyclically amplified in the 15 cm culture dish to the desired virus amount.

(4) Determination of Oncolytic Adenovirus (OAd-shPDL1) Titer

The methods for measuring the titer of the adenovirus include VP method, GTU/BFU method, plaque method, TCID50 method and Hexon staining (kit) method. TCID50 method and Hexon staining method are more accurate and have high repetition rate. In this example, the number of active virus particles (unit: PFU/ml) in the obtained virus supernatant was measured by Hexon staining method. The results are shown below. Three kinds of pShuttle-U6-shPDL1-CMV-E1A plasmids described in the present disclosure and one kind of control plasmid pShuttle-MCS-E1A were homologously recombined with pAdEasy-1 plasmid to generate six kinds of pAdEasy-U6-shPDL1-CMV-E1A plasmids and two kinds of pAdEasy-CMV-E1A (see FIG. 13, each kind of plasmid can carry out homologous recombinations in two correct manners and can obtain two correct plasmids. After digestion with PacI, a band of 4.5K or 3K can be generated respectively). The viruses were packaged in AD293 using the obtained eight kinds of plasmids by homologous recombination to obtain eight kinds of oncolytic viruses: OAd-C-4.5K, OAd-C-3K, OAd-shPDL1 #1-4.5K, OAd-shPDL1 #1-3K, OAd-shPDL2 #1-4.5K, OAd-shPDL1 #2-3K, OAd-shPDL1 #3-4.5K and OAd-shPDL1 #3-3K, which are respectively abbreviated as follows: C-4.5K, C-3K, 1-4.5K, 1-3K, 2-4.5K, 2-3K, 3-4.5K and 3-3K. Among them, C-4.5K and C-3K are the same virus with same sequence, 1-4.5K and 1-3K are the same virus with same sequence, 2-4.5K and 2-3K are the same virus with same sequence, and 3-4.5K and 3-3K are the same virus with same sequence.

| titer of obtained viruses: | | |
|---|---|---|
| control oncolytic viruses: | OAd-C-4.5K | 2.91*10$^8$ PFU/ml |
| | OAd-C-3K | 2.3*10$^8$ PFU/ml |
| oncolytic viruses (Oad-shPDL1): | OAd-shPDL1#1-4.5K | 1.58*10$^8$ PFU/ml |
| | OAd-shPDL1#1-3K | 2.06*10$^8$ PFU/ml |
| | OAd-shPDL1#2-4.5K | 2.06*10$^8$ PFU/ml |
| | OAd-shPDL1#2-3K | 1.94*10$^8$ PFU/ml |
| | OAd-shPDL1#3-4.5K | 1.58*10$^8$ PFU/ml |
| | OAd-shPDL1#3-3K | 1.94*10$^8$ PFU/ml |

Example 1: Replication Capacity of Oncolytic Adenoviruses (OAd-shPDL1) in Cells (Tumor Cells and Normal Cells)

Figure 16:
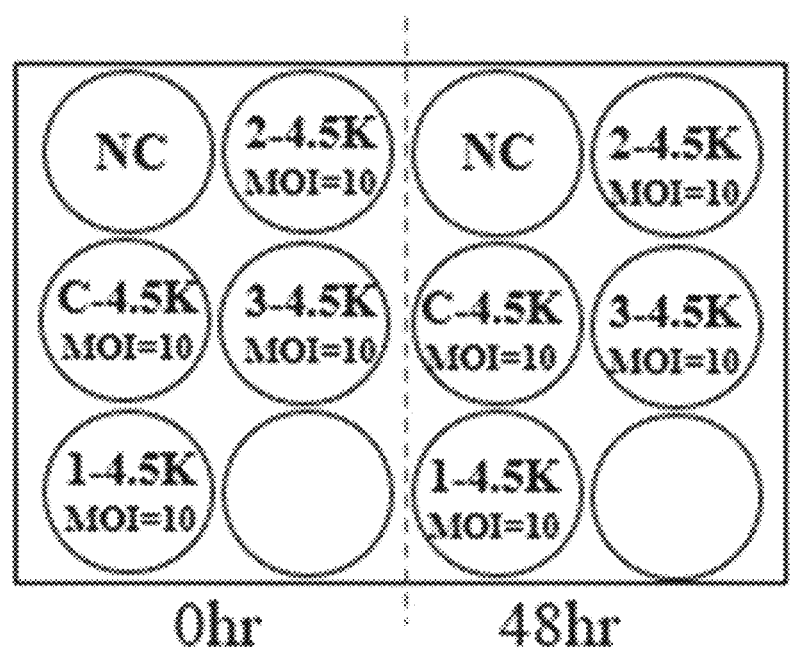
FIG. 16 shows a schematic diagram of sample arrangement in a 12-well plate according to an embodiment of the present disclosure. As shown in the figure, cells were treated with OAd-shPDL1 #1-4.5K (1-4.5K), OAd-shPDL1 #2-4.5K (2-4.5K), OAd-shPDL1 #3-4.5K (3-4.5K) and control oncolytic virus OAd-C-4.5K (C-4.5K) in indicated MOI values, respectively. Wherein, "NC" means a blank control group without any virus treatment.

Cells (HUVEC, MRC-5, Hela, A549, and U251) were seeded in 12-well plates in an amount of 1.5×10$^5$ cells per well, and the volume of culture medium (HUVEC cells were cultured in Allcells dedicated medium. Both the cells and the medium were purchased from Aussels Biotechnology (Shanghai) Co., Ltd.; MRC-5 cells were cultured in MEM+10% FBS medium; Hela cells were cultured in RPMI1640+10% FBS medium; A549 cells were cultured in DMEM/F12+10% FBS medium; U251 cells were cultured in MEM+10% FBS. All of mediums were purchased from Gibco Co., Ltd.) was 1 ml. After 12 hours, the medium was removed and the cells were rinsed once with PBS, and 500 μl of virus suspension (prepared by preparation example 4) were added with a virus multiplicity of infection (MOI) of 10 as shown in FIG. 16. After the viruses were incubated together with the cells for 90 minutes, the virus suspension was removed, and the cells were rinsed twice with PBS. This time point is deemed as 0 hour and a portion of cell sample was taken by trypsinization. Another portion of cell sample was taken after 48 hours. Genomic DNA of cell samples harvested at 0 hour and 48 hours were extracted, respectively, and Q-PCR was performed using specific primers for the adenoviruses type 5 E1A gene (P5: TCCGGTTTCTATGC-CAAACCT (SEQ ID No. 5) and P6: TCCTCCGGTGA-TAATGACAAGA (SEQ ID No. 6)), Hexon gene (P7:

CCATTACCTTTGACTCTTGTGT (SEQ ID No. 7) and P8: GGTAGTCCTTGTATTTAGTATC (SEQ ID No. 8)), and human GAPDH gene (P9: CATGCCTTCTTGCCTCTTGTCTCTTAGAT (SEQ ID No. 9) and P10: CCATGGGTGGAATCATATTGGAA-CATGTAA (SEQ ID No. 10)). The replication capacity of viruses in cells after the viruses infecting the cells for 48 hours was analyzed based on the Q-PCR results. A comparison of the replication capacity of oncolytic adenoviruses (OAd-shPDL1) in different cells was as shown in FIG. 17.

Figure 17:
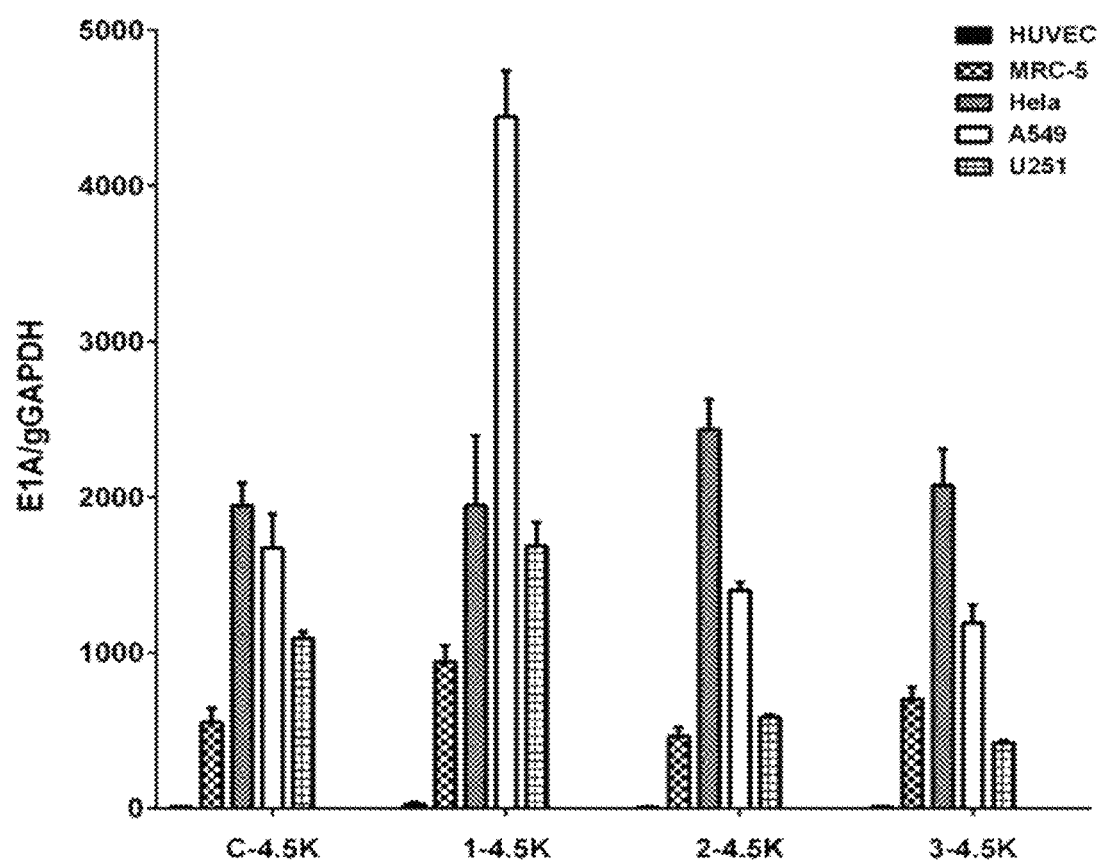
FIG. 17 shows the comparison results of replication in different cells of the oncolytic viruses OAd-shPDL1 (OAd-shPDL1 #1-4.5K (1-4.5K), OAd-shPDL1 #2-4.5K (2-4.5K) and OAd-shPDL1 #3-4.5K (3-4.5K)) constructed according to the present disclosure in Example 1, wherein OAd-C-4.5K (C-4.5K) was used as a system control virus. The abscissa represents different groups of oncolytic virus, and the ordinate represents multiples of the copy number of oncolytic adenovirus-specific gene E1A using the GAPDH gene in the cells as a normalized reference.
Figure 18:
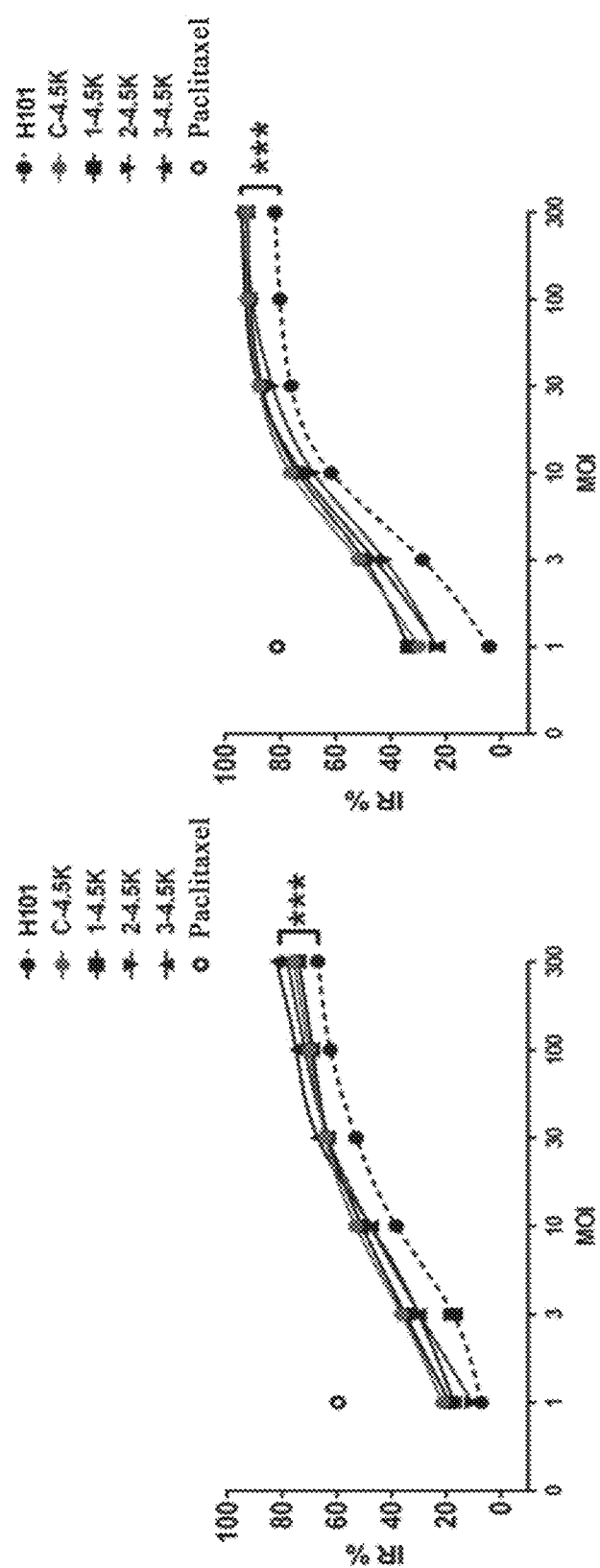
FIG. 18 shows the killing effect on U251 cells of the oncolytic viruses OAd-shPDL1 (OAd-shPDL1 #1-4.5K (1-4.5K), OAd-shPDL1 #2-4.5K (2-4.5K) and OAd-shPDL1 #3-4.5K (3-4.5K)), and system control virus OAd-C-4.5K (C-4.5K) constructed according to the present disclosure, as well as control group H101 and control group Paclitaxel in Example 2. The abscissa represents different virus infection dose (unit: MOI) used to treat the cells, and the ordinate represents the inhibition rate (%) on the cell growth after cells were treated with virus. The left picture shows the results of the 48-hour experiment, and right picture shows the results of the 72-hour experiment. "***" indicates p<0.001.
Figure 19:
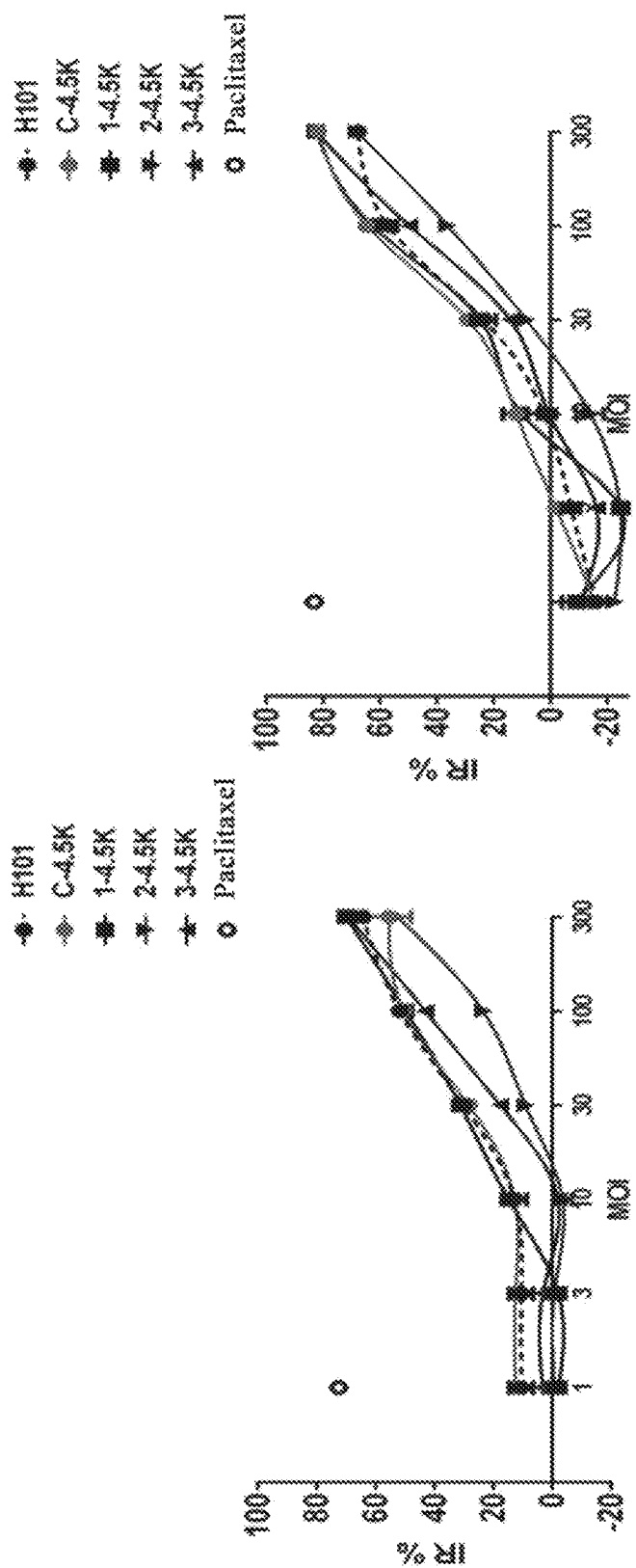
FIG. 19 shows the killing effect on A549 cells of the oncolytic viruses OAd-shPDL1 (OAd-shPDL1 #1-4.5K (1-4.5K), OAd-shPDL1 #2-4.5K (2-4.5K) and OAd-shPDL1 #3-4.5K (3-4.5K)), and system control virus OAd-C-4.5K (C-4.5K) constructed according to the present disclosure, as well as control group H101 and control group Paclitaxel in Example 2. The abscissa represents different virus infection dose (unit: MOI) used to treat the cells, and the ordinate represents the inhibition rate (%) on the cell growth after cells were treated with virus. The left picture shows the results of the 48-hour experiment, and right picture shows the results of the 72-hour experiment.
Figure 20:
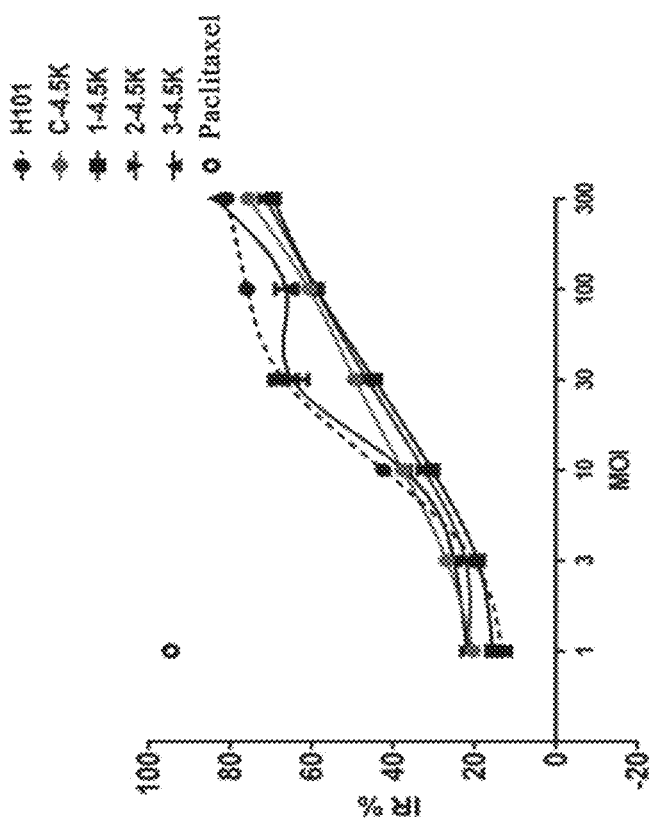
FIG. 20 shows the killing effect on Hela cells of the oncolytic viruses OAd-shPDL1 (OAd-shPDL1 #1-4.5K (1-4.5K), OAd-shPDL1 #2-4.5K (2-4.5K) and OAd-shPDL1 #3-4.5K (3-4.5K)), and system control virus OAd-C-4.5K (C-4.5K) constructed according to the present disclosure, as well as control group H101 and control group Paclitaxel in Example 2. The abscissa represents different virus infection dose (unit: MOI) used to treat the cells, and the ordinate represents the inhibition rate (%) on the cell growth after cells were treated with virus. The left picture shows the results of the 48-hour experiment, and right picture shows the results of the 72-hour experiment.
Figure 20:
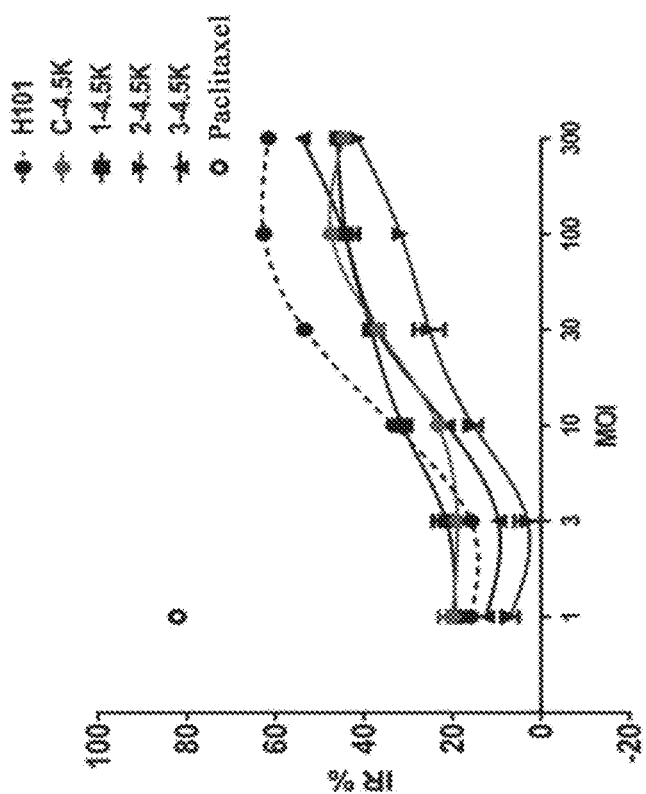
Figure 21:
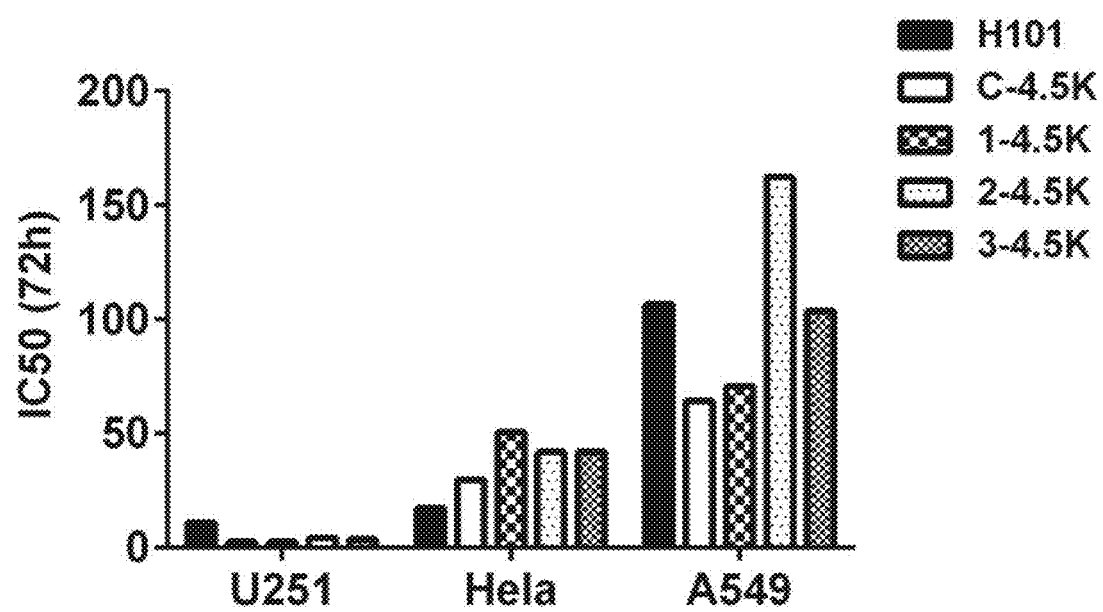
FIG. 21 shows the comparison results of the $IC_{50}$ (72 h) doses against different cells of oncolytic viruses OAd-shPDL1 (OAd-shPDL1 #1-4.5K (1-4.5K), OAd-shPDL1 #2-4.5K (2-4.5K) and OAd-shPDL1 #3-4.5K (3-4.5K)) and the system control virus OAd-C-4.5K (C-4.5K) constructed according to the present disclosure, as well as the control group H101 in Example 2. The abscissa represents different types of tumor cell groups, and the ordinate represents the number of viruses (unit: MOI) that can kill 50% of the corresponding tumor cells when the cells were incubated with the viruses for 72 hours.

The results shown in FIG. 17 indicated that the four kinds of oncolyticic adenoviruses (control virus C-4.5K, OAd-shPDL1 virus 1-4.5K, 2-4.5K and 3-4.5K) constructed according to the present disclosure had different replication capacity in the tested cells. The oncolytic viruses according to the present disclosure exhibited very strong replication capacity in the tested tumor cells, and also exhibited strong replication capacity in the immortalized human embryonic lung fibroblast cell line. However, they exhibited very low replication capacity in the human primary cell HUVEC. The replication capacity in human normal cells is about 42-444 times lower than that in tumor cell lines or cell line with tumor forming tendency (such as the immortalized human embryonic lung fibroblast cell line MRC5). Therefore, it is believed that the oncolytic adenoviruses of the present disclosure show strong tumor cell preference in the aspect of selective replication and thus have higher safety in the future clinical application and more improving space in the use amount of the virus.

Example 2: Killing Ability of Oncolytic Adenoviruses (OAd-shPDL1) on Tumor Cells In this example, the killing ability of the oncolytical adenoviruses (OAd-shPDL1) according to the present disclosure was tested through a CCK8 assay. Cells (U251, Hela and A549) were seeded into a 96-well plate at $1.5 \times 10^3$ cells per well and the volume of culture medium (U251 cells were cultured in MEM+10% FBS; Hela cells were cultured in medium RPMI1640+10% FBS; A549 cells were cultured in medium DMEM/F12+10% FBS; All mediums were purchased from Gibco Co., Ltd) in each well is 100 μl. After 12 hours, 50 μl of the medium was removed and 50 μl of a mixture of virus (control virus C-4.5K, OAd-shPDL1 viruses 1-4.5K, 2-4.5K, and 3-4.5K prepared in preparation example 4, respectively) and pure medium was added (this time point was recorded as 0 hour) with a multiplicity of infection (MOI) of 1, 3, 10, 30, 100, and 300, respectively. Three duplicates for each MOI. 10 μl of CCK8 (purchased from DOJINDO chemical science Co., Ltd.) were added at time points of 48 hours and 72 hours. The absorbance value of the culture at 450 nm was measured after 1 hour of incubation. The killing ability of different viruses on cells was determined according to the obtained absorbance value. Commercial oncolytic adenovirus H101 was used as a control. The same cells were treated with the same MOI of viruses in the experiment and the absorbance values were measured at the same time point. In addition, 1 μM of paclitaxel solution was used as a system positive control. The killing effect depending on the dose of the oncolytic adenoviruses (OAd-shPDL1) on three kinds of tumor cell and the half-killing dose ($IC_{50}$) were shown in FIGS. 18-21.

The results showed that the killing effect of the oncolyticic adenoviruses (control virus C-4.5K, OAd-shPDL1 viruses 1-4.5K, 2-4.5K and 3-4.5K) on U251, A549 and Hela cells exhibited significant dose dependence. Compared to commercial oncolyticic adenovirus H101, the oncolytic adenoviruses according to the present disclosure showed similar killing effects and the killing effects on U251 cells were even better than that of the H101, which had significant differences by the statistical analysis of the killing effect. In addition, by comparing the half-killing dose ($IC_{50}$) of the oncolytic viruses of the present disclosure on different cells at 72 h, it is found that the $IC_{50}$ of the oncolytic viruses on human glioma cells U251 is the lowest, which indicates that the oncolytic viruses may have more important clinical value in the treatment of human glioma.

Example 3: Efficacy of shPDL1 Expressed by Oncolytic Adenoviruses (OAd-shPDL1)

To facilitate the detection of the efficacy of shPDL1 expressed by the oncolytic adenovirus (OAd-shPDL1) of the present disclosure, two cell lines which can stably express FLAG-tagged hPDL1 were constructed in this example: A549/hPDL1-FLAG and Hela/hPDL1-FLAG. The construction process was briefly described as follows: the pcDNA3.3-hPDL1-FLAG vector (also referred to as pcDNA3.3-hPDL1-FLAG-IRES-hrGFP vector) obtained according to example 2 was transfected into A549 cells and Hela cells by lipofectamin 2000. Since the vector carried a Neomycin gene, G418 was added for screening for three times, and A549/hPDL1-FLAG and Hela/hPDL1-FLAG cell strains capable of stably expressing FLAG-tagged hPDL1 and GFP proteins were finally obtained.

Figure 22:
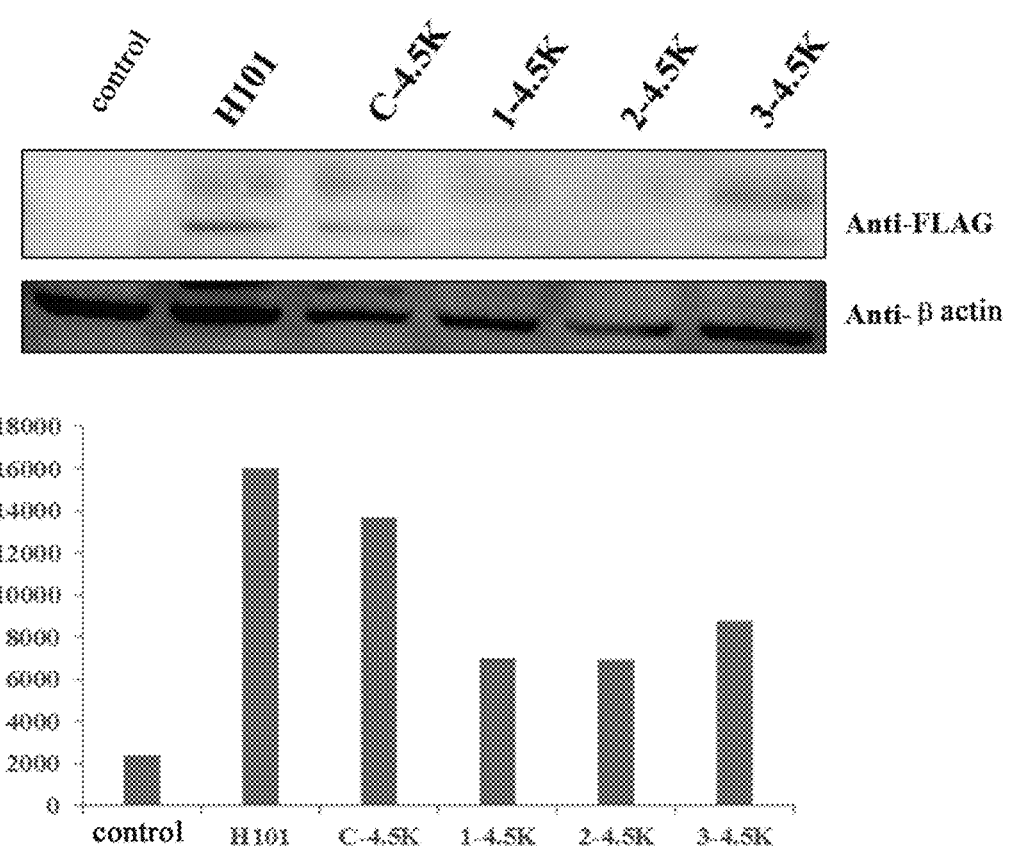
FIG. 22 shows the inhibitory effect on over-expressed hPD-L1 in A549/hPD-L1-FLAG cell strain of oncolytic adenoviruses OAd-shPDL1 (OAd-shPDL1 #1-4.5K (1-4.5K), OAd-shPDL1 #2-4.5K (2-4.5K) and OAd-shPDL1 #3-4.5K (3-4.5K)) and the system control virus OAd-C-4.5K (C-4.5K) constructed according to the present disclosure, as well as the control group H101 in Example 3. The upper picture shows the results of Western blot, which indicates the expression change of hPDL1 (with FLAG tag) in cell samples and the expression of intracellular protein reference β-actin in the cells after the treatment by different viruses. The "control" refers to a blank control group without any virus treatment. The lower picture shows, based on the result of Western blot, the grayscale scan value of hPDL1 band obtained by using the intracellular protein reference β-actin as a normalized reference. The abscissa represents different groups, and the ordinate represents the grayscale scanning value.
Figure 23:
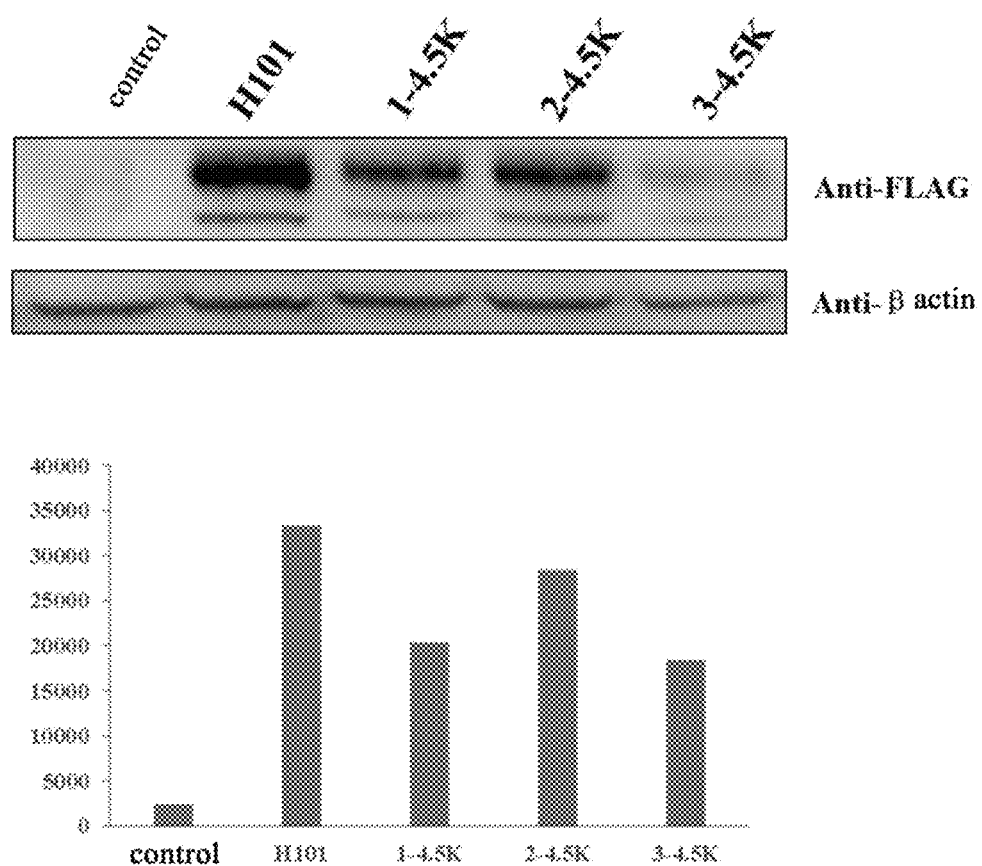
FIG. 23 shows the inhibitory effect on over-expressed hPD-L1 in Hela/hPD-L1-FLAG cell strain of oncolytic adenoviruses OAd-shPDL1 (OAd-shPDL1 #1-4.5K (1-4.5K), OAd-shPDL1 #2-4.5K (2-4.5K) and OAd-shPDL1 #3-4.5K (3-4.5K)) constructed according to the present disclosure, as well as the control group H101 in Example 3. The upper picture shows the results of Western blot, which indicates the expression change of hPDL1 (with FLAG tag) in the cell samples and the expression of intracellular protein reference β-actin in cells after the treatment by different viruses. The "control" refers to a blank control group without any virus treatment. The lower picture shows, based on the result of Western blot, the grayscale scan value of hPDL1 band using the intracellular protein reference β-actin as a normalized reference.

The above two cell lines were treated with H101 and four kinds of oncolytic adenoviruses according to the present disclosure (control virus C-4.5K, OAd-shPDL1 viruses 1-4.5K, 2-4.5K and 3-4.5K prepared in preparation example 4) at a multiplicity of infection (MOI) of 10. Cell samples were harvested at 48 hours after viral infection and subjected to Western blot analysis after lysis to detect the change of expression level of FLAG-tagged hPDL1 using Anti-FLAG antibody. The results were shown in FIGS. 22 and 23. The results of Western blot showed that the expression level of hPDL1 was increased in different extent after the A549 cells and Hela cells were treated with oncolyticic adenovirus. However, the initially increased expression of hPDL1 was inhibited in different extent after the same cells were treated with the three kinds of OAd-shPDL1 oncolytic viruses, respectively. Particularly, OAd-shPDL1-1 (1-4.5K) exhibited the most significant inhibitory effect. The results were consistent with the preceding Q-PCR results and Western blot results after co-transfection.

Preparation Example 5: Ultracentrifugation Purification Procedure of Oncolytic Adenovirus 1) Preparation of a Solution of Oncolytical Adenovirus Before the Ultracentrifugation.

293 cells were infected in a 15CM dish with the adenovirus culture supernatant obtained in Preparation example 4 in a volume ratio of 2:20 of the virus supernatant to the cell culture medium (AD:DMEM=2:20), and were further incubated in a 37° C. and 5% $CO_2$ incubator for about 36 hours. When the cytopathic effect (CPE) of about 50% of the cells was observed under the microscope and the cells were suspended, the cells and culture fluid in the culture dish were collected by blowing or scraping, etc., and stored at 4° C. for a short period of time or stored at −20° C. or −80° C. for a long period of time. In general, the amount of viruses purified by one time ultracentrifugation is the amount of viruses produced by sixty to eighty 15 cm petri dishes (including medium supernatant and infected 293 cells). The collected 293 cells containing the oncolytic virus and the culture supernatant were centrifuged at 3000 RPM for 30 minutes at 4° C. The supernatant and precipitation were subjected to the subsequent experiments respectively. A) The centrifuged supernatant was transferred to a new flask and stored temporarily at 4° C. for virus amplification by infecting cells. By the end of the viral amplification, all supernatants were mixed with PEG8000 solution (aqueous solution of 2.5 M NaCl containing 20% PEG 8000) at a ratio of 2:1 and precipitated on ice for 1 hour or overnight. Then, the supernatant was discarded and the virus precipitate was retained after centrifugation at 12000 RPM for 20 minutes. Finally, the virus precipitate was resuspended in an appropriate amount of 10 mM Tris·Cl (pH 8.0) solution until it was completely dispersed. The virus-containing supernatant was retained after centrifugation at 7000 RPM for 5 minutes, and the virus-containing supernatant was directly loaded into a gradient cesium chloride centrifuge tube for ultracentrifugation. B) The cell precipitate after centrifugation was washed gently (without blowing) with a small amount of 10 mM Tris•Cl (pH 8.0) to wash and remove the medium on the cell surface. The cell precipitate from ten to twelve 15 cm culture dishes was resuspended in 3 ml Tris•Cl and the cell suspension was subpackaged and stored at −20° C. The storage time before the purification is not more than 2 months. After the samples were collected, the cell suspension was thawed in a water bath at 37° C., shaken vigorously for 30 seconds and placed back in a −80° C. refrigerator or placed in a dry ice/pure ethanol mixture to rapidly freeze the cell suspension. The freeze-thaw process was repeated 3-5 times to completely destroy the cell membrane so as to release the virus from the cells to obtain a virus solution. If the virus solution is not purified immediately, it can be stored at −20° C. Before purification by ultracentrifugation, the virus solution obtained in this step is thawed in a water bath at 37° C. and centrifuged at a speed of 16000 RPM at room temperature for 10 minutes. The virus-containing supernatant was collected, which can be temporarily stored on ice for low temperature.

2) AD Virus Purification by Cesium Chloride Density Gradient Centrifugation

Cesium chloride density gradient centrifugation is still the most commonly used method for the isolation and purification of various viruses. It is mainly based on different buoyancy densities of different viruses in the CsCl solution to separates them from other components in the cell lysate. After collecting specific band of the target virus, the PD-10 desalting column was used to remove cesium chloride, and a purified virus was finally obtained. Very high purity of viruses can be obtained using this method. The specific purification procedure is as follows:

1. Preparation of cesium chloride density gradient for first ultracentrifugation: 1.6 ml of light CsCl (1.2 g/ml) was added to a Beckman ultracentrifuge tube, followed by slow addition of 1.05 ml of heavy CsCl (1.45 g/ml) at the bottom; the volume of light and heavy CsCl added can also be changed to 2.5 ml of light CsCl and 2.5 ml of heavy CsCl according to the volume of the ultracentrifuge tube (Note: Do not mix the light and heavy CsCl at this step and a clear boundary between them shall be maintained).
2. 3-7 ml of virus-containing supernatant was gently added onto the liquid surface of light CsCl, then the ultracentrifuge tubes were placed into a centrifugal sleeve. The two opposite centrifuge tubes were weighed and balanced, and then were hung on corresponding two hooks on the centrifuge rotor. (Note: the operation must be gentle during the whole process.)
3. After the centrifuge tube was completely hung well, centrifugation was performed at 40000 RPM for 1 hour and 15 minutes at 20° C.
4. After the centrifugation was finished, the centrifugal tubes were firmly fixed to the universal clamp on the iron support in biological safety cabinet. Using a 5 ml syringe fitted with an 18G needle to carefully pierce the centrifuge tube below (~1 cm) the lowermost band of the intact viral particle and drawing the band merely which was stored on ice for a short period of time.
5. Preparation of CsCl solution for the second ultracentrifugation: 6 ml CsCl solution mixed uniformly in equal volume (3 ml light CsCl and 3 ml heavy CsCl) was added into the ultracentrifuge tube, and the virus solution collected in the step 4 was carefully perfused onto the liquid surface of the prepared CsCl solution. The perfused tubes were also carefully placed into the ultracentrifuge tube sleeves and the corresponding two tubes to be placed on the centrifuge rotor were weighed and balanced. Then the balanced centrifuge tubes were hanged onto the centrifuge rotor. (Note: the operation must be gentle during the whole process.)
6. Setting the centrifugation parameters: 20° C., 40,000 RPM, centrifuging for 18 hours.
7. After the centrifugation was finished, the centrifugal tubes were taken out carefully and firmly fixed to the universal clamp on the iron support in the biological safety cabinet. Using a 5 ml syringe fitted with an 18G needle to carefully pierce the centrifuge tube below (~1 cm) the band of the intact viral particle and drawing the band which was stored on ice for a short period of time.
8. In the biosafety cabinet, a PD-10 desalting column (the volume of the column is 5 ml) is taken out and the end of the bottom of the column is cut off, then the column is fixed on an iron support so that the maintenance liquid in the column can flow out naturally under the action of gravity. 3 to 4 times of the column volume (15 to 20 ml) of a dialysis solution (10 mM Tris solution (pH 7.4) containing 1 mM $MgCl_2$ and 10% glycerol, stored at 4° C. after filtration sterilization) were added to thoroughly wash the desalting column and completely replace the maintenance solution.
9. Ten 1.5 ml numbered centrifuge tubes were prepared for virus collection.
10. After the added dialysate completely flowing out, the virus solution collected by the second ultracentrifugation was added to the empty PD-10 column. The filtered solution inside the column was collected by the prepared centrifuge tubes according to the volume difference (1.2-1.5 ml/tube).
11. Dialysate was further added to perform the filtration wherein the adding amount is 2.5 ml each time, and the filtered solution was continuously collected into the prepared centrifuge tubes until ten centrifuge tubes were collected.
12. Eleven 1.5 ml centrifuge tubes were prepared, and 90 µl of 0.1% (w/v) SDS were added to each tube. 10 µl of virus were taken from each of the ten virus collection tubes and added to a centrifuge tube that was added with the SDS in advance and numbered accordingly. 10 µl of dialysate were added to a centrifuge tube added with SDS as a system control. After sufficiently mixing the virus and SDS solution, the mixture was placed at room temperature for 15-30 minutes with shaking occasionally. Then, the absorbance values at 260 nm and 280 nm were measured, and the optical virus particle number concentration in the virus solution was calculated according to the formula (1 $OD_{260}$=1×10$^{12}$ VP). $OD_{260}$ value reflects the concentration of viral DNA in the collection, and $OD_{280}$ value reflects the concentration of proteins in the collection. The ratio of $OD_{260}/OD_{280}$ is about 1.2-1.3.

13. After the obtained virus was correspondingly diluted, selecting two diluents with proper dilution and taking 100 μl for each to infect the AD293 cells which are inoculated into a 24-well plate and have proper concentration. The accurate titer of the virus is detected by an adenovirus titer titration kit (Shanghai Aoxiang biotechnology, Co., Ltd.) after 48 hours.

The ultracentrifugally purified high-quality virus liquid was divided into different clean centrifuge tubes with different volumes according to the concentration and the experimental requirement. They were stored at −80° C. for use with the date and virus name being marked.

Example 4: Klling Ability of Oncolytic Adenoviruses (OAd-shPDL1) on Tumor Cells (HCT 116, PANC1, HT29 and H460)

In this example, the killing ability of oncolytical adenovirus (OAd-shPDL1) was tested by MTT assay. Human tumor cells (HCT116, PANC1, HT29 and H460) were seeded in 96-well plates in a number of 3×10$^3$ cells per well with 100 μl culture medium in each well (HCT116 cells were cultured in medium McCoy's 5A+10% FBS; PANC-1 cells were cultured in medium DMEM+10% FBS; HT29 cells were cultured in medium DMEM/F12+10% FBS; H460 cells were cultured in RPMI1640+10% FBS; all of mediums were purchased from Gibco Co., Ltd). After 12 hours, 50 μl of medium were discarded and a 50 μl mixture of viruses (the viruses used were the control virus C-4.5K, OAd-shPDL1 virus 1-4.5K, 2-4.5K and 3-4.5K, respectively, which were prepared according to the method described in Preparation Example 5) and serum-free medium was added (this time point was recorded as 0 hour) with a multiplicity of infection (MOI) of 1, 3, 10, 30, 100 and 300, respectively. There are three duplicates for each MOI. 10 μl of MTT solution (purchased from Solite Biotech Co., Ltd.) (5 mg/ml, i.e., 0.5% MTT) were added to each well at time points of 48 hours and 72 hours, respectively, and incubation was further carried out for 4 hours; then all culture medium was carefully discarded without contacting and discarding cells. 150 μl of DMSO were added to each well, and shaken at a low speed for 10 minutes on a shaker to sufficiently dissolve the crystal substance, and the absorbance value at 490 nm was measured on a microplate reader. The commercial oncolytic adenovirus H101 was used as a control in this experiment wherein the same cells were treated with the same MOI of virus and the absorbance values were simultaneously measured at the same time point. In addition, 1 μM of paclitaxel solution was used as a system positive control. Data were analyzed using GraphPad Prism 5.04 and dose-response curves were plotted and $IC_{50}$ was calculated. The calculation formula of inhibition rate is as follows: inhibition rate of cell proliferation (IR %)=1−(OD tested sample-OD blank)×100%. The results of killing effect depending on does of oncolytic adenoviruses (OAd-shPDL1) on four kinds of tumor cells and the half-killing dose ($IC_{50}$) were shown in FIGS. 25-29.

The results showed that the killing effect on HCT116, PANC1, HT29 and H460 of oncolytic adenoviruses (control virus C-4.5K, OAd-shPDL1 viruses 1-4.5K, 2-4.5K and 3-4.5K) prepared according to the present disclosure exhibited obvious dose dependence, and all viruses had strong killing ability. The viruses according to the present disclosure had similar killing effect compared to the commercial oncolytic adenovirus H101. It is expected that the oncolytic adenoviruses of the present disclosure can be used for the treatment of the above-mentioned types of tumors in future clinical applications.

Example 5: Efficacy of shPDL1 Expressed by Oncolytic Adenovirus OAd-shPDL1

This example includes in vitro functional assays in cells and in vivo functional assays in a tumor-bearing mouse model. The oncolytical adenoviruses used in the experiment were control virus C-4.5K and OAd-shPDL1 virus 1-4.5K (the viruses used were prepared according to preparation example 5).

1. Cell Assay for Detecting shPDL1 Function Expressed by Oncolytic Adenovirus OAd-shPDL1 In Vitro (1) Cell Assay Against Human Breast Cancer Cells MDA-MB-231

Figure 30:
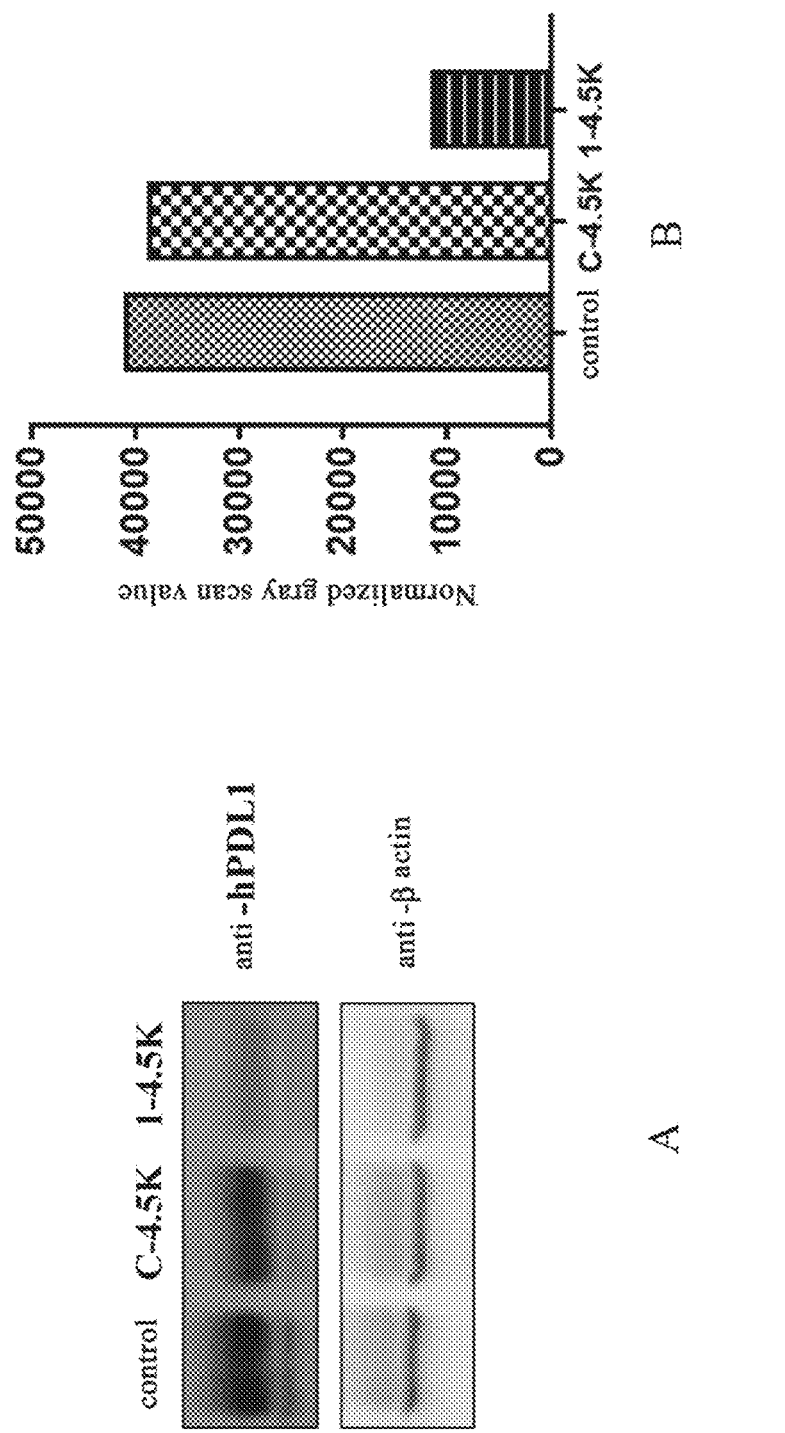
FIG. 30 shows the inhibitory effect of oncolytic adenovirus OAd-shPDL1 #1-4.5K (1-4.5K) and system control virus OAd-C-4.5K (C-4.5K) constructed according to the present disclosure on hPDL1 expression in human breast cancer cells MDA-MB-231 in Example 5. Fig. A shows the results of Western blot, which indicates the expression change of hPDL1 in the cell samples and the expression of intracellular protein reference β-actin in cells after treatment by different viruses. The "control" refers to a blank control group without any virus treatment. Fig. B shows, based on the result of Western blot, the grayscale scan value of hPDL1 band using the intracellular protein reference β-actin as a normalized reference. The abscissa represents different groups, and the ordinate is the grayscale scanning value.

The cell line used in the experiment was human breast cancer cell line MDA-MB-231 with high expression level of human PDL1. MDA-MB-231 cells were seeded into 3 wells of a 6-well plate in an amount of 1×10$^6$ cells per well. After 12 hours, 100 μl of mixture of virus and serum-free L15 medium (L15 medium was purchased from Gibco) containing 1×10$^7$PFU (MOI=10) oncolytic adenovirus C-4.5K or 1-4.5K were added in each of two wells, respectively, and 100 μl of serum-free medium were added to the remaining 1 well as a blank control. The 6-well plate was gently "cross-shaken" to make the viruses distributed evenly in the culture wells as well as possible. After incubation at 37° C. and 5% $CO_2$ for 24 hours, cell samples were harvested after digesting cells with trypsin. The harvested cell samples were rinsed twice with clean PBS, and the harvested cell pellet was suspended in RIPA buffer with protease inhibitor (50 mM Tris-Cl (pH7.4), 150 mM NaCl, 1% NP-40, 0.5% sodium deoxycholate, 0.1% SDS and 1/20 Cocktail protease inhibitor) and placed on ice to get lysis for 30 minutes. The cell samples were mixed with shaking occasionally, centrifuged at 12000 RPM for 5 minutes, and then the supernatant and the cell pellet were harvested and stored at −20° C., respectively. The protein level of hPDL1 in the harvested supernatants of three groups of MDA-MB-231 cells was detected by conventional Western blotting, wherein the primary antibody was rabbit-derived PDL1 antibody (Cat. No. NBP2-15791) from Novusbio. Each group was in triplicate. The Western result and the grayscale scan value analysis were shown in FIG. 30.

According to the above results of Western experiment, it can be seen that the expression level of hPDL1 in MDA-MB-231 cells treated with the OAd-shPDL1 oncolytic virus according to the present disclosure significantly changed. The expression level of hPDL1 in MDA-MB-231 cells of OAd-shPDL1 treatment group (1-4.5K group) was reduced by about 72.4% compared to the control group, while the expression level of hPDL1 in MDA-MB-231 cells of oncolytic virus control group (C-4.5K group) did not significantly changed.

Figure 31:
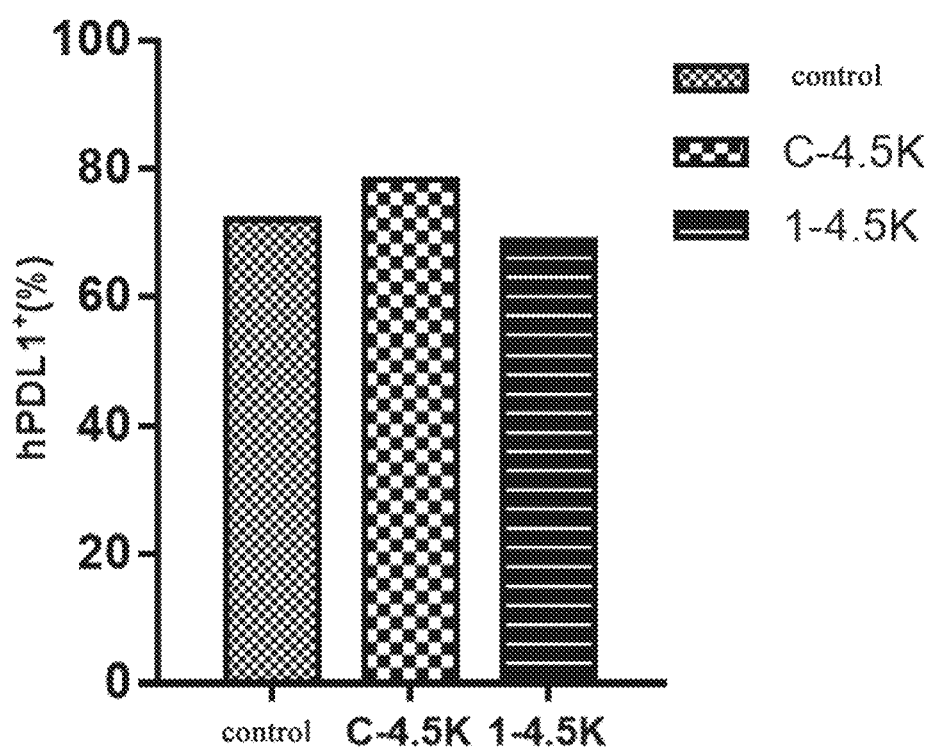
FIG. 31 shows, in Example 5, the percentage change of MDA-MB-231 tumor cells expressing hPDL1 on the cell membrane detected by FACS after the cells were treated with oncolytic adenovirus OAd-shPDL1 #1-4.5K (1-4.5K), and system control virus OAd-C-4.5K (C-4.5K) constructed according to the present disclosure, wherein "control" refers to a blank control group without any virus treatment. The abscissa represents different groups, and the ordinate represents the percentage (%) of cells expressing hPDL1.

Next, MDA-MB-231 cells were inoculated into three wells of a 12-well plate with 1×10$^4$ cells per well. After 12 hours, a mixture of 1×10$^5$ PFU (MOI=10) of oncolytic adenovirus C-4.5K or 1-4.5K and serum-free medium was added to two wells of the three wells, respectively, and equal volume of the serum-free medium was added to the remaining one well as a blank control. The 12-well plate was gently "cross-shaken" to make the virus distributed evenly in the wells as well as possible. After cultured in an incubator at 37° C. and 5% $CO_2$ for 24 hours, cell samples were harvested and were detected by FACS using CD274 flow cytometry antibody (purchased from ebioscience) to detect percentage of cells expressing hPDL1 in cell samples. All the groups were in triplicate. The flow cytometry results were shown in FIG. 31.

The experimental results showed that after the MDA-MB-231 cells were treated with the oncolytic virus OAd-shPDL1 according to the present disclosure, the percentage of cells in which hPDL1 can be detected on the cell membrane was reduced by about 5% compared to the blank control group without any treatment, whereas the percentage of cells in which hPDL1 can be detected in the oncolytic virus control group (C-4.5K group) was increased by about 9% compared to the blank control group without any treatment. This is consistent with the statement in related literature that oncolytic viruses can induce the increase of hPDL1 expression on the surface of tumor cells after stimulating the tumor cells (see, for example, the scientific literature "Dmitriy Zamarin, et al. PD-L1 in tumor microenvironment mediates resistance to oncolytic immunotherapy. *J Clin Invest.* 2018; 128(4): 1413-1428."; "Zuqiang Liu, et al. Rational combination of oncolytic vaccinia virus and PD-L1 blockade works synergistically to enhance therapeutic efficacy. *Nat Commun.* 2017 Mar. 27; 8:14754-14765."; or "Praveen K. Bommareddy, et al. Integrating oncolytic viruses in combination cancer immunotherapy. Nat Rev Immunol. 2018 May 9. doi: 10.1038/s41577-018-0014-6"). The results indicated that after treating MDA-MB-231 cells with OAd-shPDL1 oncolytic virus, the percentage of tumor cells with increased hPDL1 expression induced by the stimulation of oncolytic virus can be reduced to 95% of the percentage before the stimulation. It also fully demonstrated that shPDL1 expressed in OAd-shPDL1 oncolytic virus did knock down the expression level of hPDL1 in MDA-MB-231 tumor cells and decreased the number of cells expressing hPDL1 on the surface of MDA-MB-231 tumor cells.

(2) Cell Assay Against Human Colon Cancer Cell HCT116

Figure 32:
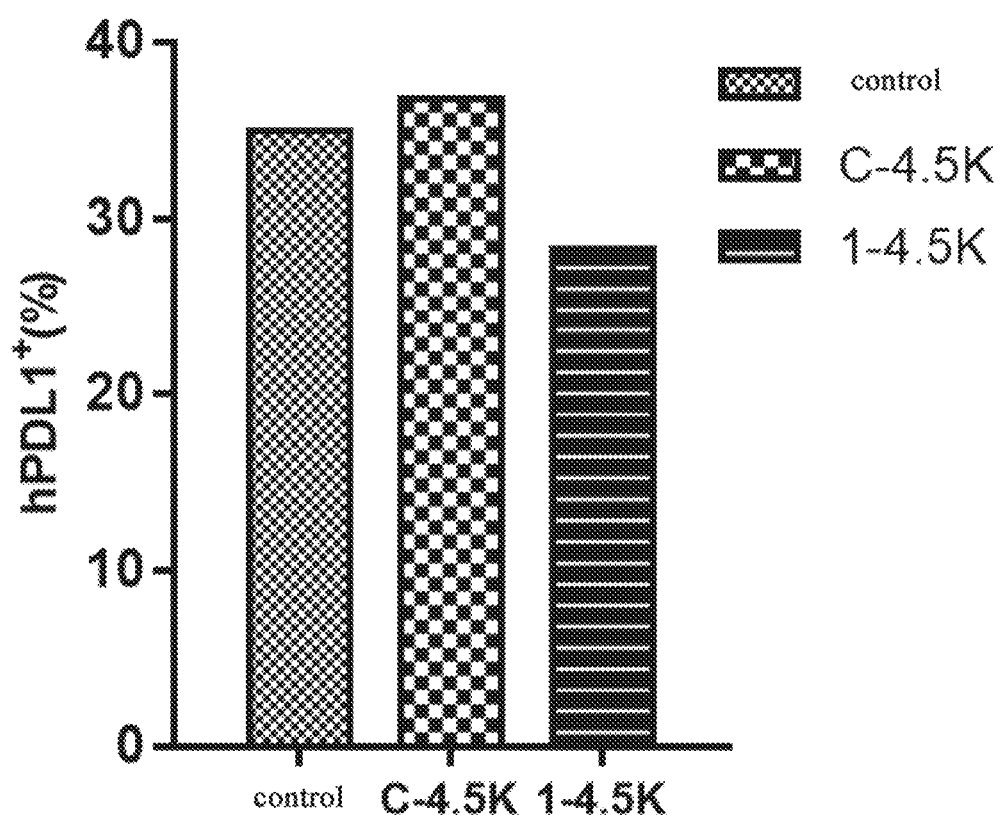
FIG. 32 shows, in Example 5, the percentage change of HCT116 tumor cells expressing hPDL1 on the cell membrane detected by FACS after treatment with oncolytic adenovirus OAd-shPDL1 #1-4.5K (1-4.5K), and system control virus OAd-C-4.5K (C-4.5K) constructed according to the present disclosure, wherein "control" refers to a blank control group without any virus treatment. The abscissa represents different groups, and the ordinate represents the percentage (%) of cells expressing hPDL1.

Human colon cancer cells HCT116 were inoculated into three wells of a 12-well plate with $1\times10^4$ cells per well. After 12 hours, a mixture solution of $1\times10^5$ PFU (MOI=10) of oncolytic adenovirus C-4.5K or 1-4.5K and serum-free medium was added in two wells respectively, and equal volume of the serum-free medium McCoy's 5A was added to the remaining one well as a blank control. The 12-well plate was gently "cross-shaken" to make the virus distributed evenly in wells as well as possible. After cultured in an incubator at 37° C. and 5% $CO_2$ for 24 hours, the cell samples were harvested by digestion with trypsin, and FACS was performed using flow cytometry antibody of CD274 to detect percentage of cells expressing hPDL1 in cell samples. All the groups were in triplicate. The flow cytometry results were shown in FIG. 32.

The experimental results showed that after the HCT116 cells were treated with the oncolytic virus OAd-shPDL1 according to the present disclosure, the percentage of cells in which hPDL1 can be detected on the cell membrane was reduced by about 19.1% compared to the blank control group without any treatment, whereas the percentage of cells in which hPDL1 can be detected in the oncolytic virus control group (C-4.5K group) was increased by about 5.3% compared to the blank control group without any treatment. This is consistent with the statement in related literature that oncolytic viruses can induce the increase of hPDL1 expression on the surface of tumor cells after stimulating the tumor cells (see, for example, the scientific literature "Dmitriy Zamarin, et al. PD-L1 in tumor microenvironment mediates resistance to oncolytic immunotherapy. *J Clin Invest.* 2018; 128(4):1413-1428."; "Zuqiang Liu, et al. Rational combination of oncolytic vaccinia virus and PD-L1 blockade works synergistically to enhance therapeutic efficacy. *Nat Commun.* 2017 Mar. 27; 8:14754-14765."; or "Praveen K. Bommareddy, et al. Integrating oncolytic viruses in combination cancer immunotherapy. Nat Rev Immunol. 2018 May 9. doi: 10.1038/s41577-018-0014-6"). The results indicated that after treating HCT116 cells with OAd-shPDL1 oncolytic virus, the percentage of tumor cells with increased hPDL1 expression induced by the stimulation of oncolytic virus can be reduced to 80.9% of the percentage before the stimulation. It also fully demonstrated that shPDL1 expressed in OAd-shPDL1 oncolytic virus did knock down the expression level of hPDL1 in HCT116 tumor cells and decreased the number of cells expressing hPDL1 on the surface of HCT116 tumor cells.

2. Tumor-Bearing Mouse Model Experiment for the Detection of the Function of shPDL1 Expressed by Oncolytic Adenovirus OAd-shPDL1 In Vivo In this part, human colon cancer cells HCT116 were inoculated subcutaneously in the back of 9 BALB/C nude mice, and the number of cells inoculated in each nude mouse was $5\times10^6$. After about 9 days, the mice were randomly divided into 3 groups after tumor formed subcutaneously. The first group was blank control group without any treatment. In the second group, subcutaneous tumor was injected with control oncolytic adenovirus C-4.5K by intratumoral injection, wherein the amount of virus injected per nude mouse was $1\times10^9$ PFU, and the injection volume was 100 µl, For the third group, intratumoral injection was also used to inject oncolytic adenovirus 1-4.5K into the subcutaneous tumor, wherein the amount of virus injected per nude mouse was $1\times10^9$ PFU, and the injection volume was 100 µl. The injection was performed according to such dose and manner once a day for 3 days and no treatment was preformed on the 4th day. Nude mice were sacrificed on the 5th day to harvest tumor tissue. RPA buffer containing the protease inhibitor (formulation is the same with above mentioned) was added to a portion of tissue samples which were then subjected to homogenization to extract tissue proteins. The protein expression level of hPDL1 in the tumor tissues was detected by Western blotting. The results were shown in the FIG. 33 and FIG. 34.

Figure 33:
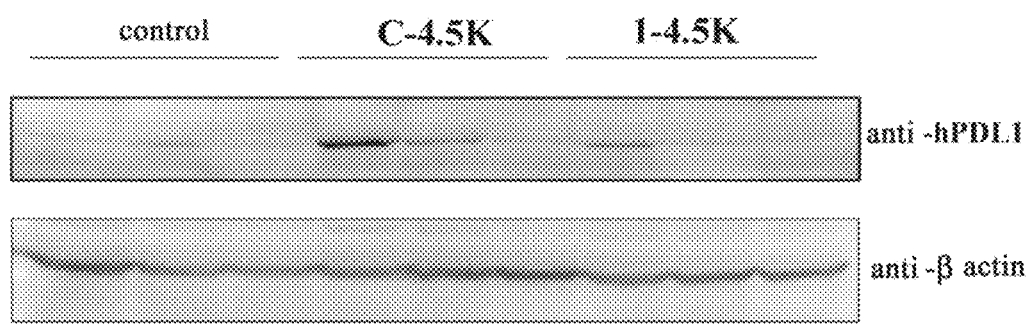
FIG. 33 shows, in example 5, the inhibitory effect of oncolytic adenovirus OAd-shPDL1 #1-4.5K (1-4.5K) and system control virus OAd-C-4.5K (C-4.5 K) constructed according to the present disclosure on hPDL1 expression in HCT116 cells subcutaneously inoculated in the back of BALB/C nude mice, which is detected by Western blot; results of Western blot are shown in the figure, which indicates the expression change of hPDL1 in the cell samples and the expression of intracellular protein reference β-actin in cells after treatment by different viruses. "Control" refers to a blank control group without any virus treatment. In the figure, there are three loading wells for each group and the sample in each loading well was from three different nude mice of same group, respectively.
Figure 34:
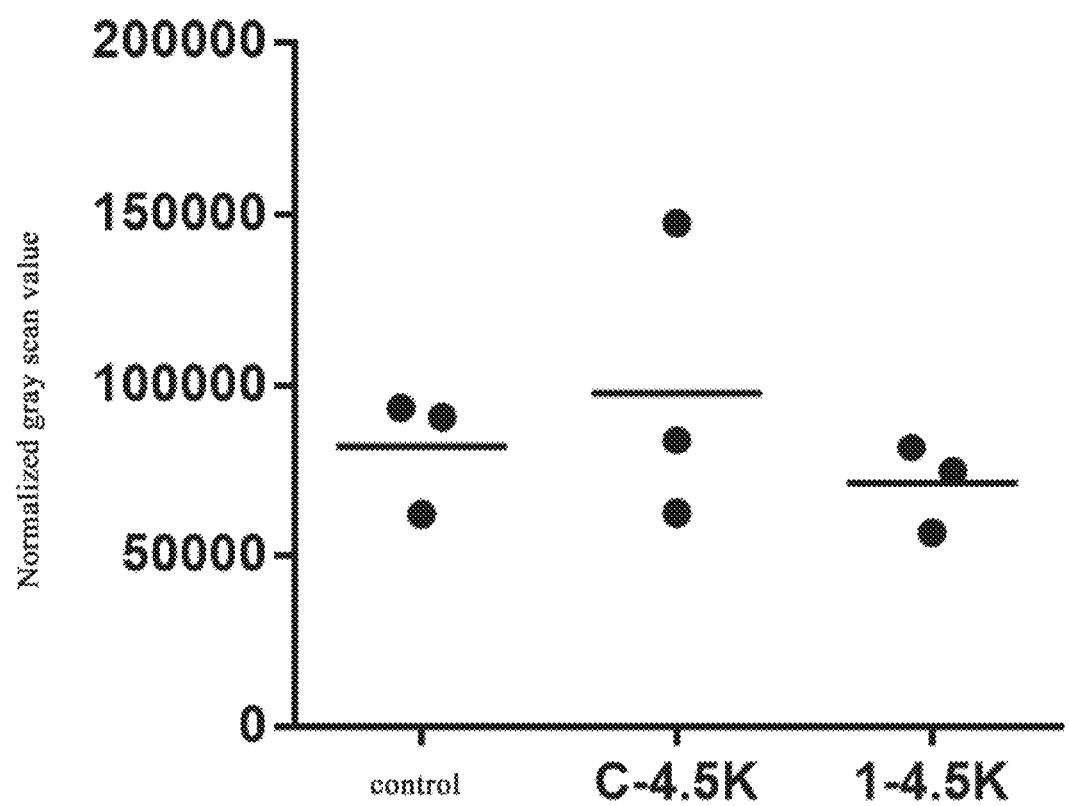
FIG. 34 shows, based on the result of Western blot in FIG. 33, the grayscale scan values of hPDL1 bands obtained using the intracellular protein reference β-actin as a normalized reference. The abscissa represents different groups, and the ordinate represents the grayscale scanning value.

The bands of the Western result shown in FIG. 33 were scanned to convert into gray values which were normalized according to the gray value of the respective housekeeping gene (β-actin), and then the scatter distribution map of FIG. 34 was obtained. Based on the respective median value, it can be seen that after treating subcutaneously inoculated HCT116 cells of BALB/C with control oncolytic adenovirus (C-4.5), the expression level of hPDL1 in this group was up-regulated by 20% compared to the blank control group without any treatment. In contrast, after treating subcutaneously inoculated HCT116 cells of BALB/C with the oncolytic adenovirus OAd-shPDL1, the expression level of hPDL1 in this group was reduced by 25% compared to that of the oncolytic adenovirus control group, and the expression level was also lower than that of the blank control group without any treatment. Therefore, this result demonstrated that shPDL1 expressed in the oncolytic adenovirus OAd-shPDL1 (1-4.5) did reduce the expression of hPDL1 in human tumor cell transplant in vivo.

Example 6: Combined Killing Experiment of Oncolytic Adenovirus OAd-shPDL1 and Human NK Cells on Human Tumor Cell Lines The oncolytic adenovirus OAd-shPDL1 of the present disclosure comprises one shPDL1 expression cassette, which can express shPDL1 in the infected tumor cells, thereby knocking down the expression level of hPDL1 in the tumor cells and reducing the presence of hPDL1 on the surface of the tumor cells. Finally, the immunosuppressive effect on immune cell activation caused by binding of hPDL1 on the surface of tumor cells to PD1 of immune cells (including T cells or NK cells) can be eventually attenuated or eliminated. Therefore, this example mainly detected at the cellular level that whether the oncolytic adenovirus OAd-shPDL1 (1-4.5K) (prepared by the method described in Preparation Example 5) and human NK cells have a synergistic effect on killing human tumor cells. In the experiment, trypan blue staining method was used to detect whether the oncolytic adenovirus OAd-shPDL1 (1-4.5K) and human NK cells exhibit a synergistic effect in the combined killing against human colon cancer cell HCT116 and human lung cancer cell A549.

Trypan blue staining is a classic method for counting dead/living cells. When cells are damaged or dead, trypan blue can penetrate the denatured cell membrane, binds to and stains the disintegrated DNA, while living cells prevent the dye from entering the cell. Thus, dead cells and living cells can be identified.

1. Cell Assay Against Human Colon Cancer Cell HCT116

It was determined by trypan blue staining test that when the killing dose of oncolytic adenovirus OAd-shPDL1 (1-4.5K) to HCT116 cells is about MOI=1~3, the killing rate is between 40% and 60%; when the killing dose of human NK cells to HCT116 cells is about 5:1 for NK:HCT116 (E:T ratio), the killing rate is between 10% and 20%. The killing doses were suitable respectively, which were suitable for combined killing experiments.

First, HCT116 cells were seeded in 24-well plates with $2 \times 10^4$ cells per well. After 12 hours, the oncolytic adenovirus OAd-shPDL1 (1-4.5K) was added in different MOI (MOI-1, 3). After mixing well, the culture was returned to a $CO_2$ incubator at 37° C. for further incubation for 6 hours. Then the supernatant of medium containing the virus was removed, and the cells were washed gently with clean PBS once, then fresh complete medium (McCoy's 5A+10% FBS) was added. At 18 hours after remove of the virus, activated NK cells (frozen NK cells were cultured after resuscitation) were added to each well according to the predetermined ratio of effective cells to target cells (E:T=5:1). The experimental group was 1-4.5K+NK group. Cells were harvested at 24 hours after NK cells were added, and the number of living cells was counted after stained by trypan blue. In the experiment, there were one HCT116 cell group used as blank control group in which none of the oncolytic adenovirus OAd-shPDL1 (1-4.5K) or NK cells were added; one 1-4.5K group in which oncolytic adenovirus OAd-shPDL1 (1-4.5K) was added at corresponding time point without NK cells; and one NK group in which NK cells were added at corresponding time point without oncolytic adenovirus ©rid-shPDL1 (1-4.5K). All the control groups underwent the corresponding medium replacement operations at corresponding time points. All the experiments were repeated for three times or more, and the averages were used for statistical analysis.

Figure 35:
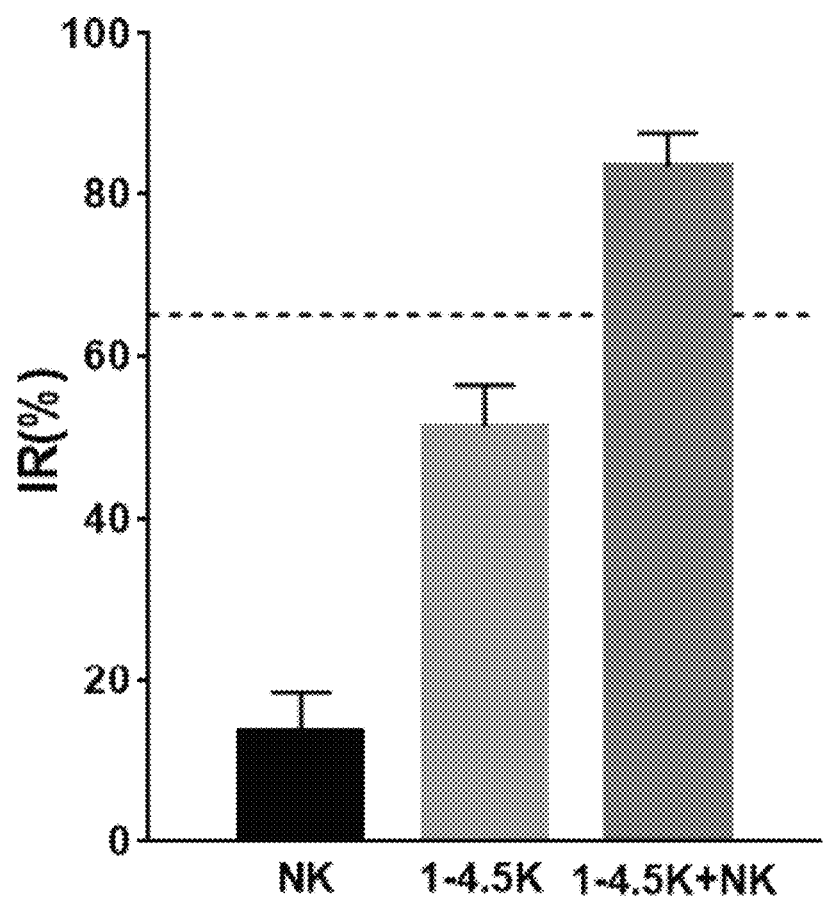
FIG. 35 shows synergistic killing effect of the oncolytic adenovirus OAd-shPDL1 #1-4.5K (1-4.5K) (MOI=1) constructed according to the present disclosure combined with NK cells (E:T=5:1) on HCT116 cells in Example 6. The abscissa represents the different groups, and the ordinate represents the percentage value of the corresponding inhibition rate.

The results when the MOI of the oncolytic adenovirus OAd-shPDL1 (1-4.5K) was 1 and the effector to target cell ratio (E:T) of NK cells was 5:1 were shown in FIG. 35 (wherein X axis represents the different groups, and Y axis represents the corresponding percentage of inhibition rate). It was showed that the combined administration of oncolytic adenovirus OAd-shPDL1 (1-4.5K) and NK cells had significant synergistic killing effect against HCT116 cells, and the synergistic inhibition rate was about 83%. In contrast, in this experiment, the inhibition rate of administration of oncolytic adenovirus OAd-shPDL1 (1-4.5K) alone was about 51% and the inhibition rate of administration of NK cells alone was about 14%; and the sum of the two was shown by dotted lines in the figure. In addition, the inhibition rate of the blank group was about 0 (not shown in the figure).

Figure 36:
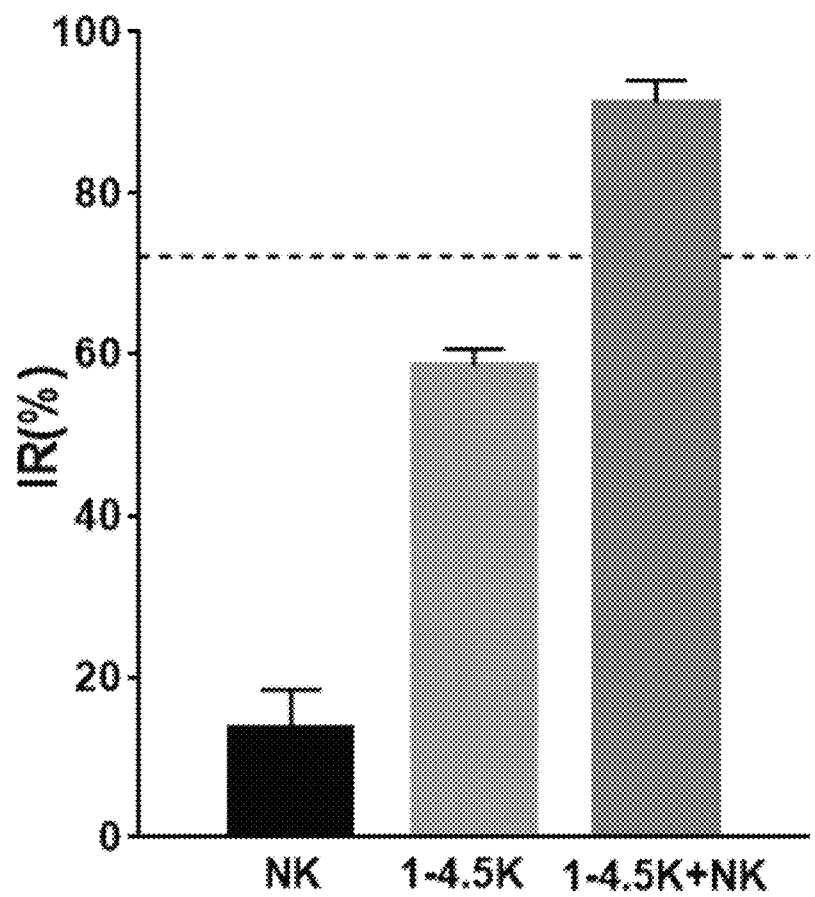
FIG. 36 shows synergistic killing effect of the oncolytic adenovirus OAd-shPDL1 #1-4.5K (1-4.5K) (MOI=3) constructed according to the present disclosure combined with NK cells (E:T=5:1) on HCT116 cells in Example 6. The abscissa represents the different groups, and the ordinate represents the percentage value of the corresponding inhibition rate.

The results when the MOI of the oncolytic adenovirus OAd-shPDL1 (1-4.5K) was 3 and the effector to target cell ratio (E:T) of NK cells was 5:1 were shown in FIG. 36 (wherein X axis represents the different groups, and Y axis represents the corresponding percentage of inhibition rate). It was showed that the combined administration of oncolytic adenovirus OAd-shPDL1 (1-4.5K) and NK cells had significant synergistic killing effect against HCT116 cells, and the synergistic inhibition rate was about 91%. In contrast, in this experiment, the inhibition rate of administration of oncolytic adenovirus OAd-shPDL1 (1-4.5K) alone was about 58% and the inhibition rate of administration of NK cells alone was about 14%; and the sum of the two was shown by dotted lines in the figure. In addition, the inhibition rate of the blank group was about 0 (not shown in the figure).

2. Cell Assay Against Human Lung Cancer Cell A549

It was determined by trypan blue staining test that when the killing dose of oncolytic adenovirus OAd-shPDL1 (1-4.5K) to A549 cells is about MOI=30, the killing rate is between 40% and 60%; when the killing dose of human NK cells to A549 cells is an ET ratio of about 5:1, the killing rate is between 10% and 20%. The killing doses were suitable respectively, which were suitable for combined killing experiments.

First, A549 cells were seeded in 24-well plates with $2 \times 10^4$ cells per well. After 12 hours, the oncolytic adenovirus OAd-shPDL1 (1-4.5K) was added with MOI (MOI=30). After mixing well, the culture was returned to a $CO_2$ incubator at 37° C. for further incubation for 6 hours. Then the supernatant of medium containing the virus was discarded, and the cells were washed gently with clean PBS once, and then fresh complete medium (DMEM/F12+10% FBS) was added. At 18 hours after the virus was removed, activated NK cells (frozen NK cells were cultured after resuscitation) were added to each well according to the predetermined ratio of effective cells to target cells (E:T=5:1). The experimental group was 1-4.5K+NK group. Cells were harvested at 24 hours after NK cells were added and the number of living cells was counted by trypan blue staining. In the experiment, there were also one A549 cells group as blank control group in which none of the oncolytic adenovirus OAd-shPDL1 (1-4.5K) or NK cells were added; one 1-4.5K group in which oncolytic adenovirus OAd-shPDL1 (1-4.5K) was added at corresponding time point but no NK cells were added; and one NK group in which NK cells were added at corresponding time point but no oncolytic adenovirus OAd-shPDL1 (1-4.5K) was added. All the control groups underwent the corresponding medium replacement operations at corresponding times. All the experiments were repeated for three times or more, and the averages were used for statistical analysis.

Figure 37:
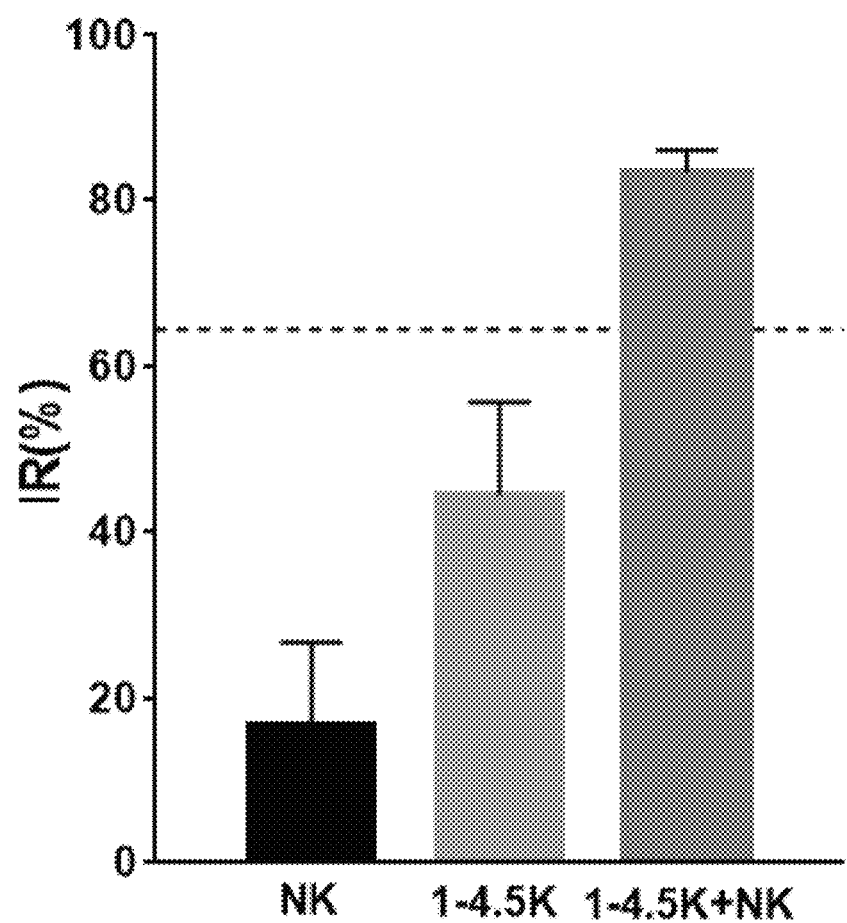
FIG. 37 shows synergistic killing effect of the oncolytic adenovirus OAd-shPDL1 #1-4.5K (1-4.5K) (MOI=30) constructed according to the present disclosure combined with NK cells (E:T=5:1) on A549 cells in Example 6. The abscissa represents the different groups, and the ordinate represents the percentage value of the corresponding inhibition rate.
Figure 38:
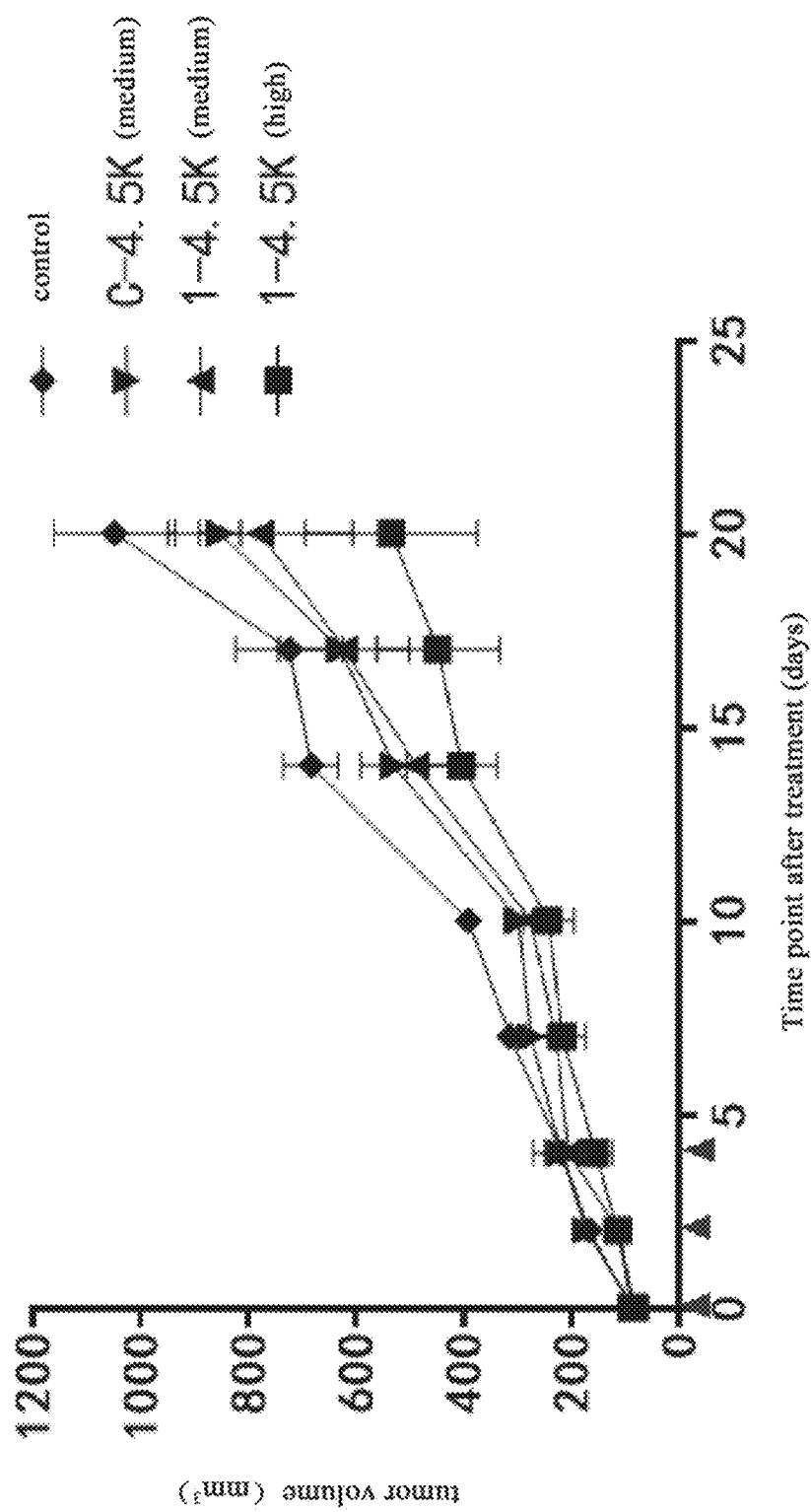
FIG. 38 shows the change of tumor volume in the HCT116 tumor-bearing NOD-SCID immunodeficiency mice treated with oncolytic adenovirus OAd-shPDL1 #1-4.5K (1-4.5K) and system control virus OAd-C-4.5K (C-4.5K) constructed according to the present disclosure in Example 7; the gray triangles on the abscissa indicate the time points of the administration, and the abscissa represents the time (day) after the administration, and the ordinate represents tumor volume ($mm^3$).

The results were shown in FIG. 37 (wherein X axis represents the different groups, and Y axis represents the corresponding percentage of inhibition rate). It was showed that the combined administration of oncolytic adenovirus OAd-shPDL1 (1-4.5K) and NK cells had significant synergistic killing effect against A549 cells, and the synergistic inhibition rate was about 83%. In contrast, in this experiment, the inhibition rate of administration of oncolytic adenovirus OAd-shPDL1 (1-4.5K) alone was about 45% and the inhibition rate of administration of NK cells alone was about 16.9%; and the sum of the two was shown by dotted lines in the figure. In addition, the inhibition rate of the blank group was about 0 (not shown in the figure).

Example 7: In Vivo Growth Inhibition Assay of Oncolytic Adenovirus OAd-shPDL1 on Human Tumor Cells Subcutaneously Inoculated into Immunodeficient Mice In this example, the NOD-SCID immunodeficient mice were inoculated subcutaneously (the number of cells inoculated subcutaneously per mouse was $5\times10^6$ cells) with the human colon cancer cell HCT116 to prepare the tumor-bearing mouse model which was used to detect the growth inhibitory effect of oncolytic adenovirus OAd-shPDL1 (1-4.5K) on HCT116. Control oncolytic virus C-4.5K was used as a negative control virus. The control virus C-4.5K and OAd-shPDL1 virus 1-4.5K used in the experiment were prepared by the method described in Preparation Example 5. Selecting twelve tumor-bearing mice with subcutaneously inoculated tumor meeting the volume requirement (tumor volume was 90-120 mm$^3$) and dividing into four groups in the manner of randomized block, three mice per group. The first group was control group (Blank Control) wherein each mouse was injected with 100 μl of adenovirus preservation solution (i.e., 10 mM Tris solution (pH 7.4) containing 1 mM of MgCl$_2$ and 10% glycerol) every time. The second group was a medium-dose control oncolytic virus group (C-4.5K (medium)) wherein each mouse was injected with 100 μl of viral suspension containing $1\times10^8$ PFU oncolytic virus C-4.5K every time. The third group was a medium-dose oncolytic virus group (1-4.5K (medium)) wherein each mouse was injected with 100 μl of viral suspension containing $1\times10^8$ PFU oncolytic virus 1-4.5K every time. The fourth group is a high-dose oncolytic virus group (1-4.5K (high)) wherein each mouse was Injected with 100 μl of viral suspension containing $1\times10^9$ PFU oncolytic virus 1-4.5K every time. A total of three administrations were performed throughout the experiment and the drug was administered every other day. The first administration started from the day of grouping (recorded as day 0). Tumor diameter and the body weight of the mice were measured twice a week. After day 21, the mice were sacrificed and tumors were taken for photographing. The experimental results were shown in FIGS. 38, 39, 40 and 41, respectively.

Figure 39:
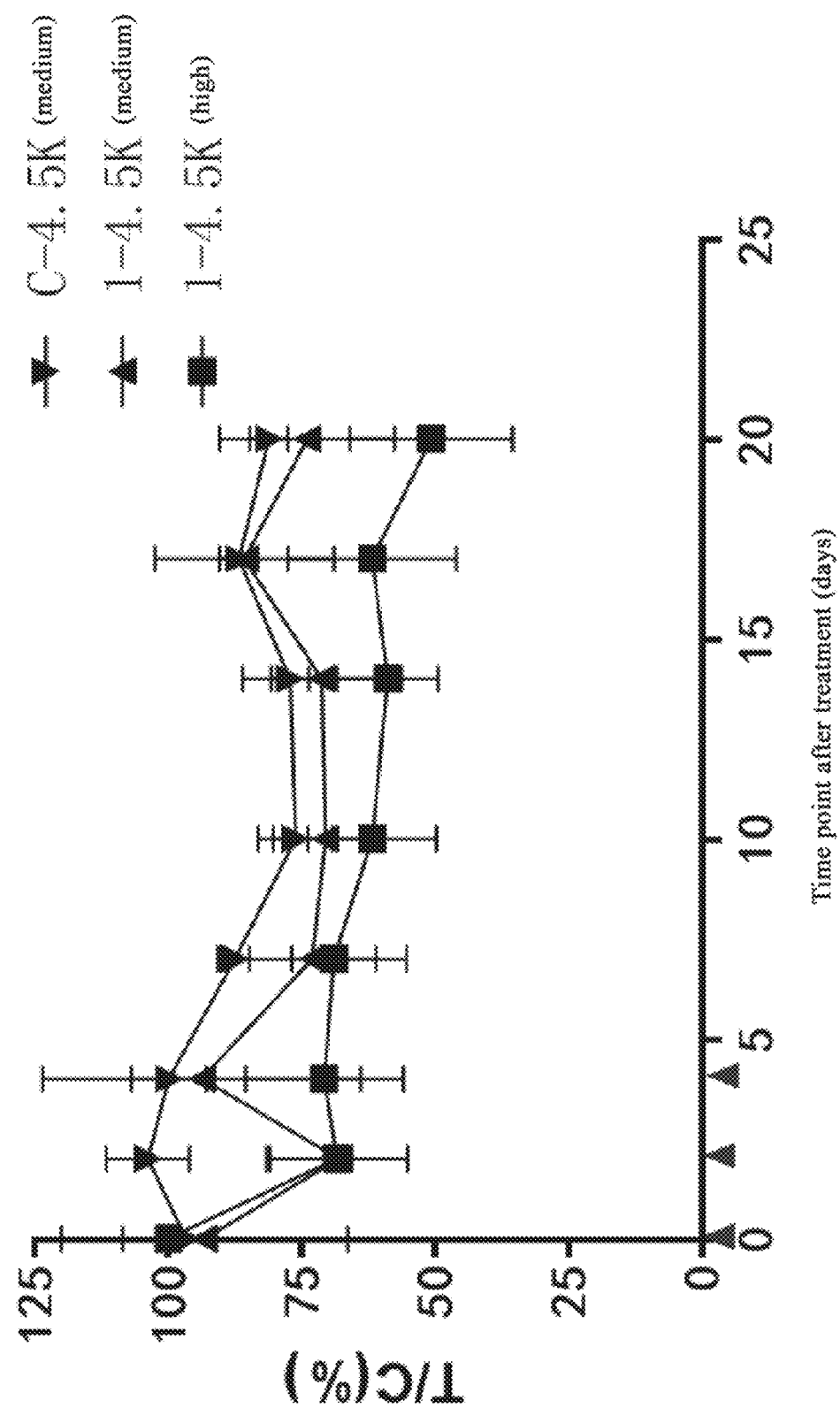
FIG. 39 shows the changes of T/C in the HCT116 tumor-bearing NOD-SCID immunodeficiency mice treated with oncolytic adenovirus OAd-shPDL1 #1-4.5K (1-4.5K) and system control virus OAd-C-4.5K (C-4.5K) constructed according to the present disclosure in Example 7; gray triangles on the abscissa indicate the time points of the administration, and the abscissa represents the time (day) after the administration, and the ordinate represents T/C (%).
Figure 40:
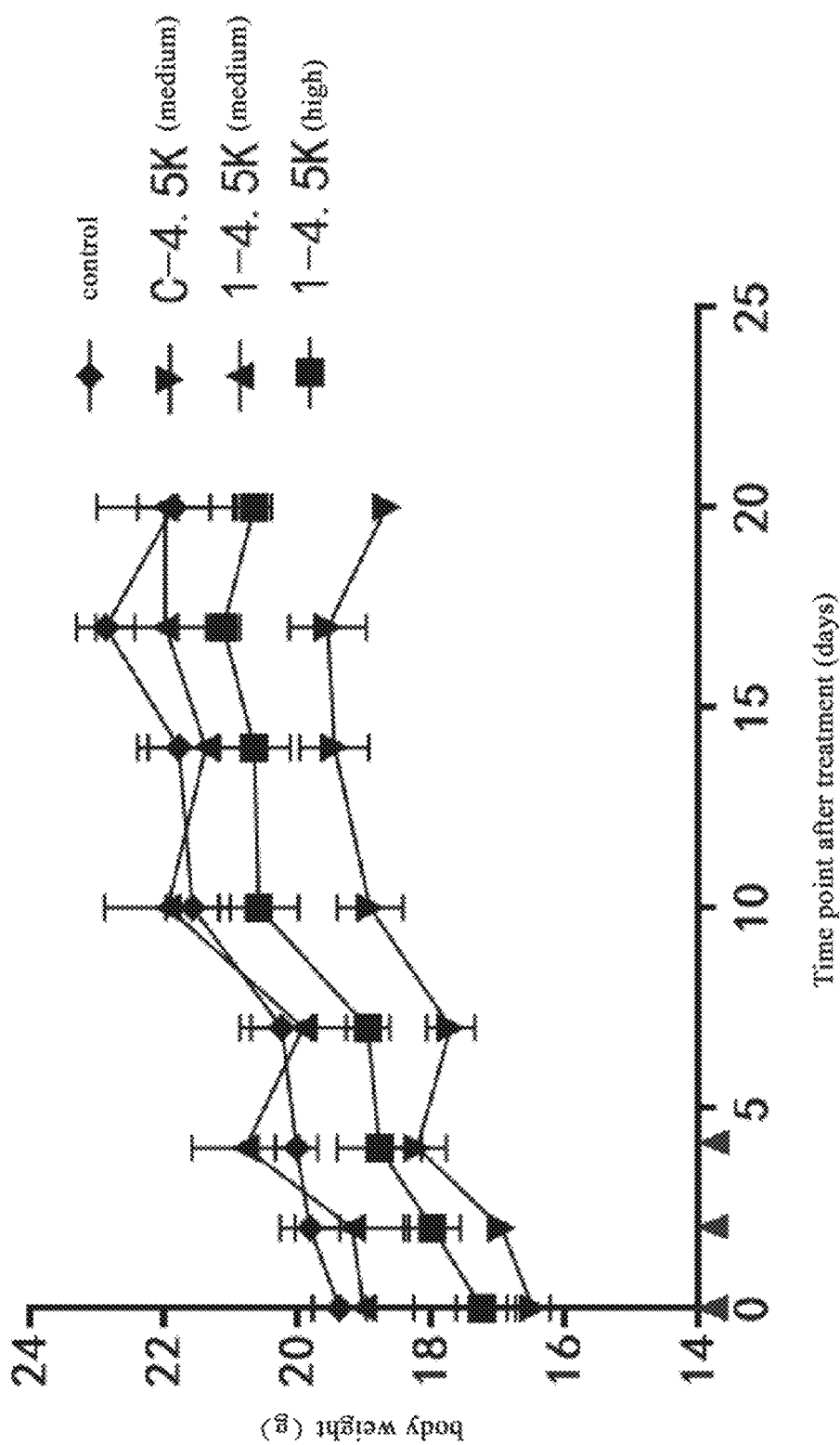
FIG. 40 shows the changes of body weight of the HCT116 tumor-bearing NOD-SCID immunodeficiency mice treated with oncolytic adenovirus OAd-shPDL1 #1-4.5K (1-4.5K) and system control virus OAd-C-4.5K (C-4.5K) constructed according to the present disclosure in Example 7; gray triangles on the abscissa indicate the time points of administration, and the abscissa represents the time (day) after administration, and the ordinate represents body weight (g).
Figure 41:
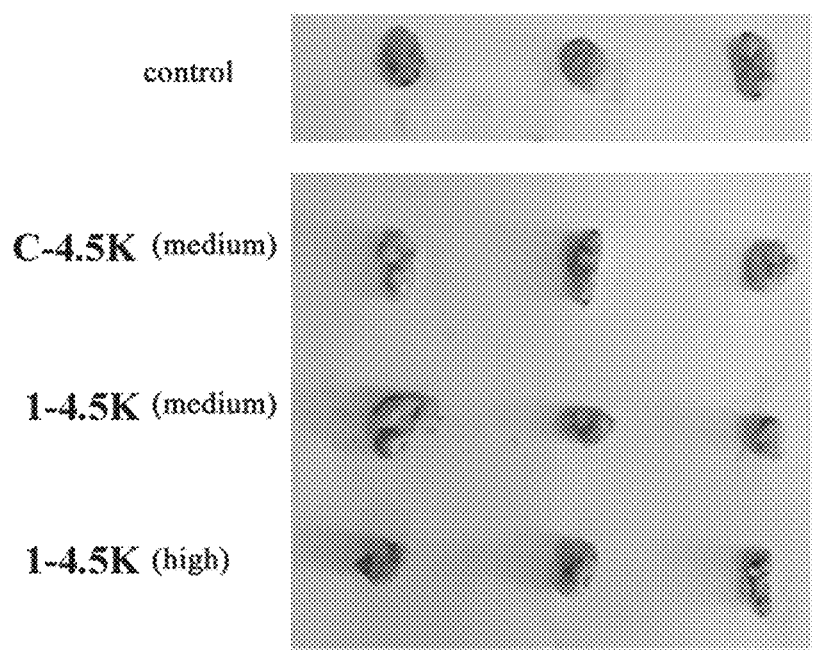
FIG. 41 shows the photographs of tumors taken from mice after sacrifice in Example 7, wherein the mice were HCT116 tumor-bearing NOD-SCID immunodeficiency mice treated with oncolytic adenovirus OAd-shPDL1 #1-4.5K (1-4.5K) and system control virus OAd-C-4.5K (C-4.5K) constructed according to the present disclosure.
Figure 42:
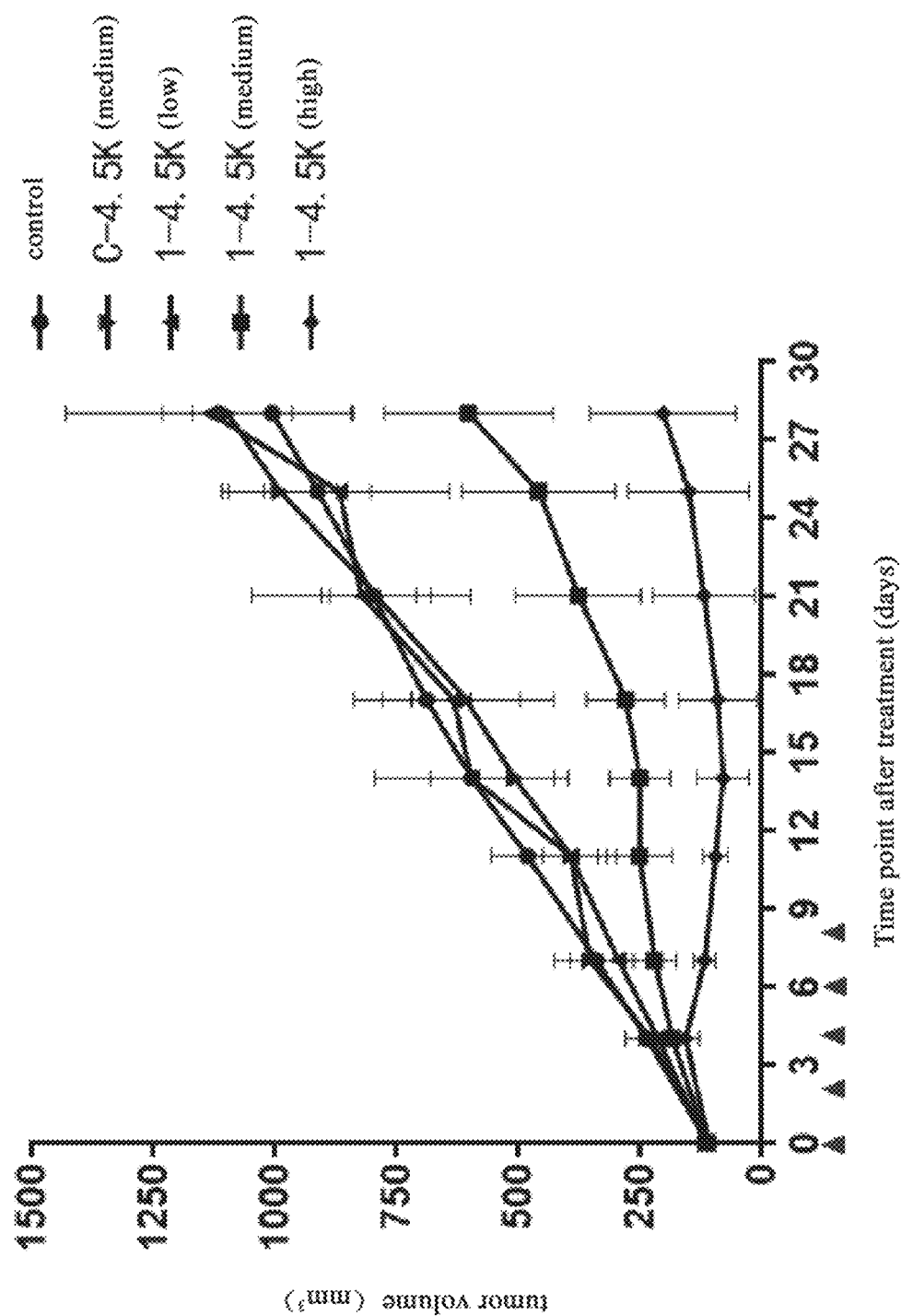
FIG. 42 shows the change of tumor volume in HCT 116-bearing BALB/C nude mice treated with oncolytic adenovirus OAd-shPDL1 #1-4.5K (1-4.5K) and system control virus OAd-C-4.5K (C-4.5K) constructed according to the present disclosure in Example 7; gray triangles on the abscissa indicate the time points of administration, and the abscissa represents the time (day) after administration, and the ordinate represents tumor volume ($mm^3$).

Consider the above results comprehensively: when oncolytic adenovirus OAd-shPDL1 (1-4.5K) was used to treat HCT116 tumor cells inoculated subcutaneously in NOD-SCID immunodeficiency mice, it can inhibit the growth of tumor cells to a certain extent, Compared to the medium-dose group (1-4.5K (medium)) and the control virus group (C-4.5K (medium)), the high-dose group (1-4.5K (high)) showed superior growth inhibition activity and showed a significant dose-dependent behavior (see FIG. 38), but the relative tumor proliferation rate (T/C %) did not achieve 40% or less (see FIG. 39). In terms of inhibiting tumor growth, comparing the equal dose groups of OAd-shPDL1 (1-4.5K) and control backbone virus C-4.5K, the results did not show a better tumor suppressive effect although shPDL1 expressed by OAd-shPDL1 (1-4.5K) virus caused a decrease in the expression level of hPDL1 in tumor cells (see FIGS. 38, 39, 41). There was no significant change in body weight for all groups of mice, indicating that the oncolytic adenovirus OAd-shPDL1 (1-4.5K) and the control virus group (C-4.5K) did not show significant toxicity to NOD-SCID deficient mice (see FIG. 40).

Next, BALB/C nude mice were subcutaneously inoculated (the number of cells inoculated subcutaneously per mouse was $5\times10^6$ cells) human colon cancer cells HCT116 to prepare the tumor-bearing mouse model which was used to verify the growth inhibitory effect of oncolytic adenovirus OAd-shPDL1 (1-4.5K) on HCT116. Control oncolytic virus C-4.5K was used as a negative control virus. Selecting twenty-five tumor-bearing mice with subcutaneously inoculated tumor meeting the tumor volume requirement (tumor volume was 90-120 mm$^3$) and dividing into five groups in the manner of randomized block, five mice per group. The first group was a control group (Blank Control) wherein each mouse was injected with 100 μl of adenovirus preservation solution every time. The second group was a medium-dose control oncolytic virus group (C-4.5K (medium)) wherein each mouse was injected with 100 μl of viral suspension containing $1\times10^8$ PFU oncolytic virus C-4.5K every time. The third group was a low-dose oncolytic virus group (1-4.5K (low)) wherein each mouse was injected with 100 μl of viral suspension containing $1\times10^7$ PFU oncolytic virus 1-4.5K every time. The fourth group was a medium-dose oncolytic virus group (1-4.5K (medium)) wherein each mouse was injected with 100 μl of viral suspension containing $1\times10^8$ PFU oncolytic virus 1-4.5K every time. The fifth group is a high-dose oncolytic virus group (1-4.5K (high)) wherein each mouse was injected with 100 μl of viral suspension containing $1\times10^9$ PFU oncolytic virus 1-4.5K every time, A total of five administrations were performed throughout the experiment, and the drug was administered every other day. The first administration started from the day of grouping (recorded as day 0). Tumor diameter and the body weight of the mice were measured twice a week. After the day 28, the mice were sacrificed and tumors were taken for photographing. The experimental results were shown in FIGS. 42, 43, 44 and 45, respectively.

Figure 43:
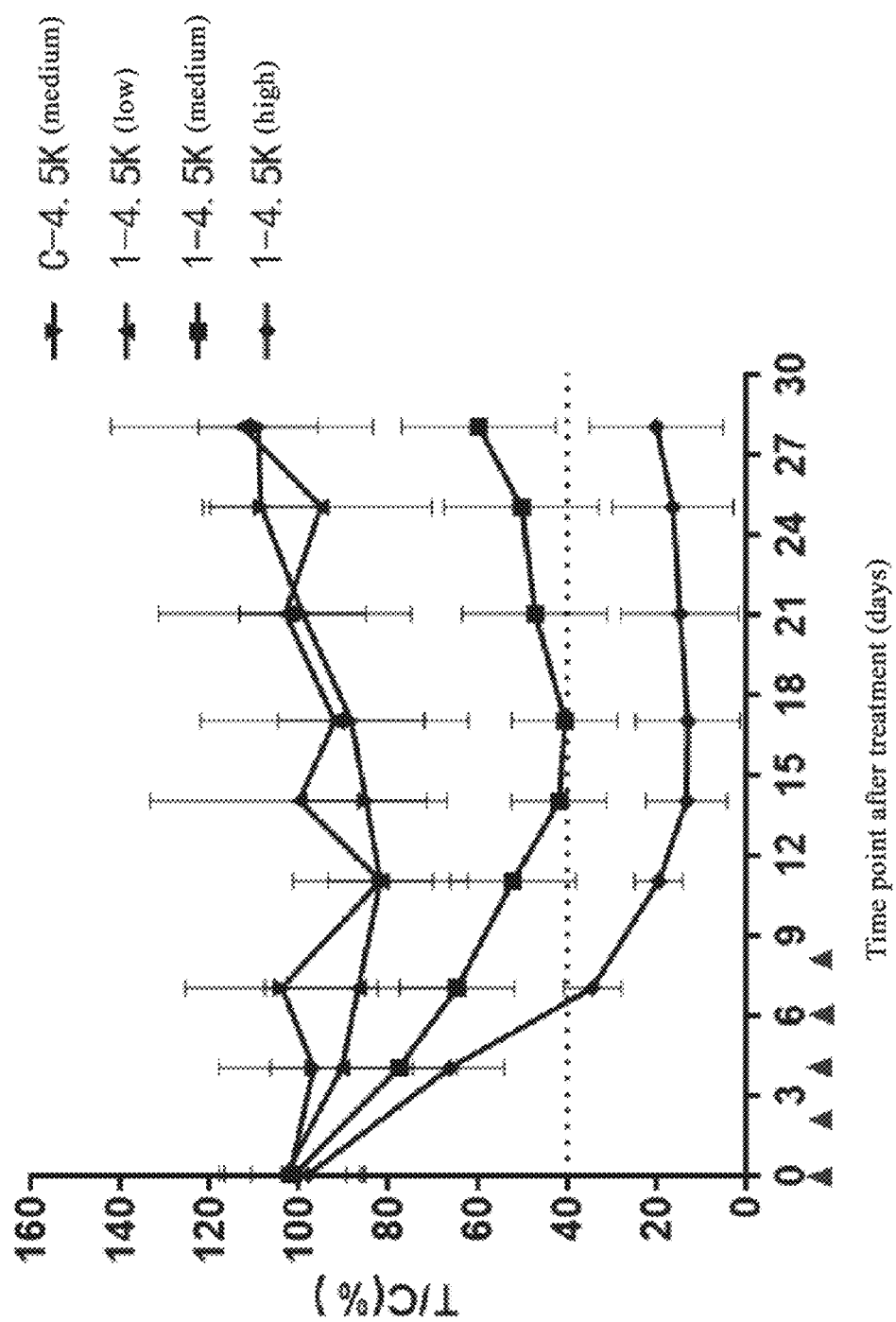
FIG. 43 shows the change of relative proliferation rate (T/C) of tumor in HCT116-bearing BALB/C nude mice treated with oncolytic adenovirus OAd-shPDL1 #1-4.5K (1-4.5K) and system control virus OAd-C-4.5K (C-4.5K) constructed according to the present disclosure in Example 7; gray triangles on the abscissa indicate the time points of administration, and the abscissa represents the time (day) after administration, and the ordinate represents T/C (%).
Figure 44:
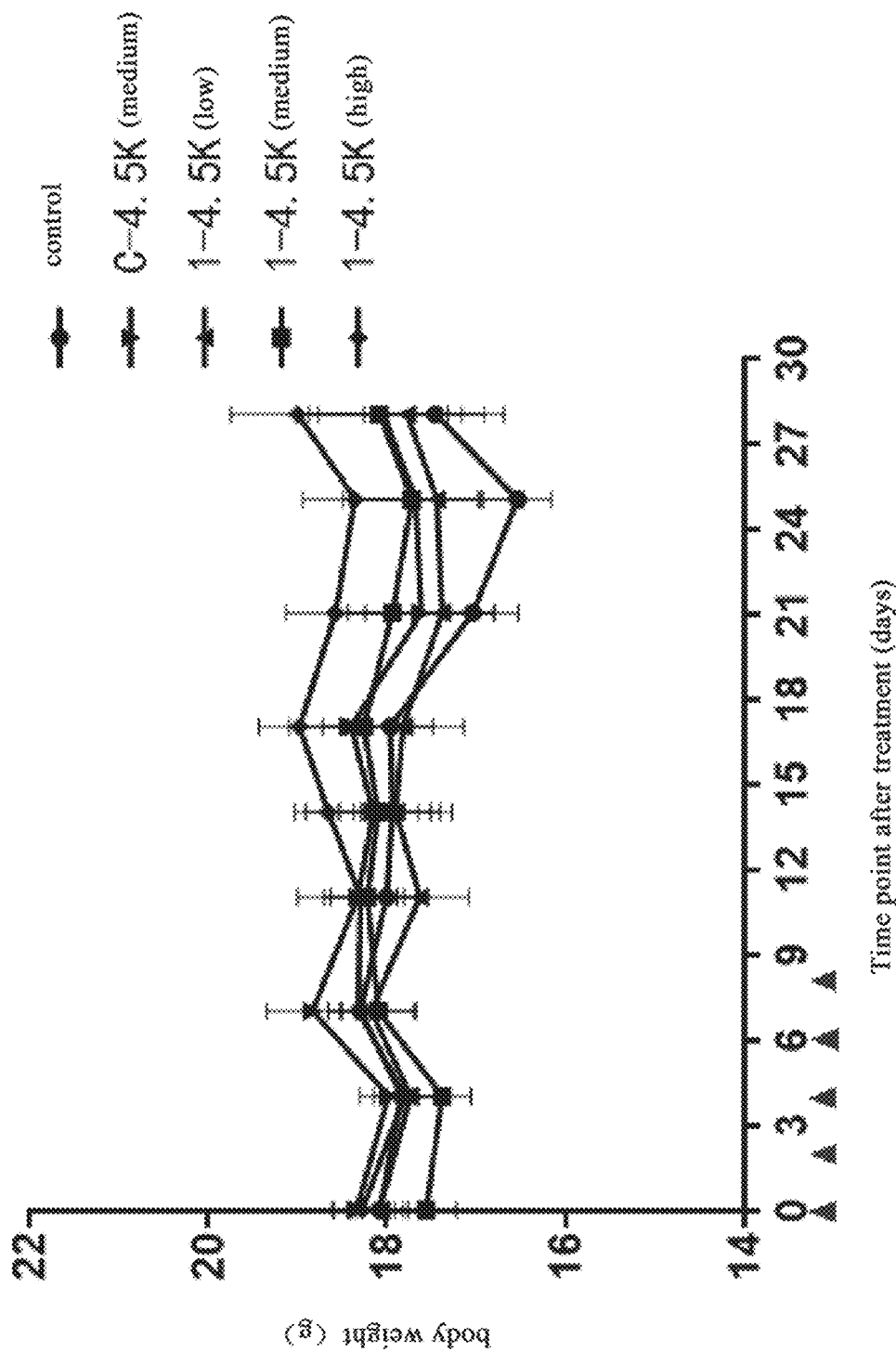
FIG. 44 shows the change of body weight of HCT116-bearing BALB/C nude mice treated with oncolytic adenovirus OAd-shPDL1 #1-4.5K (1-4.5K) and system control virus OAd-C-4.5K (C-4.5K) constructed according to the present disclosure in Example 7; gray triangles on the abscissa indicate the time points of administration, and the abscissa represents the time (day) after administration, and the ordinate represents body weight (g).
Figure 45:
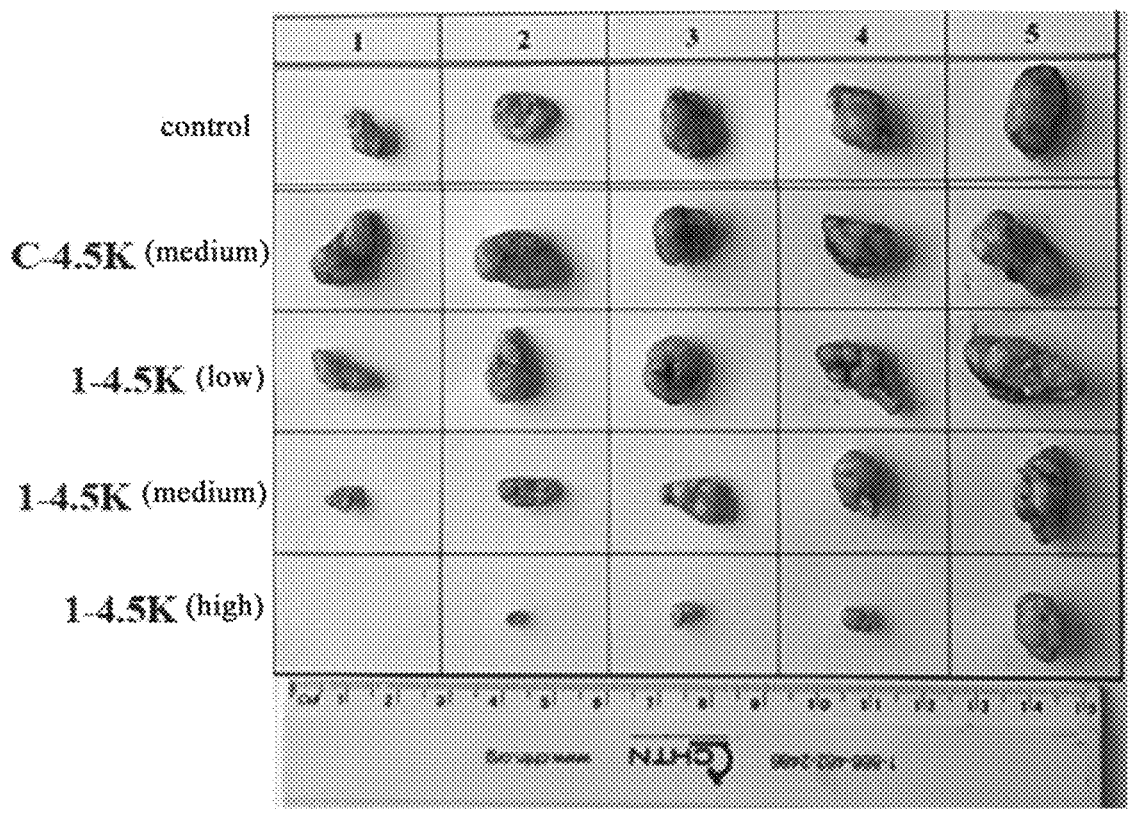
FIG. 45 shows the photographs of tumors taken from mice after sacrifice in Example 7, wherein the mice were HCT116-bearing BALB/C nude mice treated with oncolytic adenovirus OAd-shPDL1 #1-4.5K (1-4.5K) and system control virus OAd-C-4.5K (C-4.5K) constructed according to the present disclosure.
Figure 46:
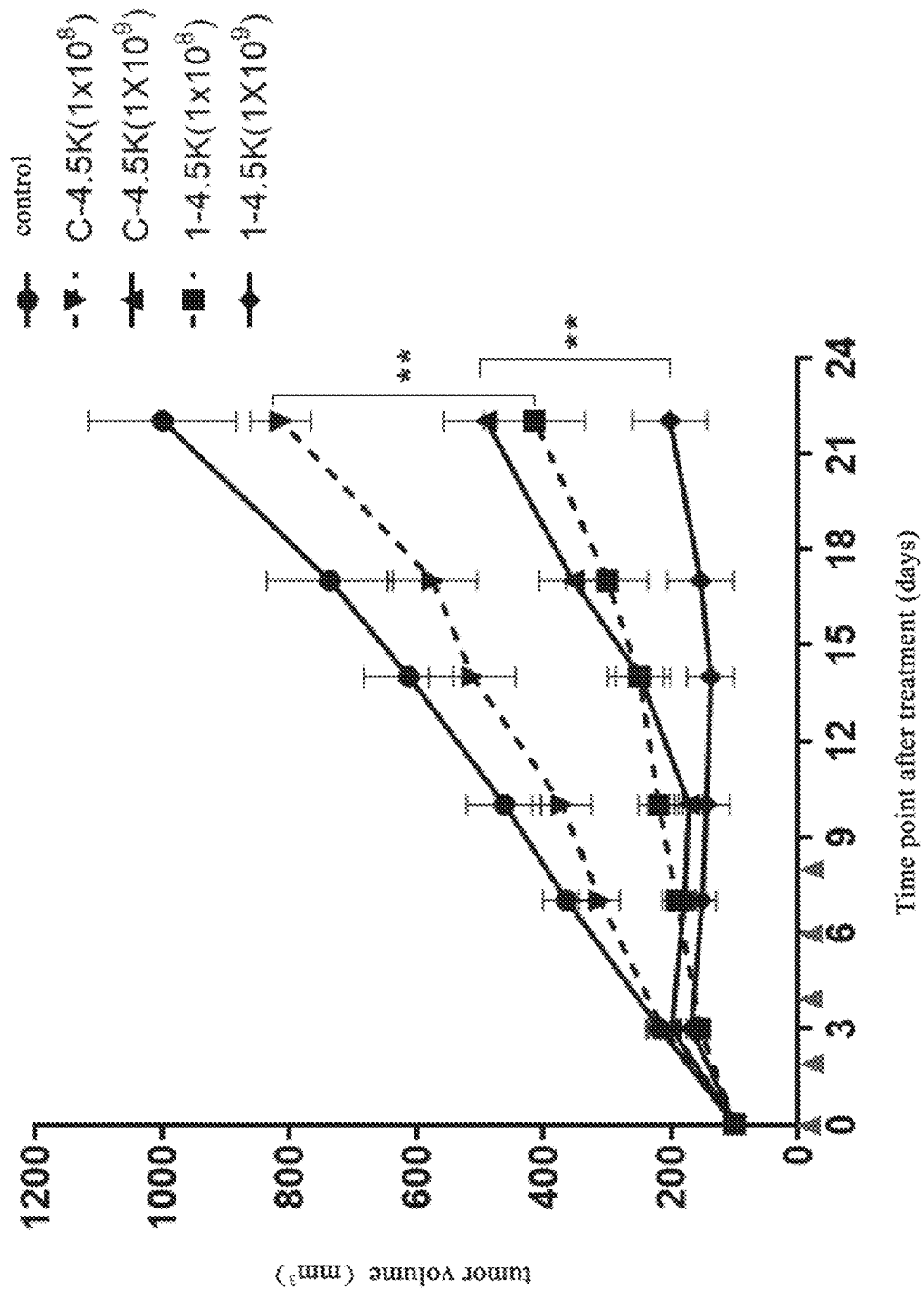
FIG. 46 shows the change of tumor volume in HCT116-bearing BALB/C nude mice treated with oncolytic adenovirus OAd-shPDL1 #1-4.5K (1-4.5K) and system control virus OAd-C-4.5K (C-4.5K) constructed according to the present disclosure in Example 8; gray triangles on the abscissa indicate the time points of administration, and the abscissa represents the time (day) after administration, and the ordinate represents Tumor volume ($mm^3$).

Consider the above results comprehensively: in the experiment of oncolytic adenovirus OAd-shPDL1 (1-4.5K) being used to treat HCT116 tumor cells inoculated subcutaneously in BALB/C nude mice, both the high-dose group and the medium-dose group showed excellent anti-tumor effect (see FIG. 42), in which the relative tumor proliferation rate (T/C %) of the high-dose group achieved less than 40%, and the relative tumor growth rate (T/C %) of the medium-dose group also achieved less than 40% during the experiment (see FIG. 43). More important, the tumors on the back of the nude mice of the high-dose group showed obvious "oncolytic" phenomenon, i.e., the surface was ulcerated and the tumor tissue at the initial inoculation site was basically removed after the ulcerated part scabbing and falling off. From the perspective of the animal's physical condition and body weight, except one nude mouse of the high-dose group whose tumor cells were attached to the muscle of the spine of the back resulting in the inhibitory effect of OAd-shPDL1 (1-4.5K) was not very obvious, the growth of tumor cells inoculated on the back was effectively inhibited hi other four nude mice of the high-dose group and the bodies of these four nude mice were plumper and stronger than the nude mice of other groups. Among the four nude mice, the tumor cells inoculated on the back of two nude mice were invisible by the naked eye after the treatment with OAD-shPDL1 (1-4.5K) (see FIGS. 44 and 45). By comparing the same dose of backbone control oncolytic virus group (C-4.5K) and the OAd-shPDL1 (1-4.5K) medium-dose group, it was found that the growth of tumors inoculated subcutaneously in nude mice of the OAd-shPDL1 (1-4.5K) medium-dose group also showed a relatively significant inhibitory effect (see FIGS. 42, 43 and 45). Therefore, it is believed that the decrease of HPDL1 expression level in tumor cells caused by shPDL1 expressed by the shPDL1 expression cassette of the OAd-shPDL1 (1-4.5K) medium-dose group played a key role in inhibiting tumor growth. Nude mice of the virus preservation solution group showed significant weight loss and most of them showed malignant wasting habitus related to tumor growth.

Example 8: Verification of Growth Inhibition of Oncolytic Adenovirus OAd-shPDL1 on Human Tumor Cells HCT116 Subcutaneously Inoculated into BALB/C Nude Mice To further confirm the effective dose of OAd-shPDL1 (1-4.5K) for the growth inhibition on HCT116 cells subcutaneously inoculated into BALB/C nude mice, this example expanded the sample size of the animal model to further verify the effective dose of OAd-shPDL1 (1-4.5K). The human colon cancer cell HCT116 was inoculated into subcutaneous of the BALB/C nude mice to prepare a tumor-bearing mouse model. The cell inoculation amount for each nude mouse was $5 \times 10^6$ cells. Selecting thirty-five tumor-bearing mice with subcutaneously inoculated tumor meeting the tumor volume requirement (tumor volume was 80-130 $mm^3$) and dividing into five groups in the manner of randomized block, seven mice per group. The first group was a control group (Blank Control) wherein each mouse was injected with 100 μl of adenovirus preservation solution (i.e., 10 mM Tris solution (pH 7.4) containing 1 mM of $MgCl_2$ and 10% glycerol) every time. The second group was a medium-dose control oncolytic virus group (C-4.5K ($1 \times 10^8$)) wherein each mouse was injected with 100 μl of viral suspension containing $1 \times 10^8$ PFU oncolytic virus C-4.5K every time. The third group was a high-dose control oncolytic virus group (C-4.5K ($1 \times 10^9$)) wherein each mouse was injected with 100 μl of viral suspension containing $1 \times 10^9$ PFU oncolytic virus C-4.5K every time. The fourth group was a medium-dose oncolytic virus group (1-4.5K ($1 \times 10^8$)) wherein each mouse was injected with 100 μl of viral suspension containing $1 \times 10^8$ PFU oncolytic virus 1-4.5K every time. The fifth group is a high-dose oncolytic virus group (1-4.5K ($1 \times 10^9$)) wherein each mouse was injected with 100 μl of viral suspension containing $1 \times 10^9$ PFU oncolytic virus 1-4.5K every time. A total of five administrations were performed throughout the experiment and the drug was administered every other day. The first administration started from the day of grouping (recorded as day 0). Tumor diameters and the body, weight of the mice were measured twice a week. On the Day 25, since the tumors of the tumor-bearing nude mice of the control group and the control oncolytic virus group were ulcerated, the experiment was terminated and all thirty-five mice were sacrificed. The tumor was taken for weighing and photographing and, together with the blood and spleen of the same mouse, was prepared into cell suspension, respectively. Flow cytometry antibodies (anti-mouse CD49b antibody and anti-mouse CD3 antibody, both of which were purchased from Ebioscience Company) for detecting NK cells and T cells of BALB/C nude mouse were added thereinto and after staining, FACS was performed to analyze the change of the proportion of NK and T cells of tumor cells in tumor, blood and spleen. The experimental results were shown in FIG. 46, FIG. 47, FIG. 48, FIG. 49, FIG. 50 and FIG. 51, respectively.

Preparation of blood cell suspension: After removing the eyeball of the mouse, the blood was taken and added to an anticoagulation tube, shaken and mixed, and then paced on ice. The supernatant was discarded after the blood was centrifuged at 500×g for 5 minutes, and then red blood cell lysis solution (purchased from Tiangen Biochemical Technology (Beijing) Co., Ltd., Cat. No.: #122-02) was added to the cell precipitate which was thoroughly mixed and reacted at room temperature for 10-15 minutes. After centrifugation at 500×g for 5 minutes again, the supernatant was discarded and the cell precipitate was retained. The cells were resuspended in PBS containing 1% BSA and centrifuged at 500×g for 5 minutes, and then the supernatant was discarded to retain the cell precipitate. The cell precipitate was divided into two parts. One part was used as a control without any treatment, and the other part was added with the anti-BALB/C mouse CD3 and CD49b flow cytometry antibodies, mixed and reacted at room temperature for 30 minutes in the dark, and then subjected to FACS.

Preparation of spleen cell suspension: The mice were dissected and the spleen of the mice was taken and placed in a 1.5 ml of centrifuge tube and temporarily stored on ice. 5 ml of a PBS solution containing 1% BSA were added to a clean 6 cm culture dish. The spleen was wrapped with a nylon mesh to be squeezed and milled in the culture dish to fully release the spleen cells. The supernatant was discarded after the cell suspension was centrifuged at 500×g for 5 minutes, and red blood cell lysis solution was added to the cell precipitate which was thoroughly mixed and reacted at room temperature for 10-15 minutes, After centrifugation at 500×g for 5 minutes again, the supernatant was discarded and the cell precipitate was retained. The cells were resuspended in PBS containing 1% BSA and centrifuged at 500×g for 5 minutes, and then the supernatant was discarded to retain the cell precipitate. The cell precipitate was divided into two parts. One part was used as a control without any treatment, and the other part was added with the anti-BALB/C mouse CD3 and CD49b flow cytometry antibodies, mixed and reacted at room temperature for 30 minutes in the dark, and then subjected to FACS.

Preparation of tumor tissue cell suspension: The mice were dissected and the subcutaneous tumor was taken and placed in a 1.5 ml of centrifuge tube, temporarily stored on ice. Cutting each tumor tissue and taking equal volume of pieces and placing in another set of centrifuge tubes. Then 500 μl of collagenase was added. The tumor was cut into small pieces by ophthalmic scissors and reacted at 37° C. for 30 minutes. The supernatant was discarded after the cell suspension was centrifuged at 500×g for 5 minutes, and red blood cell lysis solution was added to the cell precipitate, thoroughly mixed and reacted at room temperature for 10-15 minutes. After centrifugation at 500×g for 5 minutes again, the supernatant was discarded and the cell precipitate was retained. The cells were resuspended in PBS containing 1% BSA and centrifuged at 500×g for 5 minutes, and then the supernatant was discarded to retain the cell precipitate. The cell precipitate was divided into two parts. One part was used as a control without any treatment, and the other part was added with the anti-BALB/C mouse CD3 and CD49b flow cytometry antibodies, mixed and reacted at room temperature for 30 minutes in the dark, and then subjected to FACS.

Figure 47:
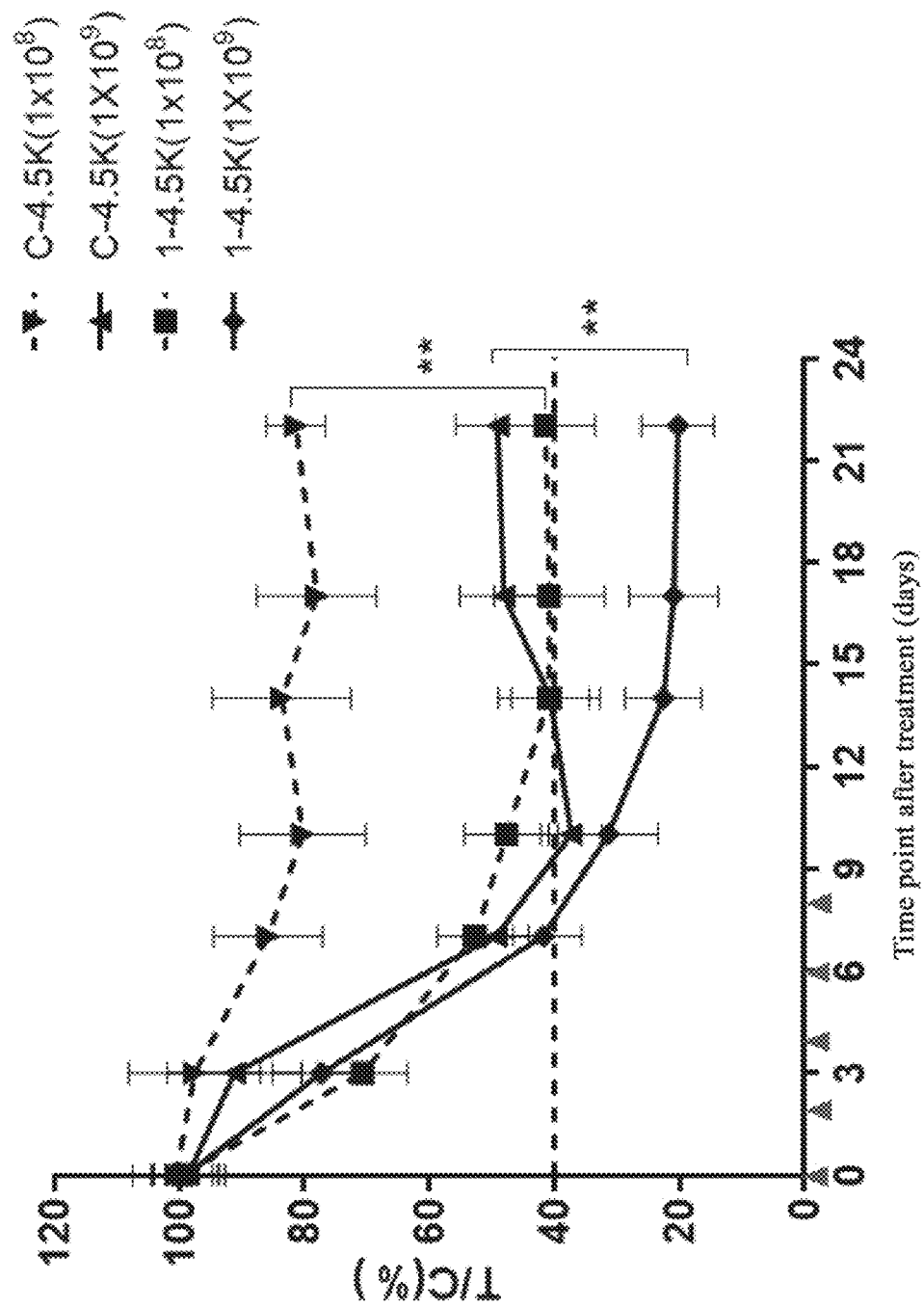
FIG. 47 shows the change of relative proliferation rate (T/C) in HCT116-bearing BALB/C nude mice treated with oncolytic adenovirus OAd-shPDL1 #1-4.5K (1-4.5K) and system control virus OAd-C-4.5K (C-4.5K) constructed according to the present disclosure in Example 8; gray triangles on the abscissa indicate the time points of administration, and the abscissa represents the time (day) after administration, and the ordinate represents T/C (%).
Figure 48:
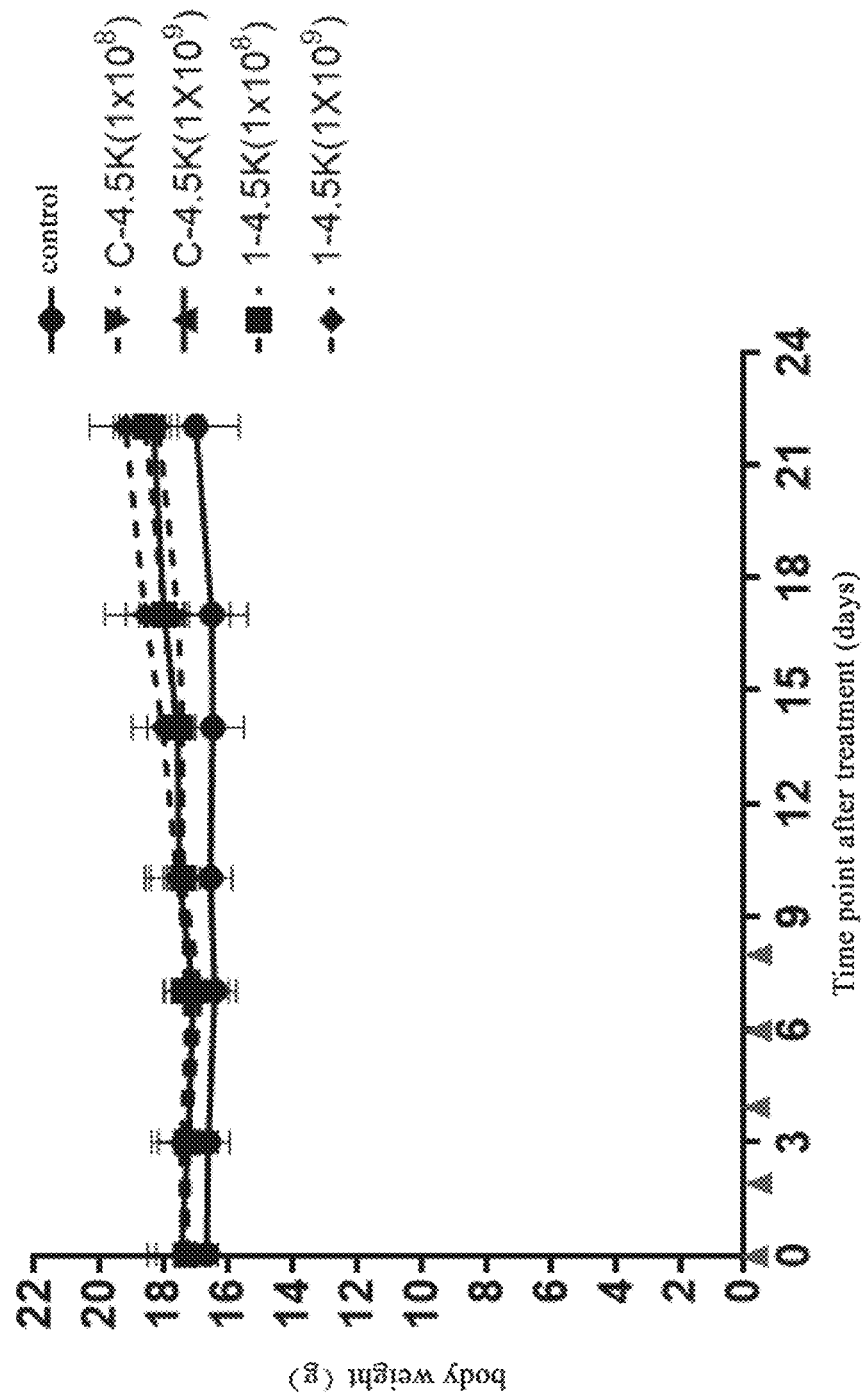
FIG. 48 shows the change of body weight of HCT116-bearing BALB/C nude mice treated with oncolytic adenovirus OAd-shPDL1 #1-4.5K (1-4.5K) and system control virus OAd-C-4.5K (C-4.5K) constructed according to the present disclosure in Example 8; gray triangles on the abscissa indicate the time points of administration, and the abscissa represents the time (day) after administration, and the ordinate represents body weight (g).
Figure 49:
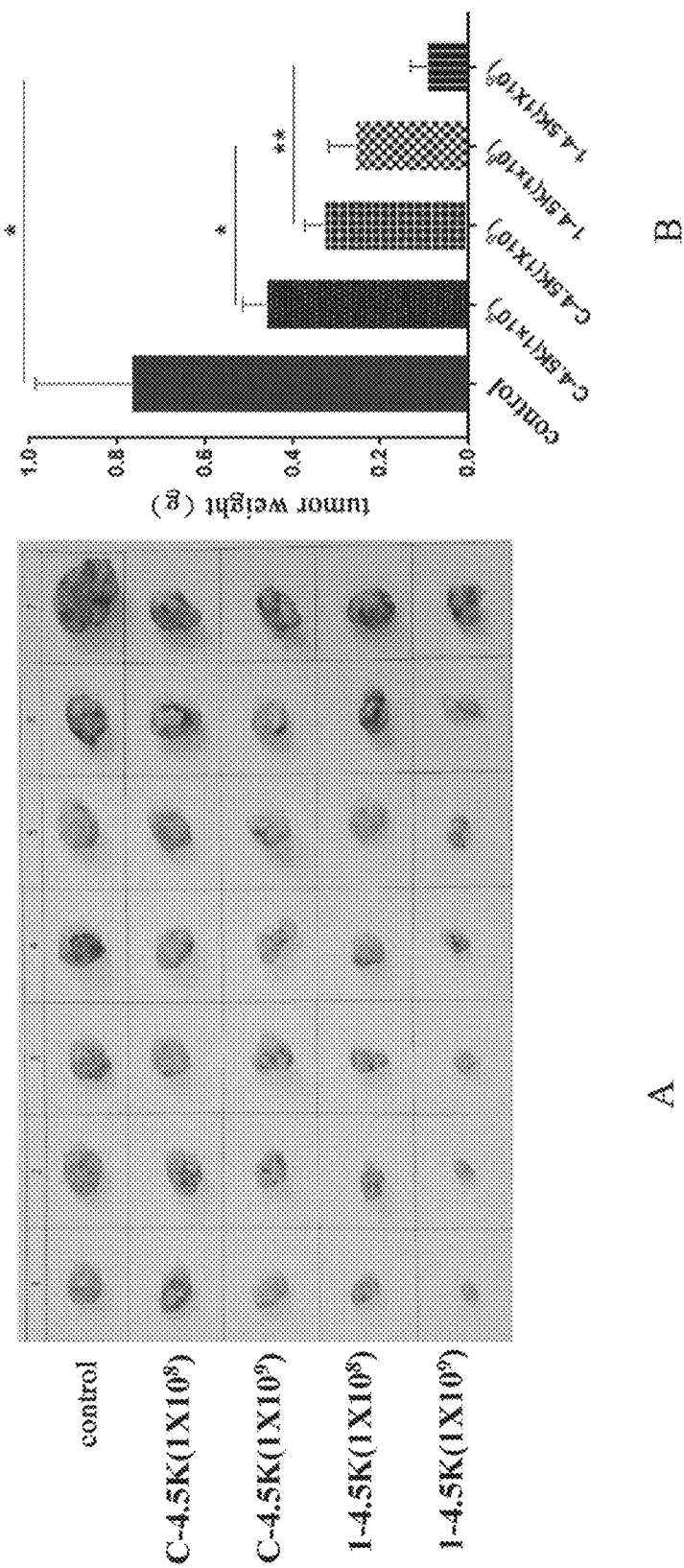
FIG. 49 shows photographs of tumors taken from sacrificed mice (FIG. A) and statistical result of tumor weigh in each group (FIG. B) in Example 8, wherein the mice were HCT116-bearing BALB/C nude mice treated with oncolytic adenovirus OAd-shPDL1 #1-4.5K (1-4.5K) and system control virus OAd-C-4.5K (C-4.5K) constructed according to the present disclosure. In FIG. B, the abscissa represents different groups, and the ordinate represents tumor weight (g).
Figure 50:
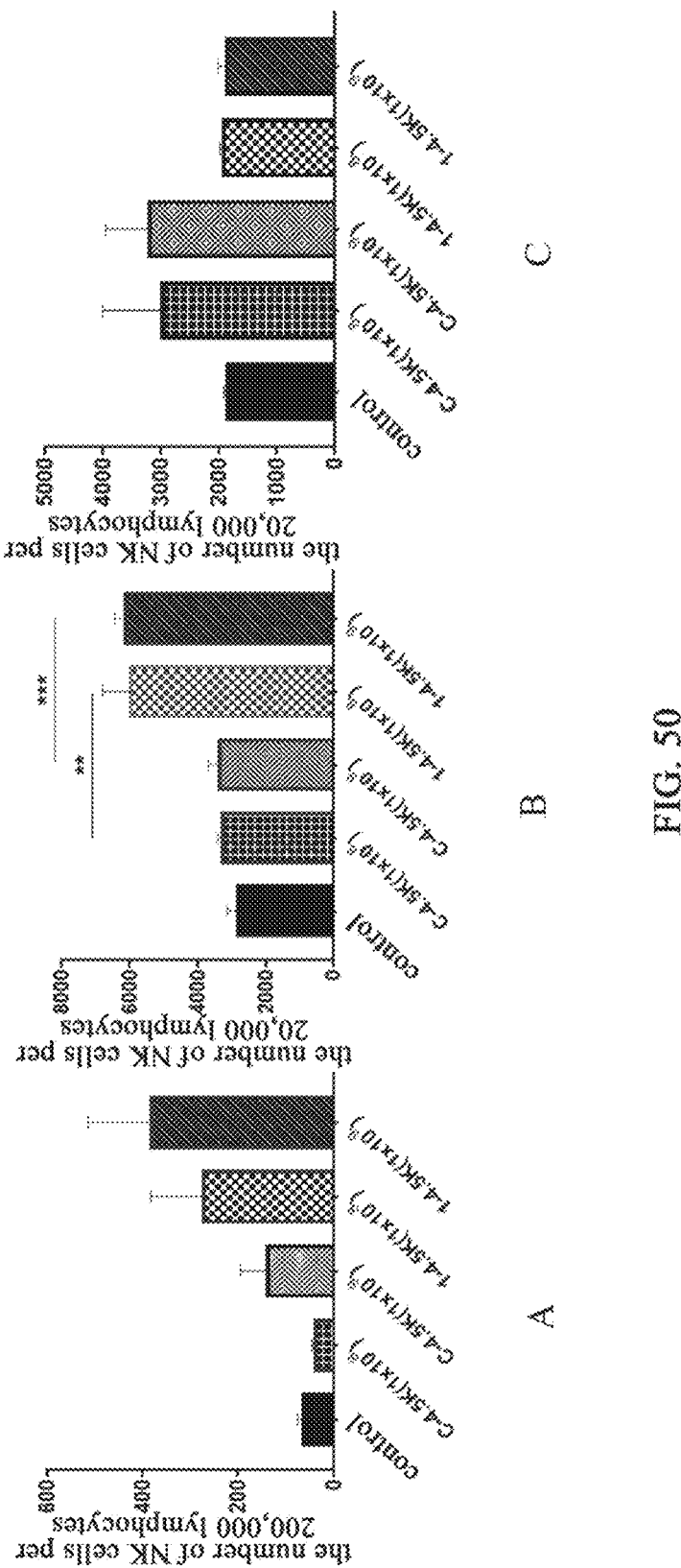
FIG. 50 shows the normalized statistical results of the NK cell number in tumor, blood and spleen of each group of mice measured by FACS in Example 8, wherein the mice were HCT116-bearing BALB/C nude mice treated with oncolytic adenovirus OAd-shPDL1 #1-4.5K (1-4.5K) and system control virus OAd-C-4.5K (C-4.5K) constructed according to the present disclosure. FIG. A shows the results in tumors, FIG. B shows the results in blood, and FIG. C shows the results in spleen. The abscissa in each graph represents the different groups set in the experiment, and the ordinate represents the number of NK cells after normalization.
Figure 51:
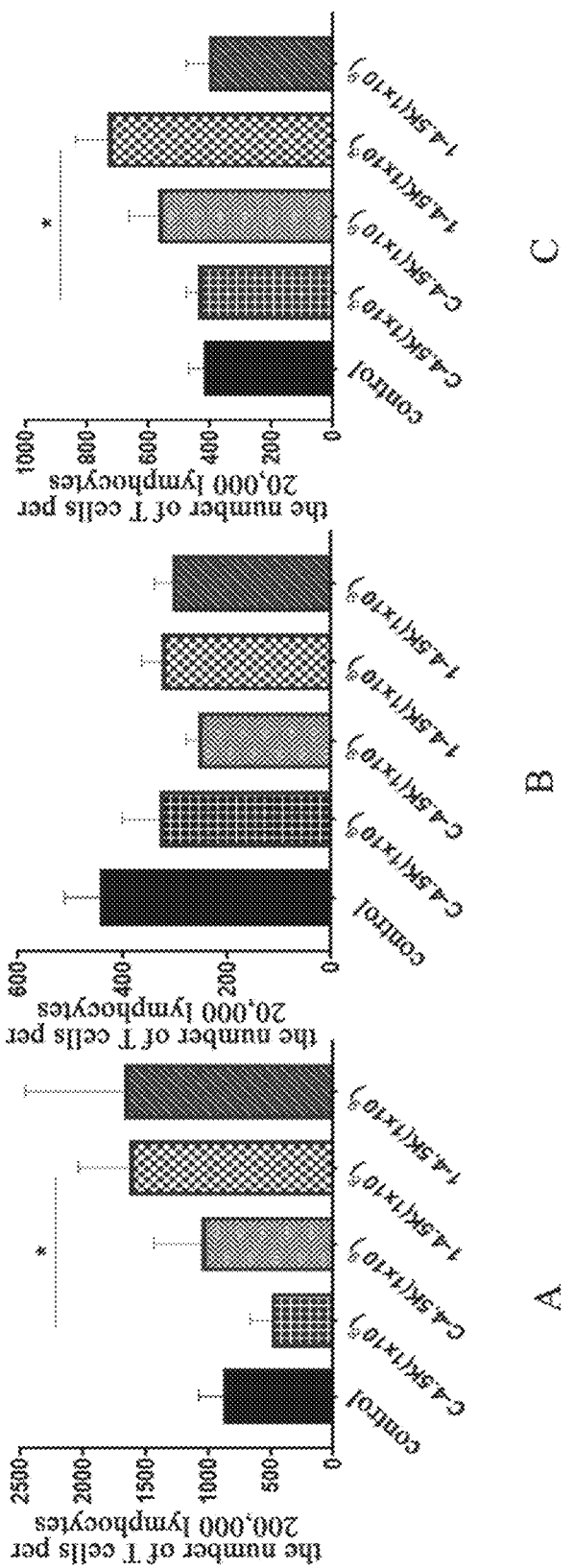
FIG. 51 shows the normalized statistical results of the T cell number in tumor, blood and spleen of each group of mice measured by FACS in Example 8, wherein the mice were HCT116-bearing BALB/C nude mice treated with oncolytic adenovirus OAd-shPDL1 #1-4.5K (1-4.5K) and system control virus OAd-C-4.5K (C-4.5K) constructed according to the present disclosure. FIG. A shows the results in tumors, FIG. B shows the results in blood, and FIG. C shows the results in spleen. The abscissa in each graph represents the different groups set in the experiment, and the ordinate represents the number of T cell after normalization.

Consider the above results comprehensively: in the experiment of oncolytic adenovirus OAd-shPDL1 (1-4.5K) being used to treat HCT116 tumor cells inoculated subcutaneously in BALB/C nude mice, both the high-dose group and the medium-dose group showed excellent anti-tumor effect (See FIG. 46), in which the relative tumor proliferation rate (T/C %) of the medium-dose group reached 40% and the high-dose group reached less than 40% (see FIG. 47). By comparing the inhibitory effect on the growth of the HCT116 cell achieved by the control virus C-4.5K ($1\times10^8$) group and by the interest oncolytic virus 1-4.5K ($1\times10^8$) group, it was found that the oncolytic virus 1-4.5K showed superior growth inhibitory effect, and there was a very significant difference between the two groups in terms of the tumor volume by statistical analyzation. By comparing the inhibitory effect on the growth of the HCT116 cell achieved by the control virus C-4.5K ($1\times10^9$) group and the interest oncolytic virus 1-4.5K ($1\times10^9$) group, it was found that in the initial stage of the administration, both viruses showed a very strong growth inhibitory effect on the subcutaneously inoculated HCT116, but on the Day 10 of the experiment, unlike the 1-4.5K group, C-4.5K group did not exhibit sustained inhibitory effect on tumor growth, wherein the subcutaneous tumors of nude mice of the C-4.5K ($1\times10^9$) group began to grow, while the subcutaneous tumors of nude mice of the 1-4.5K ($1\times10^9$) group were inhibited sustainedly until the Day 17 of the experiment. There was also a significant difference in tumor volume between the two groups. Analyzing the above results comprehensively, it is believed that C-4.5K and 1-4.5K oncolytic viruses fully exhibited the characteristic of oncolytic virus. Moreover, since 1-4.5K can express shPDL1, it showed longer inhibitory effect on the growth of HCT116 cells compared with C-4.5K. This example fully reflected that shPDL1 expressed by oncolytic virus 1-4.5K changes the expression level of hPDL1 in human tumor cells, which may attenuate or eliminate the immunosuppressive effect around the tumor cells, so as to activate surrounding immune cells. Accordingly, combined killing effect on tumors was achieved. There was no significant change in body weight of all five groups of mice, indicating that no significant toxicity to BALB/C nude mice was found in both of the oncolytic adenovirus (see FIG. 48). After photographing and weighing the tumors of each group of mice (see FIG. 49), it was found that there was a significant difference between the tumor weights of the 1-4.5K experimental group and the C-4.5K experimental group. It was found by FACS analysis on NK and T cells in tumor, blood and spleen that NK cells in tumor tissues and blood of the mice administered with 1-4.5K oncolytic virus were enhanced much more than that in the control group (Control group) and C-4.5 control oncolytic virus group, wherein NK cells in the blood of the 1-4.5K oncolytic virus group were twice as high as that in the blood of the control group, and NK cells in tumor tissues were 5 times higher than that in the control group. NK cells in the spleens of each group of animals did not change significantly (see FIG. 50). Analysis on T cells revealed that the proportion of T cells in the blood of each group did not change significantly, but T cells in the spleens and tumor tissues of the 1-4.5K ($1\times10^8$) experimental group were significantly increased compared to T cells in the same tissues of the C-4.5K ($1\times10^8$) group (see FIG. 51).

Comprehensive analysis of the above experimental results (see Examples 7 and 8) showed that when using the same oncolytic adenovirus OAd-shPDL1 (1-4.5K) to treat human colon cancer cells HCT116 inoculated subcutaneously in two kinds of immunodeficiency mice with different genetic background, a significant difference in tumor inhibitory effect was obtained. OAd-shPDL1 (1-4.5K) showed excellent inhibitory effect on tumor growth and effect on tumor clearance hi the subcutaneously inoculated HCT116 in BALB/C nude mice, while the anti-tumor effect of the same dose ($1\times10^9$) of OAd-shPDL1 (1-4.5K) oncolytic virus on the same kind of cells inoculated subcutaneously in NOD-SCID immunodeficient mice was not obvious. When HCT116 inoculated subcutaneously in BALB/C nude mice was treated with another backbone control virus (C-4.5K) that did not contain the shPDL1 expression cassette at the same concentration ($1\times10^9$), a similar tumor inhibitory effect as OAd-shPDL1 (1-4.5K) oncolytic virus was exhibited only at the initial stage of the administration. However, unlike OAd-shPDL1 (1-4.5K), the backbone control virus (C-4.5K) can not inhibit the tumor growing sustainedly after stopping administration. Generally, tumor cells will highly express ligands such as PDL1 or PDL2 on their surface in order to avoid being killed and eliminated by the body's immune system. The binding of these ligands to PD-1 will lead to tyrosine phosphorylation of the intracellular domain of PD-1 and recruit tyrosine phosphatase SHP-2, thereby reducing phosphorylation of the TCR signaling pathway, reducing activation signals downstream of the TCR pathway, activation of T cells and cytokine production. Therefore, an immunosuppressive microenvironment will be formed around the tumors in which immune cells are in an inactive state. In addition, from the viewpoint of immunodeficient mouse strains, NOD-SCID immunodeficient mice have higher level of immunodeficiency, wherein T cells are lack in the body, B cells exist but lack of function and the function of NK cell is extremely low; while the degree of immunodeficiency of BALB/C nude mice is low, wherein T cells are also lack in the body and B cells exist but lack of function. However, the mice retain NK cells, macrophages and antigen-presenting cells mainly composed of dendritic cells, with intact functions. It has been reported in a literature that NK, macrophages or dendritic cells in mice may play an important combined killing effect during the process of inhibiting tumor growth (see, for example, the following scientific literature: "Kevin C. Barry, et al., A natural killer-dendritic cell axis defines checkpoint therapy-responsive tumor microenvironments. Nat Med. 2018 Jun. 25.doi: 10.1038/s41591-018-0085-8."). Oncolytic adenovirus OAd-shPDL1 (1-4.5K) and its backbone control virus C-4.5K differs in that the former contains an expression cassette that can express shPDL1, which can express shPDL1 in the infected tumor cells. The shPDL1 reduces hPDL1 level in human tumor cells, which further attenuates or removes the immunosuppressive state in the environment around tumors. Eventually, it will maintain a longer inhibition on tumor growth. In addition, it has been reported in literatures that PD1 on the surface of mouse immune cells and PDL1 on the surface of human cells can bind to each other and transmit immunosuppressive signals; in turn, the expression of hPDL1 is reduced in human tumor cells because of shPDL1 expression (see, for example, the following scientific Literatures: "David Yin-wet Lin, et al. The PD-1/PD-L1 complex resembles the antigen-binding Fv domains of antibodies and T cell receptors. Proc Nati Acad Sci USA. 2008 Feb. 26; 105(8):3011-6."; "Clement Viricel. et al. Human PD-1 binds differently to its human ligands:A comprehensive modeling study. J Mol Graph Model. 2015 April; 57:131-42"; or "Aaron T. Mayer, et al. Practical ImmunoPET radiotracer design considerations for human immune checkpoint imaging. J Nuc Med. 2017 April; 58(4): 538-546."). Therefore, it is believed that shPDL1 expressed by oncolytic adenovirus OAd-shPDL1 (1-4.5K) in human tumor cells HCT116 resulted in a decrease in hPDL1 expression in tumor cells, which weakened and relieved the inhibitory effect on immune cells (NK, macrophages, or dendritic cells) surrounding tumor tissues, thereby exhibiting a sustained ability to inhibit the growth of HCT116.

The results of this part are also consistent with the above synergistic; effect showed by the oncolytic virus OAd-shPDL1 (1-4.5K) and human NK cells in the combined killing process of tumor cells in vitro.

What is claimed is:

1. An isolated recombinant oncolytic adenovirus, wherein the recombinant oncolytic adenovirus is a selectively replicating oncolytic adenovirus and the genome of the recombinant oncolytic adenovirus is integrated with a coding sequence of an exogenous shRNA capable of inhibiting the expression of PDL1 in tumor cells; wherein the coding sequence of the exogenous shRNA is as shown in any one of SEQ ID NOs. 16, 19, and 22.

2. The recombinant oncolytic adenovirus according to claim 1, wherein the recombinant oncolytic adenovirus is obtained by genetically modifying an adenovirus type 5.

3. A pharmaceutical composition, wherein the pharmaceutical composition comprises the recombinant oncolytic adenovirus according to claim 1 as an active ingredient, and a pharmaceutically acceptable excipient.

4. The pharmaceutical composition according to claim 3, wherein the pharmaceutical composition comprises the recombinant oncolytic adenovirus in a dose ranging from $5 \times 10^7$ to $5 \times 10^{12}$ vp/day.

5. The pharmaceutical composition according to claim 3, wherein the recombinant oncolytic adenovirus is formulated to be administered via intratumoral injection or administered intravenously.

6. A vector for preparing the recombinant oncolytic adenovirus according to claim 1, wherein the vector comprises a coding sequence of an exogenous shRNA under the control of a promoter, and the coding sequence of the shRNA is as shown in any one of SEQ ID NOs. 16, 19 and 22.

7. The vector according to claim 6, wherein the vector uses pShuttle as a basic backbone, and the basic backbone orderly comprises an operatively linked promoter controlling the expression of the coding sequence of the exogenous shRNA, the coding sequence of the exogenous shRNA, a promoter controlling the expression of the coding sequence of the E1A gene, and the coding sequence of the E1A gene.

8. A host cell comprising the vector according to claim 6.

9. The host cell according to claim 8, wherein the host cell stably expresses the vector.

10. A pharmaceutical composition, wherein the active ingredients of the pharmaceutical composition comprise the recombinant oncolytic adenovirus according to claim 1 and NK cells.

11. The pharmaceutical composition according to claim 10, wherein the recombinant oncolytic adenovirus and the NK cells are present separately in the pharmaceutical composition without being mixed together.

12. The pharmaceutical composition according to claim 10, wherein the pharmaceutical composition comprises the recombinant oncolytic adenovirus in a dose ranging from $5 \times 10^7$ to $5 \times 10^{12}$ vp/day and comprises the NK cells in a dose ranging from $1 \times 10^9$ to $3 \times 10^9$ cells/day.

13. The pharmaceutical composition according to claim 10, wherein the NK cells are selected from autologous NK cells and allogeneic NK cells.

14. The pharmaceutical composition according to claim 13, wherein the NK cells are in vitro expanded autologous NK cells or in vitro expanded allogeneic NK cells.

15. The pharmaceutical composition according to claim 10, wherein the recombinant oncolytic adenovirus is formulated to be administered via intratumoral injection or administered intravenously and the NK cells are formulated to be administered intravenously.

16. An isolated shRNA, wherein the coding sequence of the shRNA is as shown in any one of SEQ ID NOs. 16, 19, and 22, and the shRNA is capable of inhibiting the expression of PDL1 in tumor cells.

17. A kit of combinational drugs with synergistic effects for treatment of tumors and/or cancers, comprising separate containers containing respectively and independently a recombinant oncolytic adenovirus and NK cells, and instructions specifying the timing and routes of administration; wherein the recombinant oncolytic adenovirus is a selectively replicating oncolytic adenovirus and the genome of the recombinant oncolytic adenovirus is integrated with a coding sequence of an exogenous shRNA capable of inhibiting the expression of PDL1 in tumor cells; wherein the genome of the recombinant oncolytic adenovirus is lack of the E1B19K gene, the E1B55K gene, and all the genes in E3 region; and wherein the genome of the recombinant oncolytic adenovirus comprises a coding sequence of the E1A gene and the coding sequence of the E1A gene is under the control of a promoter; wherein the coding sequence of the exogenous shRNA is as shown in any one of SEQ ID NOs. 16, 19, and 22.

18. The kit according to claim 17, wherein the coding sequence of the E1A gene is under the control of a CMV promoter.

19. The kit according to claim 17, wherein the recombinant oncolytic adenovirus is obtained by genetically modifying an adenovirus type 5.

20. The kit according to claim 17, wherein the vector for preparing the recombinant oncolytic adenovirus comprises a coding sequence of an exogenous shRNA under the control of a promoter, and the coding sequence of the shRNA is as shown in any one of SEQ ID NOs. 16, 19 and 22.

21. The kit according to claim 20, wherein the vector uses pShuttle as a basic backbone, and the basic backbone orderly comprises an operatively linked promoter controlling the expression of the coding sequence of the exogenous shRNA, the coding sequence of the exogenous shRNA, a promoter controlling the expression of the coding sequence of the E1A gene, and the coding sequence of the E1A gene.

22. The kit according to claim 20, wherein a host cell comprising the vector stably expresses the vector.

23. The kit according to claim 17, wherein the separate container containing the recombinant oncolytic adenovirus comprises the recombinant oncolytic adenovirus in a dose ranging from $5 \times 10^7$ to $5 \times 10^{12}$ vp/day and the separate container containing the NK cells comprises the NK cells in a dose ranging from $1 \times 10^9$ to $3 \times 10^9$ cells/day.

24. The kit according to claim 17, wherein the NK cells are selected from autologous NK cells and allogeneic NK cells.

25. The kit according to claim 24, wherein the NK cells are in vitro expanded autologous NK cells or in vitro expanded allogeneic NK cells.

26. The kit according to claim 17, wherein the recombinant oncolytic adenovirus is formulated to be administered via intratumoral injection or administered intravenously and the NK cells are formulated to be administered intravenously.

\* \* \* \* \*

```
                       SEQUENCE LISTING

<160> NUMBER OF SEQ ID NOS: 25

<210> SEQ ID NO 1
<211> LENGTH: 23
<212> TYPE: DNA
<213> ORGANISM: artificial sequence
<220> FEATURE:
<223> OTHER INFORMATION: the sequence is synthesized

<400> SEQUENCE: 1
ggaagatctg gactgaaaat gag                                              23

<210> SEQ ID NO 2
<211> LENGTH: 24
<212> TYPE: DNA
<213> ORGANISM: artificial sequence
<220> FEATURE:
<223> OTHER INFORMATION: the sequence is synthesized

<400> SEQUENCE: 2
tgaggtcaga tgtaaccaag atta                                             24

<210> SEQ ID NO 3
<211> LENGTH: 33
<212> TYPE: DNA
<213> ORGANISM: artificial sequence
<220> FEATURE:
<223> OTHER INFORMATION: the sequence is synthesized

<400> SEQUENCE: 3
cgcgtcgact actgtaatag taatcaatta cgg                                   33

<210> SEQ ID NO 4
<211> LENGTH: 33
<212> TYPE: DNA
<213> ORGANISM: artificial sequence
<220> FEATURE:
<223> OTHER INFORMATION: the sequence is synthesized

<400> SEQUENCE: 4
gacgtcgact aagatacatt gatgagtttg gac                                   33

<210> SEQ ID NO 5
<211> LENGTH: 21
<212> TYPE: DNA
<213> ORGANISM: artificial sequence
<220> FEATURE:
<223> OTHER INFORMATION: the sequence is synthesized

<400> SEQUENCE: 5
tccggtttct atgccaaacc t                                                21

<210> SEQ ID NO 6
<211> LENGTH: 22
<212> TYPE: DNA
<213> ORGANISM: artificial sequence
<220> FEATURE:
<223> OTHER INFORMATION: the sequence is synthesized
```

<400> SEQUENCE: 6
tcctccggtg ataatgacaa ga                                    22

<210> SEQ ID NO 7
<211> LENGTH: 22
<212> TYPE: DNA
<213> ORGANISM: artificial sequence
<220> FEATURE:
<223> OTHER INFORMATION: the sequence is synthesized

<400> SEQUENCE: 7
ccattacctt tgactcttgt gt                                    22

<210> SEQ ID NO 8
<211> LENGTH: 22
<212> TYPE: DNA
<213> ORGANISM: artificial sequence
<220> FEATURE:
<223> OTHER INFORMATION: the sequence is synthesized

<400> SEQUENCE: 8
ggtagtcctt gtatttagta tc                                    22

<210> SEQ ID NO 9
<211> LENGTH: 29
<212> TYPE: DNA
<213> ORGANISM: artificial sequence
<220> FEATURE:
<223> OTHER INFORMATION: the sequence is synthesized

<400> SEQUENCE: 9
catgccttct tgcctcttgt ctcttagat                             29

<210> SEQ ID NO 10
<211> LENGTH: 30
<212> TYPE: DNA
<213> ORGANISM: artificial sequence
<220> FEATURE:
<223> OTHER INFORMATION: the sequence is synthesized

<400> SEQUENCE: 10
ccatgggtgg aatcatattg gaacatgtaa                            30

<210> SEQ ID NO 11
<211> LENGTH: 32
<212> TYPE: DNA
<213> ORGANISM: artificial sequence
<220> FEATURE:
<223> OTHER INFORMATION: the sequence is synthesized

<400> SEQUENCE: 11
cgcgtcgaca tgaggatatt tgctgtcttt at                         32

<210> SEQ ID NO 12
<211> LENGTH: 32
<212> TYPE: DNA
<213> ORGANISM: artificial sequence
<220> FEATURE:
<223> OTHER INFORMATION: the sequence is synthesized

<400> SEQUENCE: 12
ccgctcgagc gtctcctcca aatgtgtatc ac                         32

<210> SEQ ID NO 13
<211> LENGTH: 24

<212> TYPE: DNA
<213> ORGANISM: artificial sequence
<220> FEATURE:
<223> OTHER INFORMATION: the sequence is synthesized

<400> SEQUENCE: 13
cgcctattac acccactcgt gcag                                    24

<210> SEQ ID NO 14
<211> LENGTH: 62
<212> TYPE: DNA
<213> ORGANISM: artificial sequence
<220> FEATURE:
<223> OTHER INFORMATION: the sequence is synthesized

<400> SEQUENCE: 14
caccgggaaa tggaggataa gaacattcaa gagatgttct tatcctccat ttccttttt    60 tg                                                            62

<210> SEQ ID NO 15
<211> LENGTH: 62
<212> TYPE: DNA
<213> ORGANISM: artificial sequence
<220> FEATURE:
<223> OTHER INFORMATION: the sequence is synthesized

<400> SEQUENCE: 15
agctcaaaaa agggaaatgg aggataagaa catctcttga atgttcttat cctccatttc    60
cc                                                            62

<210> SEQ ID NO 16
<211> LENGTH: 53
<212> TYPE: DNA
<213> ORGANISM: artificial sequence
<220> FEATURE:
<223> OTHER INFORMATION: the sequence is synthesized

<400> SEQUENCE: 16
gggaaatgga ggataagaac attcaagaga tgttcttatc ctccatttcc ctt          53

<210> SEQ ID NO 17
<211> LENGTH: 62
<212> TYPE: DNA
<213> ORGANISM: artificial sequence
<220> FEATURE:
<223> OTHER INFORMATION: the sequence is synthesized

<400> SEQUENCE: 17
caccggatcc agtcacctct gaacattcaa gagatgttca gaggtgactg gatcctttt    60 tg                                                            62

<210> SEQ ID NO 18
<211> LENGTH: 62
<212> TYPE: DNA
<213> ORGANISM: artificial sequence
<220> FEATURE:
<223> OTHER INFORMATION: the sequence is synthesized

<400> SEQUENCE: 18
agctcaaaaa aggatccagt cacctctgaa catctcttga atgttcagag gtgactggat    60
cc                                                            62

<210> SEQ ID NO 19

<211> LENGTH: 53
<212> TYPE: DNA
<213> ORGANISM: artificial sequence
<220> FEATURE:
<223> OTHER INFORMATION: the sequence is synthesized

<400> SEQUENCE: 19
ggatccagtc acctctgaac attcaagaga tgttcagagg tgactggatc ctt    53

<210> SEQ ID NO 20
<211> LENGTH: 62
<212> TYPE: DNA
<213> ORGANISM: artificial sequence
<220> FEATURE:
<223> OTHER INFORMATION: the sequence is synthesized

<400> SEQUENCE: 20
caccgagaat caacacaaca actaattcaa gagattagtt gttgtgttga ttctcttttt    60
tg    62

<210> SEQ ID NO 21
<211> LENGTH: 62
<212> TYPE: DNA
<213> ORGANISM: artificial sequence
<220> FEATURE:
<223> OTHER INFORMATION: the sequence is synthesized

<400> SEQUENCE: 21
agctcaaaaa agagaatcaa cacaacaact aatctcttga attagttgtt gtgttgattc    60
tc    62

<210> SEQ ID NO 22
<211> LENGTH: 53
<212> TYPE: DNA
<213> ORGANISM: artificial sequence
<220> FEATURE:
<223> OTHER INFORMATION: the sequence is synthesized

<400> SEQUENCE: 22
gagaatcaac acaacaacta attcaagaga ttagttgttg tgttgattct ctt    53

<210> SEQ ID NO 23
<211> LENGTH: 59
<212> TYPE: DNA
<213> ORGANISM: artificial sequence
<220> FEATURE:
<223> OTHER INFORMATION: the sequence is synthesized

<400> SEQUENCE: 23
caccgttctc cgaacgtgtc acgtcaagag attacgtgac acgttcggag aatttttg    59

<210> SEQ ID NO 24
<211> LENGTH: 59
<212> TYPE: DNA
<213> ORGANISM: artificial sequence
<220> FEATURE:
<223> OTHER INFORMATION: the sequence is synthesized

<400> SEQUENCE: 24
agctcaaaaa attctccgaa cgtgtcacgt aatctcttga cgtgacacgt tcggagaac    59

<210> SEQ ID NO 25
<211> LENGTH: 50
<212> TYPE: DNA
<213> ORGANISM: artificial sequence

```
<220> FEATURE:
<223> OTHER INFORMATION: the sequence is synthesized

<400> SEQUENCE: 25
gttctccgaa cgtgtcacgt caagagatta cgtgacacgt tcggagaatt            50
```